(12) United States Patent
Hayakawa et al.

(10) Patent No.: US 8,329,707 B2
(45) Date of Patent: Dec. 11, 2012

(54) SUBSTITUTED PYRAZINE COMPOUNDS

(75) Inventors: Masahiko Hayakawa, Tokyo (JP);
Yoshiyuki Kido, Tokyo (JP); Takahiro Nigawara, Tokyo (JP); Mitsuaki Okumura, Tokyo (JP); Akira Kanai, Tokyo (JP); Keisuke Maki, Tokyo (JP); Nobuaki Amino, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 78 days.

(21) Appl. No.: 12/812,385

(22) PCT Filed: Jan. 16, 2009

(86) PCT No.: PCT/JP2009/050508
§ 371 (c)(1),
(2), (4) Date: Jul. 9, 2010

(87) PCT Pub. No.: WO2009/091014
PCT Pub. Date: Jul. 23, 2009

(65) Prior Publication Data
US 2010/0286171 A1 Nov. 11, 2010

(30) Foreign Application Priority Data
Jan. 18, 2008 (JP) ................ P2008-008671

(51) Int. Cl.
*A61K 31/4965* (2006.01)
(52) U.S. Cl. .................. 514/255.06; 544/336
(58) Field of Classification Search ........... 514/255.06; 544/336
See application file for complete search history.

(56) References Cited

U.S. PATENT DOCUMENTS

| | | | |
|---|---|---|---|
| 2001/0039344 A1 | 11/2001 | Bizzarro et al. | |
| 2008/0021032 A1 | 1/2008 | Berthel et al. | |
| 2010/0286171 A1* | 11/2010 | Hayakawa et al. ...... | 514/255.05 |

FOREIGN PATENT DOCUMENTS

| | | |
|---|---|---|
| EP | 1 921 074 | 5/2008 |
| EP | 2 116 533 | 11/2009 |
| EP | 2 116 535 | 11/2009 |
| JP | 2004-506632 | 3/2004 |
| WO | 00/58293 | 10/2000 |
| WO | 01/44216 | 6/2001 |
| WO | 01/83465 | 11/2001 |
| WO | 01/85706 | 11/2001 |
| WO | 01/85707 | 11/2001 |
| WO | 02/08209 | 1/2002 |
| WO | 02/14312 | 2/2002 |
| WO | 02/46173 | 6/2002 |
| WO | 03/095438 | 11/2003 |
| WO | 2004/050645 | 6/2004 |
| WO | 2004/052869 | 6/2004 |
| WO | 2004/063179 | 7/2004 |
| WO | 2004/063194 | 7/2004 |
| WO | 2004/072031 | 8/2004 |
| WO | 2004/072066 | 8/2004 |
| WO | 2005/095417 | 10/2005 |
| WO | 2005/095418 | 10/2005 |
| WO | 2005/103021 | 11/2005 |
| WO | 2006/016194 | 2/2006 |
| WO | 2006/058923 | 6/2006 |
| WO | 2007/007886 | 1/2007 |
| WO | 2007/026761 | 3/2007 |
| WO | 2007/041365 | 4/2007 |
| WO | 2007/041366 | 4/2007 |
| WO | 2007/051845 | 5/2007 |
| WO | 2007/051846 | 5/2007 |
| WO | 2007/051847 | 5/2007 |
| WO | 2008/005914 | 1/2008 |
| WO | 2008/005964 | 1/2008 |
| WO | 2008/078674 | 7/2008 |

OTHER PUBLICATIONS

Jordan, V. C. Nature Reviews: Drug Discovery, 2, 2003, 205.*
Sarabu, R. Expert Opin. Ther. Patents, 18(7), 2008, 759-768.*
Hackam, et al. JAMA, 296(14), 2006, 1731-1732.*

* cited by examiner

*Primary Examiner* — Douglas M Willis
(74) *Attorney, Agent, or Firm* — Fitzpatrick, Cella, Harper & Scinto

(57) ABSTRACT

Phenylacetamide compounds of the formula

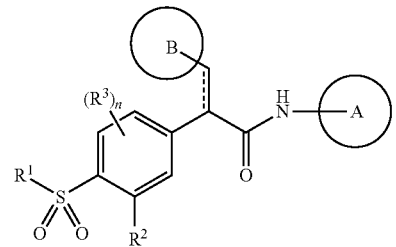

having sulfonyl group and cycloalkyl group on the phenyl group and having heteroaryl group on the nitrogen atom in the amide have an excellent glucokinase activation action.

16 Claims, No Drawings

SUBSTITUTED PYRAZINE COMPOUNDS

CROSS-REFERENCE TO RELATED APPLICATIONS

This application is a 371 of PCT Application No. PCT/JP2009/050508 filed Jan. 16, 2009.

STATEMENT REGARDING FEDERALLY SPONSORED RESEARCH OR DEVELOPMENT

None

THE NAMES OF THE PARTIES TO A JOINT RESEARCH AGREEMENT

None

INCORPORATION-BY-REFERENCE OF MATERIAL SUBMITTED ON A COMPACT DISC

None

BACKGROUND OF THE INVENTION (1) Field of the Invention

The present invention relates to a pharmaceutical, in particular, a novel phenylacetamide derivative which is useful as an agent for treating diabetes.

(2) Description of Related Art

GK (glucokinase (ATP:D-hexose 6-phosphotransferase, EC2.7.1.1)) is an enzyme which is expressed in the pancreas and the liver and phosphorylates hexose, and its presence in the brain has also been revealed in recent years. This enzyme belongs to the hexokinase family and is also called an alias hexokinase IV. In comparison with other hexokinases, GK has characteristics such as 1) it has low affinity for glucose as its substrate and shows a Km value close to the blood glucose concentration, 2) it is not inhibited by glucose 6-phosphate which is its enzyme reaction product, 3) it has about half molecular weight of 50 kDa, and the like.

The human glucokinase gene is positioned at the 7th chromosome 7p13 as a single gene and controlled by 30 kb or more distant tissue-specific different promoters in pancreatic β cells and hepatic cells and uses a different first exon but the other exons 2 to 10 are common. Accordingly, in the pancreatic and hepatic GK proteins, only the N-terminal 15 residues are different.

Accompanied by the increase of blood glucose level, glucose concentration in the pancreatic β cells quickly reaches its equilibrium via a glucose transporting carrier GLUT 2, and GK detects a change in the intracellular glucose concentration and activates the glycolytic pathway. As a result of this, ATP/ADP ratio in the pancreatic β cells increases and the $K_{ATP}$ channel is closed, and a voltage-dependent Ca channel detects this and the intracellular calcium concentration is thereby increased and release of insulin occurs. That is, GK acts as a glucose sensor in the pancreatic β cells and carries an important role in the control of insulin secretion. GK also acts as a glucose sensor in the liver, responds to the increase of blood glucose level and converts glucose into glucose 6-phosphate. As a result of this, production of glycogen increases, and the glycolytic pathway is also activated and the gluconeogenesis in the liver is thereby inhibited.

In patients whose glucose phosphorylation ability was reduced due to gene mutation of GK, hyperglycemia occurs frequently and juvenile diabetes is generated (MODY 2). On the other hand, in patients who show a low value of the Km value of GK activity due to a gene mutation, hypoglycemia is recognized after meal and at the time of fasting. That is, GK acts as a glucose sensor in human too and thereby plays an important role in maintaining normal blood glucose level. From these facts, it is expected that an agent capable of activating GK becomes an excellent therapeutic agent for type II diabetes, which corrects hyperglycemia after meal by accelerating glucose-dependent insulin secretion from the pancreatic β cells and, at the same time, inhibits release of glucose from the liver. Further, there also is a possibility that excess acceleration of insulin secretion does not occur due to acceleration of glucose uptake into the liver under hyperglycemic state after meal and therefore that the pancreatic secondary failure as a conventional problem with sulfonylurea (SU) agents can be avoided. In addition, it has been reported in recent years that apoptosis is induced when a mouse cultured pancreatic cell (MIN6N8) is cultured under high glucose. In addition, since apoptosis of the MIN6N8 cell was inhibited when glucokinase was over-expressed in this cell (Diabetes 54:2) 2602-2611 (2005), it is expected that a GK activating agent shows a pancreas protective action.

The GK which exists in the brain is a pancreas type and frequently expressed in the nerve of feeding center VMH (Ventromedial hypothalamus). Glucose-sensitive nerves are classified into a glucose excitatory GE (Glucose Excited)-neuron and a glucose suppressive GI (Glucose Inhibited)-neuron. The presence of mRNA and protein of GK is found in about 70% of the GE-neuron and about 40% of the GI-neuron.

In these glucose-sensitive nerves, GK detects increase of the intracellular glucose and activates the glycolytic pathway, and the intracellular ATP/ADP ratio thereby increases. As a result of this, the $K_{ATP}$ channel is closed in the GE-neuron, frequency of action potential of the neuron is increased and a neurotransmitter is released. On the other hand, it is considered that a Cl⁻ channel is concerned in the GI-neuron. In a rat in which expression of GK mRNA is increased in the VMH, compensatory action for the glucose-deficient state is reduced.

Receptors for leptin and insulin concerning in the feeding behavior are also present in the glucose-sensitive nerves. In the GE-neuron under a high glucose condition, leptin and insulin open the $K_{ATP}$ channel and reduce the frequency of action potential. In addition, the NPY (Neuropeptide Y)-neuron which functions for the appetite promotion at ARC (arcuate nucleus) is suppressive for glucose and the POMC (Proopiomelanocortin)-neuron which functions for the appetite suppression is excitatory for glucose (Diabetes 53:2521-2528 (2004)). From these facts, it is expected that feeding behavior is suppressed by activating GK of the central, which is effective for the treatment of obesity and metabolic syndrome.

A number of compounds having the GK activation action have been reported and the compounds whose clinical efficacy has been confirmed have been already reported. However, a novel GK activator having a excellent profile regarding reduction in various side effects (actions for hERG and CYP) and solubility is still in great demand.

Phenylacetamide derivatives having a GK activation action have been reported in Patent References 1 to 25. However, there is no disclosure of cycloalkyl as a substituent which corresponds to $R^2$ of the compound of the present invention.

Phenylacetamide derivatives having a GK activation action have been reported in Patent References 26 to 28. However, there is no specific disclosure of the compound of the present invention.

Phenylacetamide derivatives having a GK activation action have been reported in Patent References 29 to 30, which have been published after the priority date of the present application. However, there is no specific disclosure of the compound of the present invention.

Heteroaryl derivatives having a GK activation action have been reported in Patent References 31 and 32. However, the ring which corresponds to a phenyl group of the phenylacetamide of the present invention is heteroaryl. Further, there is no disclosure of cycloalkyl as a substituent which corresponds to R² of the compound of the present invention.

[Patent Reference 1] Pamphlet of International Publication WO 00/58293
[Patent Reference 2] Pamphlet of International Publication WO 01/83465
[Patent Reference 3] Pamphlet of International Publication WO 01/85706
[Patent Reference 4] Pamphlet of International Publication WO 01/85707
[Patent Reference 5] Pamphlet of International Publication WO 02/08209
[Patent Reference 6] Pamphlet of International Publication WO 02/14312
[Patent Reference 7] Pamphlet of International Publication WO 03/95438
[Patent Reference 8] Pamphlet of International Publication WO 2006/58923
[Patent Reference 9] Pamphlet of International Publication WO 2007/026761
[Patent Reference 10] Pamphlet of International Publication WO 2005/095417
[Patent Reference 11] Pamphlet of International Publication WO 2005/095418
[Patent Reference 12] Pamphlet of International Publication WO 2006/016194
[Patent Reference 13] Pamphlet of International Publication WO 2007/051847
[Patent Reference 14] Pamphlet of International Publication WO 2004/072031
[Patent Reference 15] Pamphlet of International Publication WO 01/44216
[Patent Reference 16] Specification of U.S. Patent Application Publication No. 2001/0039344
[Patent Reference 17] Pamphlet of International Publication WO 02/46173
[Patent Reference 18] Pamphlet of International Publication WO 2004/52869
[Patent Reference 19] Pamphlet of International Publication WO 2004/063179
[Patent Reference 20] Pamphlet of International Publication WO 2005/103021
[Patent Reference 21] Pamphlet of International Publication WO 2007/007886
[Patent Reference 22] Pamphlet of International Publication WO 2007/041365
[Patent Reference 23] Pamphlet of International Publication WO 2007/041366
[Patent Reference 24] Pamphlet of International Publication WO 2007/051845
[Patent Reference 25] Pamphlet of International Publication WO 2007/051846
[Patent Reference 26] Pamphlet of International Publication WO 2004/050645
[Patent Reference 27] Pamphlet of International Publication WO 2008/05914
[Patent Reference 28] Pamphlet of International Publication WO 2008/05964
[Patent Reference 29] Specification of U.S. Patent Application Publication No. 2008/21032
[Patent Reference 30] Pamphlet of International Publication WO 2008/078674
[Patent Reference 31] Pamphlet of International Publication WO 2004/063194
[Patent Reference 32] Pamphlet of International Publication WO 2004/72066

BRIEF SUMMARY OF THE INVENTION

An object of the present invention is to provide a pharmaceutical having a GK activation action, in particular, a novel compound which is useful as an agent for treating diabetes.

BRIEF DESCRIPTION OF THE SEVERAL VIEWS OF THE DRAWING(S)

None

DETAILED DESCRIPTION OF THE INVENTION

The present inventors have made extensive studies on a compound having a GK activation action, and as a result, confirmed that a phenylacetamide derivative having sulfonyl group and cycloalkyl group on the phenyl group and having heteroaryl group on the nitrogen atom in an amide has an excellent GK activation action, and also discovered the existence of a compound for which various side effects (actions for hERG and CYP) and/or solubility are improved, thereby completing the present invention.

That is, the present invention relates to a phenylacetamide derivative represented by general formula (I) or a salt thereof.

[Chem. 1]

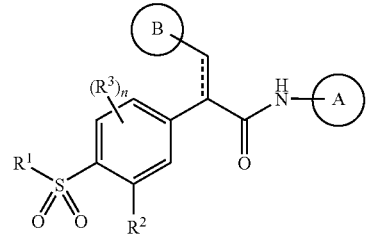

(I)

(The symbols in the formula represent the following meanings:

$R^1$: lower alkyl, halogeno-lower alkyl, or cycloalkyl,
$R^2$: cycloalkyl,
$R^3$: halogen, lower alkyl, halogeno-lower alkyl, —OR⁰, or —O-halogeno-lower alkyl,
$R^0$: the same as or different from each other, each representing —H or lower alkyl,
Ring A: heteroaryl which may be substituted,
Ring B: aryl or heteroaryl which may each be substituted, or

X: the same as or different from each other, each representing —C($R^4$)($R^5$)—, —C(O)—, —O—, —S(O)p-, or —N($R^0$)—,
m: an integer of 2 to 7,
$R^4$ and $R^5$: the same as or different from each other, each representing —H, halogen, lower alkyl, halogeno-lower alkyl, —OR⁰, or —O-halogeno-lower alkyl,
n and p: the same as or different from each other, each representing 0, 1 or 2, provided that

----- means a single bond or a double bond. The same shall apply hereinafter.)

Further, the present invention relates to a pharmaceutical composition comprising the phenylacetamide derivative represented by formula (I) or a pharmaceutically acceptable salt thereof, and a pharmaceutically acceptable carrier, in particular, a pharmaceutical composition, which is a GK activator or an agent for preventing and/or treating diabetes, obesity, or metabolic syndrome. That is, (1) a pharmaceutical composition comprising the compound represented by formula (I) or a pharmaceutically acceptable salt thereof, and a pharmaceutically acceptable carrier, (2) the pharmaceutical composition of (1), which is a GK activator, (3) the pharmaceutical composition of (1), which is an agent for preventing and/or treating diabetes, (4) the pharmaceutical composition of (3), which is an agent for preventing and/or treating type II diabetes, (5) the pharmaceutical composition of (1), which is an agent for preventing and/or treating obesity, (6) the pharmaceutical composition of (1), which is an agent for preventing and/or treating metabolic syndrome, (7) use of the compound represented by formula (I) or a pharmaceutically acceptable salt thereof, for the manufacture of a GK activator or an agent for preventing and/or treating diabetes, obesity, or metabolic syndrome, (8) a method for preventing and/or treating diabetes, obesity, or metabolic syndrome, comprising administering to a patient a therapeutically effective amount of the compound represented by formula (I) or a salt thereof.

Further, the present application relates to a pharmaceutical, in particular a GK activator, which comprises the phenylacetamide derivative represented by formula (I) or a salt thereof as an active ingredient.

EFFECT OF THE INVENTION

Since the compound of the present invention has a GK activation action, it is useful as a therapeutic and preventive agent for diabetes, particularly type II diabetes. It is also useful as a therapeutic and preventive agent for complications of diabetes including nephropathy, retinopathy, neuropathy, disturbance of peripheral circulation, cerebrovascular accidents, ischemic heart disease and arteriosclerosis. In addition, it is also useful as a therapeutic and preventive agent for obesity and metabolic syndrome by suppressing overeating.

BEST MODE FOR CARRYING OUT THE INVENTION

Hereinbelow, the present invention will be described in detail.

In the present specification, the "lower alkyl" preferably refers to linear or branched alkyl having 1 to 6 carbon atoms (hereinafter simply referred to as $C_{1-6}$), and specific examples thereof include methyl, ethyl, n-propyl, isopropyl, n-butyl, isobutyl, sec-butyl, tert-butyl, n-pentyl, n-hexyl group, and the like. It is more preferably $C_{1-4}$ alkyl, and particularly preferably methyl, ethyl, normal propyl, isopropyl, or tert-butyl.

The "lower alkylene" is preferably linear or branched $C_{1-6}$ alkylene, and specific examples thereof include methylene, ethylene, trimethylene, tetramethylene, pentamethylene, hexamethylene, propylene, methylmethylene, ethylethylene, 1,2-dimethylethylene, 1,1,2,2-tetramethylethylene group, and the like. It is more preferably $C_{1-4}$ alkylene, and further preferably methylene, ethylene, or trimethylene.

The "halogen" means F, Cl, Br, or I.

The "halogeno-lower alkyl" means $C_{1-6}$ alkyl substituted with one or more halogen atoms. It is preferably lower alkyl substituted with 1 to 5 halogen atoms, and more preferably fluoromethyl, difluoromethyl, or trifluoromethyl.

The "cycloalkyl" refers to a $C_{3-10}$ saturated hydrocarbon ring group, which may have a bridge. Specific examples thereof include cyclopropyl, cyclobutyl, cyclopentyl, cyclohexyl, cycloheptyl, cyclooctyl, adamantyl group, and the like.

It is preferably $C_{3-8}$ cycloalkyl, more preferably cyclopropyl, cyclobutyl, cyclopentyl, or cyclohexyl, and further preferably cyclopropyl.

The "aryl" refers to a $C_{6-14}$ monocyclic to tricyclic aromatic hydrocarbon ring group, and it is more preferably phenyl or naphthyl, and further preferably phenyl.

The "heteroaryl" group means a 5- to 15-membered, preferably 5- to 10-membered monocyclic to tricyclic aromatic hetero ring group containing 1 to 4 hetero atoms selected from oxygen, sulfur, and nitrogen. The ring atom, sulfur or nitrogen, may be oxidized to form an oxide. Specific examples thereof include pyrrolyl, pyrazolyl, imidazolyl, triazolyl, tetrazolyl, furyl, oxazolyl, isoxazolyl, oxadiazolyl, thienyl, thiazolyl, isothiazolyl, thiadiazolyl, pyridyl, pyridazinyl, pyrimidinyl, pyrazinyl, indolyl, isoindolyl, indazolyl, benzimidazolyl, benzofuryl, benzoxazolyl, benzothienyl, benzothiazolyl, [1,3]thiazolo[5,4-b]pyridinyl, quinolyl, isoquinolyl, quinazolinyl, quinoxalinyl, cinnolinyl, phthalazinyl, naphthylizinyl, carbazolyl, and the like. It is preferably 5- to 6-membered monocyclic heteroaryl, and more preferably pyrazolyl, pyrazinyl, thiazolyl, thiadiazolyl, or pyridyl.

The "hetero ring" group refers to a 3- to 15-membered, preferably 5- to 10-membered, monocyclic to tricyclic hetero ring group containing 1 to 4 hetero atoms selected from oxygen, sulfur, and nitrogen, which contains a saturated ring, an aromatic ring, and a partially hydrogenated ring group thereof. The ring atom, sulfur or nitrogen may be oxidized to form an oxide or dioxide. Specific examples thereof include pyridyl, pyrazinyl, pyrimidinyl, pyridazinyl, imidazolyl, benzimidazolyl, benzofuranyl, benzothienyl, benzothiadiazolyl, benzothiazolyl, benzoisothiazolyl, benzoxazolyl, benzoisoxazolyl, pyrrolyl, pyrrolidinyl, thienyl, furyl, dioxazolyl, dioxolanyl, triazinyl, triazolyl, thiazolyl, thiadiazolyl, oxadiazolyl, pyrazolyl, pyrazolidinyl, isothiazolyl, oxazolyl, isoxazolyl, quinolyl, isoquinolyl, tetrahydroquinolyl, tetrahydroisoquinolyl, quinazolinyl, quinoxalinyl, phthalazinyl, piperidyl, piperazinyl, azepanyl, diazepanyl, tetrahydropyranyl, dioxolanyl, morpholinyl, methylenedioxyphenyl, ethylenedioxyphenyl, trithianyl, indolyl, isoindolyl, indolinyl, indazolyl, tetrahydrobenzimidazolyl, chromanyl, chromonyl, benzimidazolonyl group, and the like. It is preferably a 5- to 9-membered monocyclic to bicyclic hetero ring group, more preferably a 5- to 6-membered monocyclic hetero ring group, and further preferably pyrazolyl, pyrazinyl, thiazolyl, thiadiazolyl, pyridyl, tetrahydrofuranyl, tetrahydropyranyl, or dioxolanyl.

In the formula (I), in case

----- is a double bond, the compound of the present invention may be either of an E form/Z form, although it is denoted in the formula (I) that Ring B and the benzene ring are in a Z configuration with respect to the double bond. It is preferable that Ring B and the benzene ring are in a Z configuration with respect to the double bond.

The "which may be substituted" represents "which is not substituted" or "which is substituted with 1 to 5 substituents, which are the same as or different from each other". Further, if it has a plurality of substituents, the substituents may be the same as or different from each other.

In Ring A, the substituent in the "heteroaryl" which may be substituted is preferably a group selected from Group G, more preferably halogen, cyano, lower alkyl which may be substituted with —OR⁰, —OR⁰, —O-lower alkylene-OR⁰, or —C(O)R⁰, and further preferably lower alkyl which may be substituted with —OH, or —O-lower alkylene-OH.

Group G: halogen, cyano, lower alkyl which may be substituted with —OR⁰, halogeno-lower alkyl, lower alkylene-OC(O)R⁰, lower alkylene-O-hetero ring group, —OR⁰, —O- halogeno-lower alkyl, —O-lower alkylene-OR⁰, —S(O)p-lower alkyl, —S(O)p-lower alkylene-OR⁰, —C(O)R⁰, —C(O)-lower alkylene-OR⁰, —CO₂R⁰, lower alkylene-CO₂R⁰, —O-lower alkylene-CO₂R⁰, —S(O)p-lower alkylene-CO₂R⁰, —C(O)N(R)₂, or a hetero ring group.

However, the hetero ring group in Group G may be substituted with halogen, lower alkyl, halogeno-lower alkyl, —OR⁰, —O-halogeno-lower alkyl, or oxo.

The acceptable substituent for "aryl" and "heteroaryl" in Ring B, each of which may be substituted, is preferably halogen, lower alkyl, halogeno-lower alkyl, —OR⁰, or —O-halogeno-lower alkyl.

Preferred embodiments of the present invention will be described below.

(a) R¹ is preferably methyl, trifluoromethyl, or cyclopropyl, and more preferably cyclopropyl.

(b) R² is preferably C₃₋₆ cycloalkyl, and more preferably cyclopropyl.

(c) n is preferably 0 or 1, and more preferably 0.

(d) Ring A is preferably a 5- to 6-membered monocyclic heteroaryl which may be substituted, more preferably pyrazolyl, thiazolyl, thiadiazolyl, pyridyl or pyrazinyl, each of which may be substituted with group(s) selected from the group consisting of halogen, cyano, lower alkyl which may be substituted with —OR⁰, —OR⁰, —O-lower alkylene-OR⁰, and —C(O)R⁰, further preferably pyrazolyl, thiazolyl, pyridyl, or pyrazinyl, each of which may be substituted with group(s) selected from the group consisting of halogen, lower alkyl which may be substituted with —OR⁰, —OR⁰, —O-lower alkylene-OR⁰, and —C(O)R⁰, and even further preferably pyrazolyl or pyrazinyl which may be substituted with group(s) selected from the group consisting of halogen, lower alkyl which may be substituted with —OR⁰, —OR⁰, and —O-lower alkylene-OR⁰.

(e) Ring B is preferably

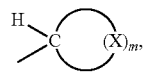

m is 4 or 5, none or one X is —CH(F)—, —CH(OH)—, —C(O)—, or —O—, and the remaining X is —CH₂—, and more preferably 3-hydroxycyclopentyl or 3-oxocyclopentyl.

(f)

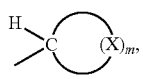

is preferably a single bond. In another embodiment, it is preferably a double bond. In an even further embodiment, in the case where Ring A is pyrazolyl which may be substituted, it is preferably a double bond.

In another preferred embodiment, a compound formed by the combination of preferred groups as described in (a) to (f) above is preferable.

Further, other preferred embodiments of the compound of the present invention represented by formula (I) are described below.

(1) The compound represented by formula (I), wherein n is 0.

(2) The compound as described in (1), wherein R¹ is methyl, trifluoromethyl, or cyclopropyl.

(3) The compound as described in (2), wherein R² is cyclopropyl.

(4) The compound as described in (3), wherein Ring B is m is 4 or 5, zero or one X is —CH(F)—, —CH(OH)—, —C(O)—, or —O—, and the remaining X is —CH₂—.

(5) The compound as described in (4), wherein Ring A is pyrazolyl, thiazolyl, thiadiazolyl, pyridyl, or pyrazinyl, each of which may be substituted with group(s) selected from the group consisting of halogen, cyano, lower alkyl which may be substituted with —OR⁰, —OR⁰, —O-lower alkylene-OR⁰, and —C(O)R⁰.

(6) The compound as described in (5), wherein is a single bond.

(7) The compound as described in (5), wherein is a double bond.

(8) The compound represented by formula (I), which is selected from the group consisting of:
(2E)-2-[3-cyclopropyl-4-(cyclopropylsulfonyl)phenyl]-N-(5-methylpyrazin-2-yl)-3-[(1S)-3-oxocyclopentyl]acrylamide,
(2E)-2-[3-cyclopropyl-4-(cyclopropylsulfonyl)phenyl]-N-(1-methyl-1H-pyrazol-3-yl)-3-[(1S)-3-oxocyclopentyl]acrylamide,
(2E)-2-[3-cyclopropyl-4-(cyclopropylsulfonyl)phenyl]-N-(5-fluoro-1,3-thiazol-2-yl)-3-[(1S)-3-oxocyclopentyl]acrylamide,
(2R)—N-(4-acetyl-1,3-thiazol-2-yl)-2-[3-cyclopropyl-4-(cyclopropylsulfonyl)phenyl]-3-[(1R)-3-oxocyclopentyl]propanamide,
(2R)-2-[3-cyclopropyl-4-(cyclopropylsulfonyl)phenyl]-N-(5-methylpyridin-2-yl)-3-[(1R)-3-oxocyclopentyl]propanamide,
(2R)-2-[3-cyclopropyl-4-(cyclopropylsulfonyl)phenyl]-N-(5-methylpyrazin-2-yl)-3-[(1R)-3-oxocyclopentyl]propanamide,
(2R)-2-[3-cyclopropyl-4-(cyclopropylsulfonyl)phenyl]-N-[5-(hydroxymethyl)pyrazin-2-yl]-3-[(1R)-3-oxocyclopentyl]propanamide,
(2R)—N-(5-chloropyrazin-2-yl)-2-[3-cyclopropyl-4-(cyclopropylsulfonyl)phenyl]-3-[(1R)-3-oxocyclopentyl]propanamide,
(2R)-2-[3-cyclopropyl-4-(cyclopropylsulfonyl)phenyl]-N-(5-methoxypyrazin-2-yl)-3-[(1R)-3-oxocyclopentyl]propanamide,
(2R)-2-[3-cyclopropyl-4-(cyclopropylsulfonyl)phenyl]-3-[(1R)-3-hydroxycyclopentyl]-N-(5-methylpyrazin-2-yl)propanamide,
(2R)-2-[3-cyclopropyl-4-(cyclopropylsulfonyl)phenyl]-3-[(1R)-3-hydroxycyclopentyl]-N-(5-methoxypyrazin-2-yl)propanamide,
(2R)-2-[3-cyclopropyl-4-(cyclopropylsulfonyl)phenyl]-N-[5-(2-hydroxy ethoxy)pyrazin-2-yl]-3-[(1R)-3-oxocyclopentyl]propanamide, and
(2R)-2-[3-cyclopropyl-4-(cyclopropylsulfonyl)phenyl]-N-[5-(2-hydroxy-2-methylpropoxy)pyrazin-2-yl]-3-[(1R)-3-oxocyclopentyl]propanamide,
or a pharmaceutically acceptable salt thereof.

There are cases in which the compound of the present invention exists also in the form of other tautomers and geometrical isomers depending on the kind of substituent groups. Though sometimes described in this description only as an embodiment of these isomers, these isomers are also included in the present invention and isolated isomers or mixtures thereof are also included therein.

Also, the compound (I) sometimes has an asymmetric carbon atom or axial asymmetry, and optical isomers based on this (e.g., (R)-form, (S)-form and the like) can be present. The present invention includes all of the mixtures and isolated forms of these optical isomers.

Further, pharmacologically acceptable prodrugs of the compound (I) are also included in the present invention. The pharmacologically acceptable prodrug is a compound which has a group that can be converted into amino group, OH, $CO_2H$ or the like of the present invention by solvolysis or under a physiological condition. As the groups which form prodrugs, for example, the groups described in Prog. Med., 5, 2157-2161 (1985) and "Iyakuhin no Kaihatsu (Pharmaceutical Research and Development)" (Hirokawa Publishing Company, 1990) Vol. 7 Bunshi Sekkei (Drug Design) 163-98 can be cited.

In addition, there are cases in which the compound of the present invention forms acid addition salts or salts with bases depending on the kind of substituent groups, and such salts are included in the present invention with the proviso that they are pharmaceutically acceptable salts. Illustratively, acid addition salts with inorganic acids (e.g., hydrochloric acid, hydrobromic acid, hydriodic acid, sulfuric acid, nitric acid, phosphoric acid and the like) or organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid and the like), salts with inorganic bases (e.g., sodium, potassium, magnesium, calcium, aluminum and the like) or with organic bases (e.g., methylamine, ethylamine, ethanolamine, lysine, ornithine and the like), ammonium salts and the like may be exemplified.

The present invention also includes various hydrates and solvates of the compounds of the present invention and pharmaceutically acceptable salts thereof, and substances having polymorphism thereof.

(Production Methods)

The compounds of the present invention and pharmaceutically acceptable salts thereof can be produced by various conventionally known synthetic methods making use of their basal backbones or the characteristics based on the kinds of substituent groups. In that case, depending on the kinds of functional group, there is a case in which replacement of said functional group by an appropriate protecting group (a group which can be easily converted into said functional group), at a stage of the starting materials to intermediates, is effective in view of the production techniques. As such a functional group, it includes amino group, hydroxyl group, carboxyl group and the like, as their protecting groups, the protecting groups described for example in "Protective Groups in Organic Synthesis (3rd edition, 1999)" edited by Greene and Wuts, can be cited, and these may be optionally selected and used in response to the reaction conditions. By such a method, a desired compound can be obtained by carrying out the reaction by introducing said protecting group and then removing the protecting group as occasion demands.

In addition, a prodrug of the compound (I) can be produced by introducing a specific group at a stage of the starting materials to intermediates similar to the case of the aforementioned protecting group or by carrying out the reaction using the obtained compound (I). The reaction can be carried out by employing the general methods which are conventionally known by those skilled in the art, such as esterification, amidation, dehydration and the like.

The following describes typical production methods of the compounds of the present invention. In this connection, the production methods of the present invention are not limited to the Examples shown below.

(Production Process 1)

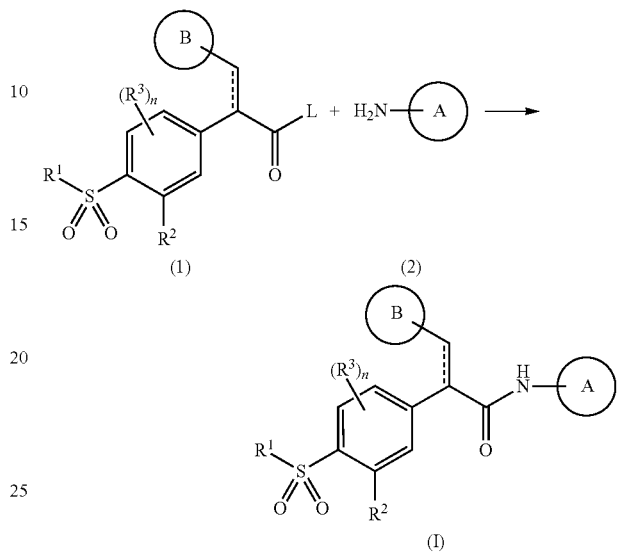

(In the formula, L represents a leaving group or OH. The same shall apply hereinafter.)

The present production process is a method for obtaining the compound of the present invention represented by (I) by subjecting a compound (1) and a compound (2) to an amidation reaction. Examples of the leaving group of L include organic sulfonic acid groups such as methanesulfonyloxy or p-toluenesulfonyloxy, and the like, halogen, and the like. Alternatively, as the (1), various acid anhydrides can be used.

In the case where L is a hydroxyl group, the reaction can be carried out in the presence of a condensing agent such as N,N'-dicyclohexylcarbodiimide (DCC), 1-ethyl-3-(3'-dimethylaminopropyl)carbodiimide (WSC), 1,1'-carbonyldiimidazole (CDI), diphenylphosphoryl azide (DPPA), phosphorous oxychloride/pyridine, triphenylphosphine/N-bromosuccinimide, and the like, and in some cases, can be carried out further in the presence of additives (for example, N-hydroxysuccinimide (HONSu), 1-hydroxybenzotriazole (HOBt), and the like). In the case where L is a leaving group, it may be preferable in some cases to carry out the reaction in the presence of an inorganic base such as sodium carbonate, potassium carbonate, sodium hydrogen carbonate, potassium hydrogen carbonate, and the like, or an organic base such as triethylamine, diisopropyl ethylamine, pyridine, and the like.

Regarding the solvent, solvents inert to the reaction such as aromatic hydrocarbons (e.g., benzene, toluene, xylene and the like), ethers (e.g., diethyl ether, tetrahydrofuran (THF), dioxane, diglyme, 1,2-dimethoxyethane, 2-methoxy diethyl ether and the like), halogenated hydrocarbons (e.g., dichloromethane, 1,2-dichloroethane, chloroform and the like), acetonitrile, ethyl acetate and the like can be used alone or as a mixture of two or more. In addition, the compound (1) and compound (2) are optionally used in equivalent molar to excess amounts in response to the reaction and compounds.

Various substituents in the formula (I) can be easily converted into other functional groups by a reaction which is apparent to a skilled person in the art, or a modified method thereof, using the compound (I) of the present invention as a starting material. For example, a process that can be usually used by a skilled person in the art, such as alkylation, hydrolysis, amidation, reduction, and the like can be carried out in any combination thereof.

(Preparation of Starting Compounds)

The starting compound in the production process above can be prepared, for example, by a method as below, a known method, or a modified method thereof.

(Starting Material Synthesis 1)

(Starting Material Synthesis 2)

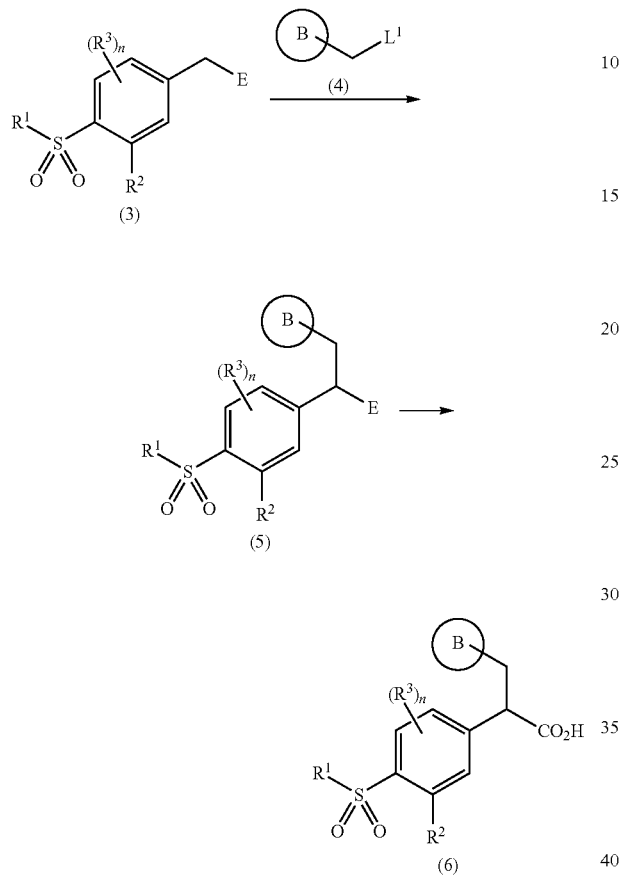

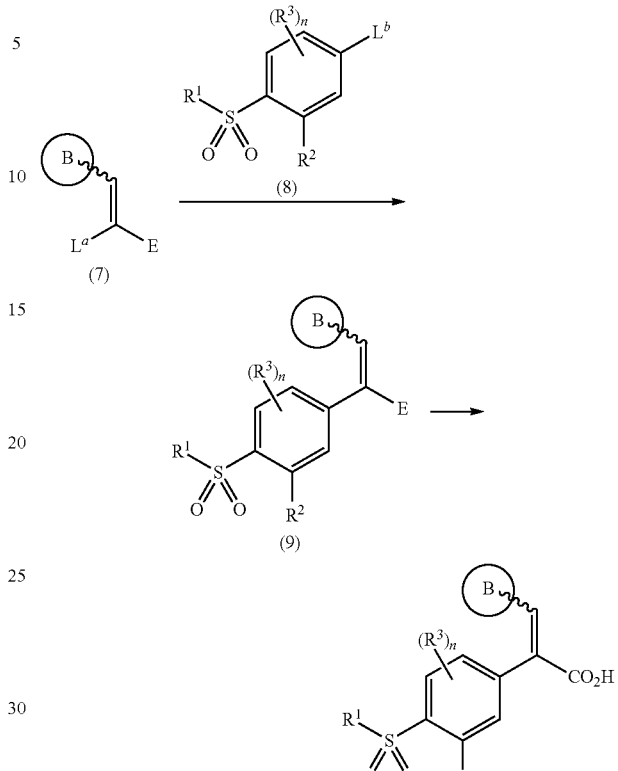

(In the formula, E means an equivalent carboxylic acid, such as an ester, a nitrile, and the like, and $L^1$ means a leaving group such as halogen and the like. The same shall apply hereinafter.)

The starting compound (6) can be prepared by subjecting a corresponding ester or nitrile compound (5) to a hydrolysis reaction under an acidic or basic condition. As the acid, hydrochloric acid, hydrobromic acid, or the like can be used, and as the base, lithium hydroxide, sodium hydroxide, potassium hydroxide, or the like can be used.

The compound (5) can be prepared by subjecting a compound (3) and a compound (4) to an alkylation reaction. The reaction can be carried out by an ordinary alkylation reaction method, and can be carried out from under cooling to under heating in the presence of a base such as lithium diisopropylamide (LDA), sodium hydride, potassium hexamethyldisilazide, potassium t-butoxide, butyl lithium, and the like, in a solvent inert to the reaction such as ethers, 1,3-dimethyltetrahydropyrimidinone (DMPU), and the like.

In addition, when there is an asymmetric carbon in the starting compound (6), an optically active starting compound (6) can be obtained, for example, by isolating a racemic compound (6) as a diastereomer through its amidation with an asymmetry auxiliary group such as (4R)-4-benzyl-1,3-oxazolidin-2-one and the like, and then hydrolyzing.

(In the formula, either of $L^a$ and $L^b$ represents halogen or a trifluoromethylsulfonyloxy group, and the other represents —B(OR$^Z$)$_2$ or —SnR$^0{}_3$, and R$^Z$ represents H or lower alkyl, or two R$^Z$'s may be combined to form lower alkylene. The same shall apply hereinafter.)

The starting compound (10) can be prepared by hydrolyzing a compound (9) as its corresponding ester or nitrile compound, in the same manner as the hydrolysis of starting material synthesis 1. According to the kind of the compounds, the compound (9) which is a mixture of a Z compound and an E compound can be used to selectively obtain the compound (10) in which Ring B and the benzene ring are in a Z configuration with respect to a double bond.

The compound (9) can be prepared by a coupling reaction of a compound (7) and a compound (8).

The coupling reaction can be carried out under cooling, under room temperature, or under heating using the compound (7) and the compound (8) in an equivalent amount, or one of them in an excess amount, in a solvent such as ethers, alcohols such as methanol, ethanol, and the like, halogenated hydrocarbons, aromatic hydrocarbons, water and the like, or in a mixed solvent thereof, using a palladium complex such as tetrakistriphenylphosphine palladium, palladium acetate, 1,1'-bis(diphenylphosphino)ferrocene-palladium(II)dichloride, and the like as a catalyst. In addition, it may be advantageous in some cases for the smooth progress of the reaction to carry out the reaction in the presence of a base such as sodium carbonate, cesium carbonate, sodium tert-butoxide, and the like, or a lithium salt such as lithium chloride, lithium bromide, and the like.

(Starting Material Synthesis 3)

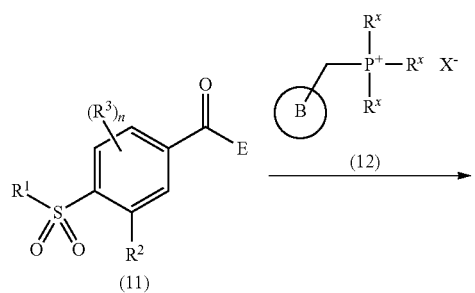

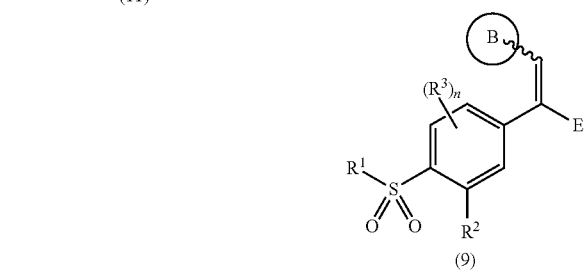

(In the formula, $R^x$ represents a residual part of a Wittig reagent, and $X^-$ represents a counter anion such as halogen anion and the like. The same shall apply hereinafter.)

The compound (9) can be prepared by a Wittig reaction of a compound (11) and a compound (12).

The Wittig reaction can be carried out from under cooling to under heating in a solvent such as the aforementioned aromatic hydrocarbons, ethers, halogenated hydrocarbons, N,N-dimethylformamide (DMF), N,N-dimethylacetamide (DMA), N-methylpyrrolidone (NMP), dimethylsulfoxide (DMSO), acetonitrile, and the like, using potassium carbonate, potassium tert-butoxide, sodium hydride, n-butyl lithium, lithium hexadisilazide, or the like as a base.

(Starting Material Synthesis 4)

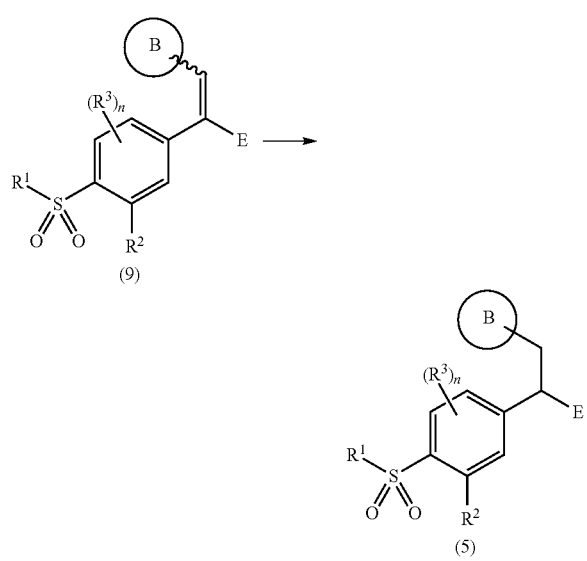

The compound (5) can be prepared by reducing the double bond of the compound (9).

The reduction reaction can be carried out from at room temperature to under heating in a solvent inert to the reaction such as the aforementioned aromatic hydrocarbons, ethers, halogenated hydrocarbons, esters such as ethyl acetate and the like, DMF, DMA, NMP, acetic acid, and the like, under a hydrogen atmosphere at an ordinary pressure or under pressurization, using palladium-carbon, palladium hydroxide-carbon, Raney nickel, platinum, or the like as a catalyst. Depending on the compound, it may be advantageous in some cases for the smooth progress of the reaction to carry out the reaction in the presence of an acid (preferably hydrochloric acid, acetic acid, or the like).

Alternatively, a reduction reaction by a hydride type reactant can be used. For example, the reduction reaction can be carried out from under cooling to under heating to allow sodium borohydride or sodium borohydride/nickel chloride hexahydrate to undergo an action in alcohols, ethers or a mixed solvent thereof.

(Starting Material Synthesis 5)

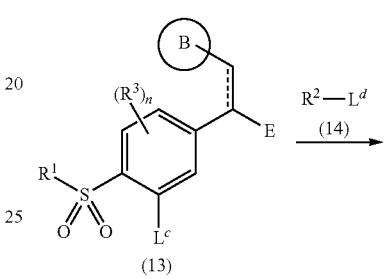

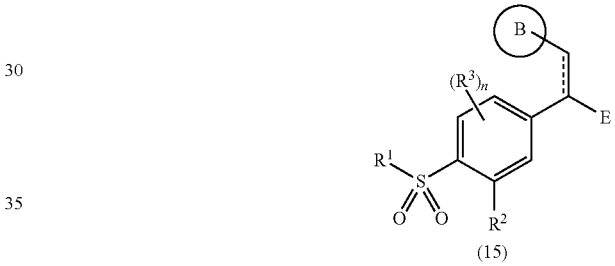

(In the formula, $L^c$ represents halogen or a trifluoromethylsulfonyloxy group, $L^d$ represents $-B(OR^Y)_2$, $R^Y$ represents H or lower alkyl, or two $R^Y$'s may be combined to form lower alkylene. The same shall apply hereinafter.)

The compound (15) can be prepared by a coupling reaction of a compound (13) and a compound (14).

The coupling reaction can be carried out under cooling, at room temperature, or under heating using the compound (13) and the compound (14) in an equivalent amount, or one of them in an excess amount, in a solvent such as ethers, alcohols, halogenated hydrocarbons, aromatic hydrocarbons, water, and the like, or in a mixed solvent thereof, using a palladium complex such as, tetrakistriphenylphosphine palladium, palladium acetate, 1,1'-bis(diphenylphosphino)ferrocene-palladium(II)dichloride or the like as a catalyst. In addition, it may be advantageous in some cases for the smooth progress of the reaction to carry out the reaction in the presence of a base such as sodium carbonate, cesium carbonate, sodium tert-butoxide, tripotassium phosphate, and the like.

The compound (13) can be prepared in the same manner as for the compound (5) or the compound (9).

The compounds of the present invention are isolated and purified as free compounds or their pharmaceutically acceptable salts, hydrates, solvates or polymorphic substances. A pharmaceutically acceptable salt of the compound (I) of the present invention can also be produced by subjecting to a general salt formation reaction.

The isolation and purification are carried out by employing general chemical operations such as extraction, fractional crystallization, various types of fractional chromatography and the like.

Various isomers can be separated by selecting an appropriate starting material compound or making use of a difference in a physicochemical property between isomers. For example, an optically active isomer can be introduced into a stereochemically pure isomer by a general optical resolution method (e.g., a fractional crystallization for introducing into a diastereomer salt with optically active base or acid, a chiral column-aided chromatography or the like). In addition, it is also able to produce from an appropriate optically active starting material compound.

The pharmacological activity of the compound of the present invention was confirmed by the following tests.

Test Example 1

Measurement of Glucokinase (GK) Activation

The present test was carried out in accordance with the method described in Science 301: 370-373, 2003 and with partial modification thereof. Hereinafter, the summary is described.

First, the cloning of GK (GenBank No. AK122876) was carried out. 5'-TAGAATTCATGGCGATGGATGTCA-CAAG-3'(SEQ ID NO: 1) and 5'-ATCTCGAGTCACTGGC-CCAGCATACAG-3'(SEQ ID NO: 2) were used as primers, and pME18S-FL3-Glucokinase isoform 2 was used as a template to carry out PCR. The obtained reaction product was TA-cloned into a pGEM-T easy vector, digested with EcoRI and XhoI, and introduced to the pGEX-5X-1 vector digested in the same manner by ligation. By using this plasmid DNA (pGEX-human Glucokinase 2), a recombinant human hepatic type GK (GST-hGK2) fused with GST (Glutathione S-transferase) was expressed in *Escherichia coli* (BL21 strain) and purified by Glutathione Sepharose.

The reaction of GK was carried out at 27° C. on a 96-well plate. First, 1 μL of the test compound (final concentration 10 μM) that has been diluted with dimethylsulfoxide (DMSO) was added to 89 μL of an enzyme mixed liquid (all final concentration 25 mM HEPES pH 7.4, 25 mM KCl, 2 mM $MgCl_2$, 1 mM ATP, 0.1% BSA, 1 mM DTT, 1 mM NADP (nicotinamide adenine dinucleotide phosphate), 2.5 U/ml glucose-6-phosphate dehydrogenase, GST-hGK2 adjusted to $\Delta OD_{Cont}$ of about 0.05 to 0.10). Subsequently, 10 μL of a substrate solution (final concentration 5 mM glucose) was added to start the reaction. In order to quantify a final product NADPH, an absorbance at a wavelength of 340 nm was measured, and the GK activation (%) of the test compound was calculated from the increase of absorbance during the first 10 minutes ($\Delta OD$) after initiation of the reaction.

GK activation (%)=[($\Delta OD_{Test}$)−($\Delta OD_{Cont}$)]/($\Delta OD_{Cont}$)×100

$\Delta OD_{Test}$: ΔOD at test compound
$\Delta OD_{Cont}$: ΔOD at DMSO

Results of the measurement as described above are shown in Table 1. In this connection, Ex indicates Example Number.

TABLE 1

| Ex | GK activation (%) |
|---|---|
| 1 | 330 |
| 2 | 365 |
| 3 | 328 |
| 4-1 | 355 |
| 5 | 410 |
| 6 | 336 |
| 7 | 418 |
| 9 | 333 |
| 10 | 357 |
| 11 | 433 |
| 15 | 284 |
| 22-1 | 197 |

TABLE 1-continued

| Ex | GK activation (%) |
|---|---|
| 22-2 | 199 |
| 24 | 345 |
| 25 | 334 |
| 26 | 231 |
| 27 | 211 |
| 28 | 314 |
| 29 | 300 |
| 30 | 309 |
| 31 | 387 |
| 32 | 410 |
| 33 | 375 |
| 34 | 245 |
| 35 | 265 |
| 36 | 332 |
| 37 | 260 |
| 38 | 386 |
| 39 | 286 |
| 40 | 397 |
| 41 | 362 |
| 43 | 391 |
| 44 | 389 |
| 45 | 377 |
| 46 | 392 |
| 47 | 297 |
| 48 | 257 |
| 51 | 352 |
| 55 | 315 |
| 70 | 282 |
| 72 | 311 |
| 74 | 337 |
| 75 | 307 |
| 78 | 273 |
| 79 | 297 |
| 81 | 211 |
| 83 | 345 |
| 85 | 257 |
| 99 | 326 |

Test Example 2

Oral Glucose Tolerance Test in Normal Mouse

The test compound was dissolved in a solvent (5% Cremophor, aqueous 5% DMSO solution), and to an ICR mouse after fasting overnight was orally administered 10 mg/kg of the test compound, and after 30 minutes, oral glucose loading was carried out. Immediately before the administration of the test compound, immediately before the glucose loading, and 0.25, 0.5, 1, and 2 hours after the glucose loading, blood was collected and blood glucose levels were measured. An AUC lowering rate (%) of the blood glucose levels from immediately before the glucose loading to 2 hours after the glucose loading with respect to that of the solvent control group was calculated.

The results are shown in Table 2.

TABLE 2

| Ex | Blood glucose lowering rate (%) |
|---|---|
| 4-1 | 39 |
| 9 | 52 |
| 10 | 51 |
| 11 | 50 |
| 15 | 49 |
| 22-1 | 55 |
| 22-2 | 52 |
| 36 | 45 |
| 51 | 55 |
| 55 | 56 |
| 70 | 60 |

TABLE 2-continued

| Ex | Blood glucose lowering rate (%) |
|---|---|
| 72 | 59 |
| 78 | 50 |
| 79 | 45 |
| 83 | 51 |

Test Example 3

Oral Glucose Tolerance Test in Mouse Fed High Fat Diet

The test compound was dissolved in a solvent (5% Cremophor, aqueous 5% DMSO solution), and to a C57BL/6 mice after loading a high fat diet for about 30 days and then fasting overnight was orally administered 1 mg/kg of the test compound, and after 30 minutes, oral glucose loading was carried out. Immediately before the administration of the test compound, immediately before the glucose loading, and 0.25, 0.5, 1, and 2 hours after the glucose loading, blood was collected and blood glucose levels were measured. An AUC lowering rate (%) of the blood glucose levels from immediately before the glucose loading to 2 hours after the glucose loading with respect to that of the solvent control was calculated.

The results are shown in Table 3.

TABLE 3

| Ex | Blood glucose lowering rate (%) |
|---|---|
| 4-1 | 32 |
| 36 | 43 |

Test Example 4

Oral Glucose Tolerance Test in Normal Rat

The test compound was dissolved in a solvent (5% Cremophor, aqueous 5% DMSO solution), and to an SD rat after fasting overnight was orally administered 1 mg/kg of the test compound, and after 30 minutes, oral glucose loading was carried out. Immediately before the administration of the test compound, immediately before the glucose loading, and 0.5, 1, and 2 hours after the glucose loading, blood was collected and blood glucose levels were measured. An AUC lowering rate (%) of the blood glucose levels from immediately before the glucose loading to 2 hours after the glucose loading with respect to that of the solvent control was calculated.

The results are shown in Table 4.

TABLE 4

| Ex | Blood glucose lowering rate (%) |
|---|---|
| 4-1 | 25 |
| 11 | 20 |
| 15 | 22 |
| 22-1 | 27 |
| 22-2 | 25 |
| 36 | 40 |
| 83 | 17 |

From the above test results, it was confirmed that the compounds of the present invention have an excellent GK activation action. In addition, since compounds in which various side effects (actions for hERG and CYP) and/or solubility were improved were also found, it is evident that the compounds of the present invention are useful as an agent for preventing and treating diabetes and the like.

The pharmaceutical preparations which comprise one or two or more of the compounds (I) of the present invention or salts thereof as the active ingredient can be prepared by generally used methods using carriers, excipients and the like for pharmaceutical preparations use which are generally used in this field.

The administration may be either oral administration by tablets, pills, capsules, granules, powders, solutions and the like or parenteral administration by injections for intraarticular injection, intravenous injection, intramuscular injection and the like, suppositories, eye drops, eye ointments, transdermal solutions, ointments, transdermal patches, transmucosal solutions, transmucosal patches, inhalations and the like.

As the solid composition for oral administration by the present invention, tablets, powders, granules and the like are used. In such a solid composition, one or more active substances are mixed with at least one inert filler such as lactose, mannitol, glucose, hydroxypropylcellulose, microcrystalline cellulose, starch, polyvinyl pyrrolidone and/or magnesium alminometasilicate or the like. In accordance with the usual way, the composition may contain inert additives such as lubricants (e.g., magnesium stearate and the like), disintegrators (e.g., carboxymethylstarch sodium and the like), stabilizers, and solubilizing agents. As occasion demands, the tablets or pills may be coated with a sugar coating or a film of a gastric or enteric substance.

As the liquid composition for oral administration, pharmaceutically acceptable emulsions, solutions, suspensions, syrups, elixirs and the like are included, and a generally used inert diluent such as purified water or ethanol is included. In addition to the inert diluent, said liquid composition may contain auxiliary agents such as solubilizing agents, moistening agents, suspending agents and the like, sweeteners, correctives, aromatics and antiseptics.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oil (e.g., olive oil or the like), alcohols (e.g., ethanol or the like), polysorbate 80 (the name in Pharmacopeia) and the like. Such a composition may further contain tonicity agents, antiseptics, moistening agents, emulsifying agents, dispersing agents, stabilizing agents or solubilizing agents. These are sterilized by, for example, filtration through a bacteria retaining filter, formulation of bactericides or irradiation. In addition, these can also be used by producing sterile solid compositions and dissolving or suspending them in sterile water or a sterile solvent for injection prior to use.

Transmucosal preparations such as inhalations, transnasal preparations and the like are used in the form of solid, liquid or semisolid, and can be produced in accordance with the conventionally known methods. For example, conventionally known fillers and also pH adjusting agents, antiseptics, surfactants, lubricants, stabilizers, thickeners and the like may be optionally added. An appropriate device for inhalation or blowing can be used for the administration. For example, a compound can be administered as such or as a powder of formulated mixture, or as a solution or suspension in combination with a pharmaceutically acceptable carrier, by using a conventionally known device (e.g., a measured administration inhalation device or the like) or a sprayer. The dry powder inhaler or the like may be for single or multiple administration use, and a dry powder or powder-containing capsule can be used. Alternatively, it may be in the form of a pressurized aerosol spray or the like which uses an appropriate propellant such as chlorofluoroalkane, hydrofluoroalkane, or a suitable gas such as carbon dioxide or the like.

Generally, in the case of oral administration, the daily dose is approximately from 0.001 to 100 mg/kg, preferably from 0.1 to 30 mg/kg, further preferably from 0.1 to 10 mg/kg, per body weight, and this is administered once or by dividing into 2 to 4 doses. When intravenously administered, it is suitable that the daily dose is approximately from 0.0001 to 10 mg/kg body weight, and this is administered once a day or dividing it into two or more times per day. In addition, in the case of a transmucosal preparation, approximately from 0.001 to 100 mg/kg per body weight is administered once a day or dividing into two or more doses. The dose is optionally decided in response to individual case by taking symptom, age, sex and the like into consideration.

EXAMPLES

Hereinbelow, the production processes of the compound (I) of the present invention are described in detail with reference to Examples. The compound of the present invention is not limited to the compounds described in Examples below. Also, the production processes of the starting compounds are shown in Production Examples.

Production Example 1

To a solution of 60% sodium hydride (496 mg) in DMF (10 mL) was added a solution of 1H-pyrazol-3-amine (1.03 g) in DMF (5 mL) under ice-cooling, followed by stirring at room temperature for 30 minutes. A solution of [(3-bromopropoxy) methyl]benzene (2.93 g) in DMF (10 mL) was added thereto under ice-cooling, followed by stirring at room temperature overnight. Saturated brine and saturated aqueous sodium bicarbonate were added thereto, followed by extraction with chloroform. The organic layer was dried over anhydrous magnesium sulfate and concentrated. The obtained crude product was purified by silica gel column chromatography (hexane:ethyl acetate=1:1-1:3) to obtain 1-[3-(benzyloxy) propyl]-1H-pyrazol-3-amine (835 mg) as a pale yellow oily substance.

Production Example 2

To a solution of 2-bromobenzenethiol (50 g) in DMF (500 mL) were added bromocyclopropane (41.6 g), potassium carbonate (54.8 g), and triphenylmethanethiol (1.46 g), followed by stirring at an internal temperature of 80° C. for 24 hours. After cooling to room temperature, water and ethyl acetate were added thereto, and the organic layer was then separated. The organic layer was washed with a saturated aqueous sodium hydrogen carbonate solution and saturated brine, dried over anhydrous magnesium sulfate, and then concentrated under reduced pressure. The residue was purified by silica gel column chromatography to obtain 1-bromo-2-(cyclopropylsulfanyl)benzene (49.3 g).

Production Example 3

To a suspension of aluminum chloride (40.2 g) in dichloromethane (1200 mL) was added dropwise ethyl chloro(oxo) acetate (32.3 g) at 0° C., followed by stirring at the same temperature for 1 hour. To the reaction mixture was added dropwise a solution of 1-bromo-2-(cyclopropylsulfanyl)benzene (49.3 g) in dichloromethane (280 mL) while keeping it at 5° C. or lower, followed by stirring at room temperature for 1 hour. The reaction mixture was cooled to 0° C., and water was added thereto to stop the reaction. The reaction mixture was extracted with ethyl acetate and the organic layer was sequentially washed with water, a saturated aqueous sodium hydrogen carbonate solution, and saturated brine. The solution was dried over anhydrous magnesium sulfate and then concentrated. The residue was purified by silica gel chromatography to obtain ethyl[3-bromo-4-(cyclopropylsulfanyl)phenyl] (oxo)acetate (29.8 g).

Production Example 4

To a suspension of triphenyl(tetrahydro-2H-pyran-4-yl-methyl)phosphonium iodide (9.27 g) in THF (70 mL) was added dropwise lithium-1,1,1,3,3,3-hexamethyldisilazide (1 M THF solution, 19.0 mL) at 0° C. or lower, followed by stirring at around 0° C. for 1 hour. To the reaction mixture was added dropwise a solution of ethyl[3-bromo-4-(cyclopropyl-sulfanyl)phenyl](oxo)acetate (5.0 g) in THF (10 mL) at 2° C. or lower. The reaction mixture was stirred for 30 minutes under ice-cooling and then stirred at room temperature for 15 hours. 4 M Hydrochloric acid was added dropwise thereto at 10° C. or lower, adjusted to pH 7, and then concentrated under reduced pressure. To the residue was added diethyl ether and the resulting solid was separated by filtration. The filtrate was washed with water and saturated brine, dried over anhydrous magnesium sulfate, and then concentrated under reduced pressure. The residue was purified by silica gel column chromatography to obtain ethyl 2-[3-bromo-4-(cyclopropylsulfa-nyl)phenyl]-3-(tetrahydro-2H-pyran-4-yl)acrylate (4.57 g) as an (E)/(Z)-mixture of olefin.

Production Example 5

Ethyl 2-[3-bromo-4-(cyclopropylsulfanyl)phenyl]-3-(tet-rahydro-2H-pyran-4-yl)acrylate (4.57 g) was dissolved in dichloromethane (91 mL), followed by ice-cooling. To this solution was added m-chloroperbenzoic acid (5.75 g) in 5 divided portions. It was warmed to room temperature, followed by stirring for 2 hours. To the reaction mixture was added a saturated aqueous sodium hydrogen carbonate solution, and further added a 1 M aqueous sodium sulfite solution. The organic layer was separated and the aqueous layer was then extracted with dichloromethane. The organic layer was further washed with a saturated aqueous sodium hydrogen carbonate solution, dried over anhydrous sodium sulfate, and then concentrated under reduced pressure to obtain ethyl 2-[3-bromo-4-(cyclopropylsulfonyl)phenyl]-3-(tetrahydro-2H-pyran-4-yl)acrylate (4.72 g) as an (E)/(Z)-mixture.

Production Example 6

Ethyl 2-[3-bromo-4-(cyclopropylsulfonyl)phenyl]-3-(tet-rahydro-2H-pyran-4-yl)acrylate (4.72 g), cyclopropylboronic acid (1.37 g), and tetrakis(triphenylphosphine)palladium (615 mg) were dissolved in toluene (142 mL), and to this solution were added tripotassium phosphate (4.07 g, 19.2 mmol) and water (7.1 mL). The mixture was stirred at 100° C. for 20 hours. It was cooled to room temperature, and water and ethyl acetate were added thereto. The organic layer was separated, washed with saturated aqueous sodium hydrogen carbonate solution and saturated brine, and then dried over anhydrous magnesium sulfate. After concentration under reduced pressure, the obtained residue was purified by silica gel column chromatography to obtain ethyl 2-[3-cyclopro-pyl-4-(cyclopropylsulfonyl)phenyl]-3-(tetrahydro-2H-py-ran-4-yl)acrylate (3.50 g) as an (E)/(Z)-mixture of olefin.

Production Example 7

Ethyl 2-[3-cyclopropyl-4-(cyclopropylsulfonyl)phenyl]-3-(tetrahydro-2H-pyran-4-yl)acrylate (3.50 g) was dissolved in methanol (42 mL), and to this solution was slowly added a 8 M aqueous potassium hydroxide solution (27 mL), which had been separately prepared. After stirring at room temperature for 3 hours, methanol was evaporated under reduced pressure, followed by careful addition of concentrated hydrochloric acid for neutralization. The resulting solid was collected by filtration, washed with water, and then dried by blowing air. The crude product was washed with diethyl ether and then dried under reduced pressure to obtain (2E)-2-[3-cyclopropyl-4-(cyclopropylsulfonyl)phenyl]-3-(tetrahydro-2H-pyran-4-yl)acrylic acid (2.47 g).

Production Example 8

To a solution of 3-(iodomethyl)tetrahydrofuran (10.1 g) in acetonitrile (101 mL) was added triphenylphosphine (13.1 g), followed by heating under reflux for 1 week. The solution was concentrated under reduced pressure, followed by addition of diethyl ether. The resulting solid was collected by filtration and washed with diethyl ether to obtain triphenyl(tetrahydrofuran-3-ylmethyl)phosphonium iodide (18.8 g) as a white solid.

Production Example 9

To a solution of 1H-pyrazol-3-amine in DMSO (15 mL) was added potassium hydroxide (3.18 g) at room temperature. After stirring at room temperature for 30 minutes, to the reaction mixture was added a solution of (R)-(+)-4-chloromethyl-2,2-dimethyl-1,3-dioxolane (3.0 g) in DMSO (10 mL), followed by stirring at room temperature for 3 days. To the reaction mixture was added water, followed by extraction with ethyl acetate. The organic layer was dried over anhydrous magnesium sulfate and concentrated. The obtained crude product was purified by basic silica gel column chromatography (hexane:ethyl acetate=1:1-1:3) to obtain 1-{[(4S)-2,2-dimethyl-1,3-dioxolan-4-yl]methyl}-1H-pyrazol-3-amine (1.0 g) as a pale violet oily substance.

Production Example 10

Ethyl 2-[3-bromo-4-(cyclopropylsulfanyl)phenyl]-3-(8,8-dimethyl-6,10-dioxaspiro[4.5]dec-2-yl)acrylate (1.63 g, (E)/(Z)-mixture) was dissolved in methanol (16.3 mL)-THF (16.3 mL) mixed solvent, followed by ice-cooling. To this solution was added a solution of Oxone (registered trademark, 2.43 g) in water (16.3 mL), followed by warming to room temperature and stirring for 1 hour. A saturated aqueous sodium hydrogen carbonate solution was added thereto, and further added a 1 M aqueous sodium sulfite solution and ethyl acetate. The organic layer was separated and the aqueous layer was then extracted with ethyl acetate. The organic layer was further washed with a saturated aqueous sodium hydrogen carbonate solution, dried over anhydrous sodium sulfate, and then concentrated under reduced pressure to obtain ethyl 2-[3-bromo-4-(cyclopropylsulfinyl)phenyl]-3-(8,8-dimethyl-6,10-dioxaspiro[4.5]dec-2-yl)acrylate (1.64 g) as an (E)/(Z)-mixture of olefin.

Production Example 11

Ethyl 2-[3-bromo-4-(cyclopropylsulfanyl)phenyl]-3-(8,8-dimethyl-6,10-dioxaspiro[4.5]dec-2-yl)acrylate (2.40 g, (E)/(Z)-mixture), cyclopropylboronic acid (606 mg, 7.05 mmol), and tetrakis(triphenylphosphine)palladium (272 mg, 0.24 mmol) were dissolved in toluene (72 mL), and to this solution were added tripotassium phosphate (1.80 g, 8.46 mmol) and water (3.6 mL). The mixture was stirred at 100° C. for 20 hours. It was cooled to room temperature, and water and ethyl acetate were added thereto. The organic layer was separated, washed with a saturated aqueous sodium hydrogen carbonate solution and saturated brine, and then dried over anhydrous magnesium sulfate. After concentration under reduced pressure, the obtained residue was purified by silica gel column chromatography. The obtained intermediate was dissolved in dichloromethane (48 mL), followed by ice-cooling. To this solution were added sodium hydrogen carbonate (3.95 g) and then m-chloroperbenzoic acid (1.30 g). It was warmed to room temperature and stirred for 1 hour. Water was added to the reaction mixture to stop the reaction, and 1 M aqueous sodium sulfite solution was further added thereto. The organic layer was separated and the aqueous layer was then extracted with dichloromethane. The organic layer was further washed with a saturated aqueous sodium hydrogen carbonate solution, dried over anhydrous sodium sulfate, and then concentrated under reduced pressure to obtain ethyl 2-[3-bromo-4-(cyclopropylsulfonyl)phenyl]-3-(8,8-dimethyl-6,10-dioxaspiro[4.5]dec-2-yl)acrylate (1.82 g) as an (E)/(Z)-mixture of olefin. The obtained mixture was dissolved in methanol (22.1 mL), and to this solution was slowly added 8 M aqueous potassium hydroxide solution (11.8 mL), which had been separately prepared. After stirring at room temperature for 3 hours, concentrated hydrochloric acid was carefully added to adjust the pH to 1-2. Methanol was evaporated under reduced pressure, followed by carrying out an operation of extraction with chloroform. The organic layer was dried over anhydrous sodium sulfate and concentrated under reduced pressure, and the obtained solid was dried under reduced pressure to obtain (2E)-2-[3-cyclopropyl-4-(cyclopropylsulfonyl)phenyl]-3-(3-oxocyclopentyl)acrylic acid (1.41 g).

Production Example 12

Ethyl 2-[3-bromo-4-(cyclopropylsulfanyl)phenyl]-3-[(2S,3S,7R)-2,3-diphenyl-1,4-dioxaspiro[4.4]non-7-yl]acrylate (2.58 g, (E)/(Z)-mixture) was dissolved in dichloromethane (77 mL), followed by ice-cooling. To this solution was added sodium hydrogen carbonate (7.87 g) and then m-chloroperbenzoic acid (2.31 g). It was stirred for 30 minutes under ice-cooling, and further warmed to room temperature, followed by stirring for 3 hours. Dichloromethane (55 mL) and m-chloroperbenzoic acid (0.32 g) were further added thereto, followed by stirring at room temperature for 1 hour. Water was added to the reaction mixture to stop the reaction and the organic layer was separated. The organic layer was washed with a saturated aqueous sodium hydrogen carbonate solution, dried over anhydrous sodium sulfate, and then concentrated under reduced pressure. The residue was purified by silica gel column chromatography to obtain ethyl 2-[3-bromo-4-(cyclopropylsulfonyl)phenyl]-3-[(2S,3S,7R)-2,3-diphenyl-1,4-dioxaspiro[4.4]non-7-yl]acrylate (2.52 g) as an (E)/(Z)-mixture of olefin.

Production Example 13

Ethyl 2-[3-cyclopropyl-4-(cyclopropylsulfonyl)phenyl]-3-[(2S,3S,7R)-2,3-diphenyl-1,4-dioxaspiro[4.4]non-7-yl]acrylate (1.77 g, (E), (Z) mixture) was dissolved in a mixed solvent of methanol (21.2 mL) and dioxane (21.2 mL), and to this solution was slowly added 8 M aqueous potassium hydroxide solution (21.2 mL), which had been separately prepared. It was stirred at room temperature for 10 minutes, and then stirred in an oil bath at 70° C. for 2 hours under heating. It was left to be cooled to room temperature, and hydrochloric acid was carefully added thereto under ice-cooling. The mixture was stirred for 2 hours under heating in an oil bath at 90° C., and cooled to room temperature again. Chloroform was added thereto and the organic layer was separated. The aqueous layer was extracted with chloroform, combined with the organic layer, dried over anhydrous sodium sulfate and then concentrated under reduced pressure. The residue was purified by silica gel column chromatography to obtain (2E)-2-[3-cyclopropyl-4-(cyclopropylsulfonyl) phenyl]-3-[(1R)-3-oxocyclopentyl]acrylic acid (952 mg).

Production Example 14

To a solution of methyl {5-[(tert-butoxycarbonyl)amino]pyrazin-2-yl}acetate (0.4811 g) in dioxane (5 mL) was added a 4 M hydrogen chloride dioxane solution (5 mL), followed by stirring overnight. The reaction mixture was concentrated and the obtained crude product was collected by filtration and washed with ethyl acetate. The obtained crude product was dissolved in water, and saturated aqueous sodium bicarbonate and ethyl acetate were added thereto, followed by stirring for 1 hour. Saturated brine was added thereto, followed by extraction with ethyl acetate (10 mL×20 times), and the obtained organic layer was washed with saturated brine, dried using anhydrous magnesium sulfate. After concentration under reduced pressure, methyl (5-aminopyrazin-2-yl)acetate (0.2662 g) was obtained as a pale yellow solid.

Production Example 15

To a solution of t-butyl[4-(hydroxymethyl)-1,3-thiazol-2-yl]carbamate (1.21 g) in dichloromethane (15 mL) was added diethylaminosulfur trifluoride (0.73 mL) under cooling in a dry ice-acetone bath, followed by stirring for 30 minutes under cooling as it is in a dry ice acetone bath. To the reaction mixture was added saturated aqueous sodium bicarbonate, followed by extraction with ethyl acetate. The organic layer was washed with saturated brine, dried over anhydrous magnesium sulfate, and then concentrated to obtain t-butyl[4-(fluoromethyl)-1,3-thiazol-2-yl]carbamate (480 mg) as a white solid.

Production Example 16

To a solution of t-butyl[4-(fluoromethyl)-1,3-thiazol-2-yl] carbamate (480 mg) in dichloromethane (5 mL) was added trifluoroacetic acid (1 mL) at room temperature. It was stirred at room temperature for 5 hours. The reaction mixture was concentrated, and saturated aqueous sodium bicarbonate and saturated brine were added thereto. It was extracted with a solvent (chloroform:isopropyl alcohol=4:1). The organic layer was dried over anhydrous magnesium sulfate and concentrated to obtain 4-(fluoromethyl)-1,3-thiazol-2-amine (243 mg) as a pale yellow solid.

Production Example 17

To a solution of triphenylphosphine (607 mg) in dichloromethane (10 mL) was added N-bromosuccinimide (412 mg) under ice-cooling, followed by stirring for 15 minutes under ice-cooling. A solution of (2E)-2-[3-cyclopropyl-4-(cyclopropylsulfonyl)phenyl]-3-[(2R,3R,7S)-2,3-diphenyl-1,4-dioxaspiro[4.4]non-7-yl]acrylic acid (600 mg) in dichloromethane (10 mL) was added thereto under ice-cooling, followed by stirring at room temperature for 0.5 hour. A solution of methyl 6-aminonicotinate (160 mg) in dichloromethane (10 mL) and pyridine (0.17 mL) were added thereto at room temperature, followed by stirring at room temperature overnight. To the reaction mixture was added water, followed by extraction with ethyl acetate. The organic layer was sequentially washed with 1 M hydrochloric acid, saturated aqueous sodium bicarbonate, and saturated brine, and dried over anhydrous magnesium sulfate. The crude product obtained by concentration was purified by silica gel column chromatography (hexane:ethyl acetate=3:1-1:1). To the solution of the obtained pale yellow amorphous dioxane (4 mL) was added a 1 M aqueous sodium hydroxide solution (1.2 mL), followed by stirring at 50° C. for 1 hour. 1 M Hydrochloric acid was added thereto to adjust the pH to 2, and then saturated brine was added thereto. The mixture was extracted with chloroform, and the organic layer was dried over anhydrous magnesium sulfate. The crude product obtained by concentration was purified by silica gel column chromatography (hexane:ethyl acetate=1:1-3:1) to obtain 6-({(2E)-2-[3-cyclopropyl-4-(cyclopropylsulfonyl)phenyl]-3-[(2R,3R,7S)-2,3-diphenyl-1,4-dioxaspiro[4.4]non-7-yl] prop-2-enoyl}amino)nicotinic acid (194 mg) as a white amorphous substance.

Production Example 18

To a solution of 2-amino[1,3]thiazolo[5,4-b]pyridin-5-ol 2 hydrobromide (10 g) in DMF (20 mL) were added potassium carbonate (25.2 g) and 2-bromoethyl acetate (4 mL) at room temperature. It was stirred at 80° C. for 2 hours. To the reaction mixture were added saturated brine and water, followed by extraction with ethyl acetate. The organic layer was dried over anhydrous magnesium sulfate and concentrated. The obtained crude product was purified by silica gel column chromatography (hexane:ethyl acetate=1:2-1:3) to obtain 2-[(2-amino[1,3]thiazolo[5,4-b]pyridin-5-yl)oxy]ethyl acetate (2.97 g) as a pale yellow solid.

Production Example 19

To a solution of ethyl 2-[3-cyclopropyl-4-(cyclopropylsulfonyl)phenyl]-3-[(1S)-3-oxocyclopentyl]acrylate (400 mg) in dichloromethane (5 mL) were added acetic acid (57 µL) and diethylaminosulfur trifluoride (0.71 mL), followed by reflux for 6 hours. The reaction mixture was diluted with chloroform and then sequentially washed with water and saturated brine, and the organic layer was dried over anhydrous magnesium sulfate. After concentration, the residue was purified by silica gel column chromatography (ethyl acetate:hexane=7:3-1:0) to obtain ethyl 2-[3-cyclopropyl-4-(cyclopropylsulfonyl)phenyl]-3-[(1S)-3,3-difluorocyclopentyl]acrylate (250 mg) as a colorless oil.

Production Example 20

A solution of ethyl[3-bromo-4-(cyclopropylsulfanyl)phenyl](oxo)acetate (30 g) in toluene (60 mL) was heated to 50° C., and a 3 M aqueous sodium hydroxide solution (36 mL) was added thereto at an internal temperature of 60° C. or lower, followed by stirring at 50° C. for 1 hour. After leaving it to be cooled at room temperature, water (150 mL) and ethyl acetate (100 mL) were added to the reaction mixture. To the aqueous layer was added concentrated hydrochloric acid (12 mL) under ice-cooling, followed by extraction with ethyl acetate (100 mL×3). The organic layer was washed with saturated brine (100 mL) and dried over anhydrous magnesium sulfate, and the solvent was then evaporated under reduced pressure. The residue was sequentially washed with hexane/ethyl acetate (19/1, 200 mL) and diethyl ether/hexane (1/2, 200 mL) to obtain [3-bromo-4-(cyclopropylsulfanyl) phenyl](oxo)acetic acid (14.7 g) as a pale yellow solid.

Production Example 21

To hydrazine monohydrate (16.9 mL) was added [3-bromo-4-(cyclopropylsulfanyl)phenyl](oxo)acetic acid (15 g) under ice-cooling, followed by stirring at 80° C. for 10 minutes. To the reaction mixture was added potassium hydroxide (8.22 g), followed by stirring at 80° C. for 20 minutes and then stirring at 100° C. overnight. After leaving it to be cooled at room temperature, concentrated hydrochloric acid (50 mL) was added thereto under ice-cooling, followed by extraction with chloroform (50 mL×3). The organic layer was sequentially washed with 1 M hydrochloric acid (50 mL×2) and saturated brine (50 mL), and dried over anhydrous magnesium sulfate, and the solvent was then evaporated under reduced pressure to obtain [3-bromo-4-(cyclopropylsulfanyl)phenyl]acetic acid (13.5 g) as a pale yellow solid.

Production Example 22

A mixture of [3-bromo-4-(cyclopropylsulfanyl)phenyl] acetic acid (13.5 g), concentrated sulfuric acid (0.135 mL), and methanol (40 mL) was stirred under heating and reflux for 4 hours. After leaving to be cooled at room temperature, the solvent was evaporated under reduced pressure, and then a 1 M aqueous sodium hydroxide solution (100 mL) was added to the reaction mixture, followed by extraction with ethyl acetate (100 mL×3). The organic layer was washed with saturated brine (100 mL) and dried over anhydrous sodium sulfate, and the solvent was then evaporated under reduced pressure to obtain methyl [3-bromo-4-(cyclopropylsulfanyl) phenyl]acetate (13.8 g) as a colorless solid.

Production Example 23

To a mixture of diisopropylamine (6.94 mL), 1,3-dimethyltetrahydropyrimidin-2(1H)-one (18 mL) and THF (60 mL) was added 2.64 M n-butyl lithium/hexane solution (18.4 mL) at an internal temperature of −50° C. or lower, followed by stirring at an internal temperature of −50° C. or lower for 1 hour. To the reaction mixture was added dropwise a solution of methyl [3-bromo-4-(cyclopropylsulfonyl)phenyl]acetate (15.0 g) in THF (20 mL)/1,3-dimethyl tetrahydropyrimidin-2(1H)-one (9 mL) at an internal temperature of −50° C. or lower, followed by stirring at the same temperature for 30 minutes, and THF (30 mL) was added thereto, followed by stirring at −20° C. for 1 hour. A solution of (2R,3R,7S)-7-(iodomethyl)-2,3-diphenyl-1,4-dioxaspiro[4.4]nonane (21.8 g) in THF (20 mL) was added dropwise thereto at an internal temperature of −60° C. or lower, followed by stirring at the same temperature for 30 minutes and then stirring at room temperature overnight. To the reaction mixture was added water (200 mL) under ice-cooling, followed by extraction with ethyl acetate (100 mL×3). The organic layer was sequentially washed with water (200 mL) and saturated brine (200 mL), and dried over anhydrous magnesium sulfate, and the solvent was then evaporated under reduced pressure. The residue was purified by silica gel column chromatography (hexane/ethyl acetate 19:1→1:1) to obtain methyl 2-[3-bromo-4-(cyclopropylsulfonyl)phenyl]-3-[(2R,3R,7R)-2,3-diphenyl-1,4-dioxaspiro[4.4]non-7-yl]propionate (20.4 g) as a pale yellow amorphous substance.

Production Example 24

A mixture of methyl 2-[3-cyclopropyl-4-(cyclopropylsulfonyl)phenyl]-3-[(2R,3R,7R)-2,3-diphenyl-1,4-dioxaspiro [4.4]non-7-yl]propionate (66.5 g), 4 M aqueous sodium hydroxide solution (66.5 mL), methanol (66.5 mL), and THF (133 mL) was stirred under heating and reflux for 30 minutes, and left to be cooled at room temperature, and the organic solvent was evaporated under reduced pressure. To the residue was added chloroform (500 mL), and concentrated hydrochloric acid (25 mL) was then added thereto under ice-cooling. The organic layer was washed with saturated brine (200 mL×2) and dried over anhydrous sodium sulfate, and the solvent was then evaporated under reduced pressure to obtain 2-[3-cyclopropyl-4-(cyclopropylsulfonyl)phenyl]-3-[(2R,3R,7R)-2,3-diphenyl-1,4-dioxaspiro[4.4]non-7-yl] propionic acid (64.8 g) as an off-white amorphous substance.

Production Example 25

To a solution of 2-[3-cyclopropyl-4-(cyclopropylsulfonyl) phenyl]-3-[(2R,3R,7R)-2,3-diphenyl-1,4-dioxaspiro[4.4] non-7-yl]propionic acid (70.8 g) in THF (350 mL) were added triethylamine (21 mL) and 2,2-dimethylpropanoyl chloride (19 mL) at an internal temperature of 11° C. or lower under ice-cooling, followed by stirring at room temperature for 1 hour. In another vessel, to a solution of (4R)-4-benzyl-1,3-oxazolidin-2-one (26.3 g) in THF (200 mL) was added 2.64 M n-butyl lithium/hexane solution (54.8 mL) at an internal temperature of −50° C. or lower, followed by warming to room temperature, stirring for 1 hour, and then cooling to an internal temperature of −60° C. To this reaction mixture was added dropwise the acid anhydride/THF mixture, which had been prepared previously, at an internal temperature of −50° C. or lower, followed by stirring at room temperature for 4 hours. 1 M Sodium hydroxide (600 mL) was added thereto under ice-cooling and the organic solvent was evaporated under reduced pressure, followed by extraction with ethyl acetate/hexane (1/3, 200 mL×3). The organic layer was sequentially washed with a saturated aqueous ammonium chloride solution (200 mL) and saturated brine (200 mL), and dried over anhydrous sodium sulfate, and the solvent was then evaporated under reduced pressure to obtain (4R)-4-benzyl-3-{2-[3-cyclopropyl-4-(cyclopropylsulfonyl)phenyl]-3-[(2R,3R,7R)-2,3-diphenyl-1,4-dioxaspiro[4.4]non-7-yl]propanoyl}-1,3-oxazolidin-2-one (72 g) as a brown oil.

Production Example 26

A mixture of (4R)-4-benzyl-3-{2-[3-cyclopropyl-4-(cyclopropylsulfonyl)phenyl]-3-[(2R,3R,7R)-2,3-diphenyl-1,4-dioxaspiro[4.4]non-7-yl]propanoyl}-1,3-oxazolidin-2-one (70 g), 4 M hydrochloric acid (140 mL), and acetone (560 mL) was stirred under heating and reflux for 2 hours. After leaving it to be cooled at room temperature, saturated aqueous sodium hydrogen carbonate solution/water (1/1, 200 mL) was added thereto, and the organic solvent was evaporated under reduced pressure, followed by extraction with ethyl acetate (200 mL×2). The organic layer was washed with saturated brine (100 mL) and dried over anhydrous sodium sulfate, and the solvent was then evaporated under reduced pressure. The residue was purified by silica gel column chromatography (ethyl acetate:hexane=30:70→50:50) to obtain (4R)-4-benzyl-3-{(2R)-2-[3-cyclopropyl-4-(cyclopropylsulfonyl)phenyl]-3-[(1R)-3-oxocyclopentyl]propanoyl}-1,3-oxazolidin-2-one (21 g) as a colorless amorphous substance.

Production Example 27

A mixture of (4R)-4-benzyl-3-{(2R)-2-[3-cyclopropyl-4-(cyclopropylsulfonyl)phenyl]-3-[(1R)-3-oxocyclopentyl] propanoyl}-1,3-oxazolidin-2-one (25.7 g), 2,2-dimethylpropane-1,3-diol (50 g), pyridinium paratoluenesulfonate (1.32 g), and toluene (205 mL) was stirred under heating and reflux for 6 hours. After leaving it to be cooled at room temperature, saturated aqueous sodium bicarbonate (100 mL) was added thereto and the aqueous layer was extracted with ethyl acetate (100 mL×2). The organic layer was combined, sequentially washed with 1 M aqueous sodium hydroxide solution (50 mL), saturated aqueous ammonium chloride solution (50 mL), and saturated brine (50 mL), and then dried over anhydrous sodium sulfate. The solvent was evaporated under reduced pressure to obtain (4R)-4-benzyl-3-{(2R)-2-[3-cyclopropyl-4-(cyclopropylsulfonyl)phenyl]-3-[(2R)-8,8-dimethyl-6,10-dioxaspiro[4.5]dec-2-yl]propanoyl}-1,3-oxazolidin-2-one (29.8 g) as a colorless amorphous substance.

Production Example 28

To 30% aqueous hydrogen peroxide (20 mL) was added a solution of lithium hydroxide (2.3 g) in water (45 mL) under ice-cooling, and then a solution of (4R)-4-benzyl-3-{(2R)-2-[3-cyclopropyl-4-(cyclopropylsulfonyl)phenyl]-3-[(2R)-8,8-dimethyl-6,10-dioxaspiro[4.5]dec-2-yl]propanoyl}-1,3-oxazolidin-2-one (29.8 g) in THF (240 mL)/water (60 mL) was added dropwise thereto at an internal temperature of 12° C. or lower, followed by stirring for 30 minutes under ice-cooling. To the reaction solution was added an aqueous solution of sodium sulfite (30 g) at an internal temperature of 15° C. or lower, and the organic solvent was evaporated under reduced pressure. To the residue was added concentrated hydrochloric acid under ice-cooling to adjust the pH to 1-2, followed by extraction with ethyl acetate (100 mL×3). The organic layer was sequentially washed with saturated aqueous sodium bicarbonate (50 mL) and saturated brine (50 mL), and then dried over anhydrous sodium sulfate. The solvent was evaporated under reduced pressure to obtain a mixture of (2R)-2-[3-cyclopropyl-4-(cyclopropylsulfonyl)phenyl]-3-[(2R)-8,8-dimethyl-6,10-dioxaspiro[4.5]dec-2-yl]propionic acid (22.1 g) as a colorless oil which was a mixture with (4R)-4-benzyl-1,3-oxazolidin-2-one.

Production Example 29

A mixture of (2R)-2-[3-cyclopropyl-4-(cyclopropylsulfonyl)phenyl]-3-[(2R)-8,8-dimethyl-6,10-dioxaspiro[4.5]dec-2-yl]propionic acid (22 g), 4 M hydrochloric acid (22 mL), and acetone (88 mL) was stirred under heating and reflux for 2 hours. The solvent was evaporated under reduced pressure, and then to the residue were added ethyl acetate/water (1/3, 300 mL) and sodium hydroxide (5.7 g) under ice-cooling. To the aqueous layer was added concentrated hydrochloric acid under ice-cooling to adjust the pH to 1, and chloroform was added thereto. The organic layer was washed with saturated brine and dried over anhydrous sodium sulfate, and the solvent was then evaporated under reduced pressure to obtain (2R)-2-[3-cyclopropyl-4-(cyclopropylsulfonyl)phenyl]-3-[(1R)-3-oxocyclopentyl]propionic acid (17.9 g) as a colorless amorphous substance.

Production Example 30

To a solution of 2-(benzyloxy)ethanol (1.94 g) in DMF (60 mL) was added 60% sodium hydride (510 mg) under ice-cooling, followed by stirring at room temperature for 30 minutes, and methyl 5-chloropyrazine-2-carboxylate (2 g) was added thereto in one portion in an ice bath, followed by stirring at room temperature for 15 minutes. To the reaction mixture was added 1 M hydrochloric acid in an ice bath, followed by extraction with ethyl acetate. The organic layer was washed with saturated brine, dried over anhydrous magnesium sulfate, and then concentrated under reduced pressure. The obtained residue was purified by silica gel column chromatography (hexane:ethyl acetate=3:1-1:1) to obtain a colorless oily substance. To a solution of the obtained colorless oily substance in methanol (50 mL) was added 1 M aqueous sodium hydroxide solution (15 mL) at room temperature, followed by stirring at room temperature for 2 hours. 1 M Hydrochloric acid was added to reaction mixture to adjust the pH to 2 under ice-cooling, followed by addition of water (about 200 mL). The resulting precipitate was collected by filtration while washing with a solvent (water:methanol=5:1), to obtain 5-[2-(benzyloxy)ethoxy]pyrazine-2-carboxylic acid (1.089 g) as a white solid.

Production Example 31

5-[2-(Benzyloxy)ethoxy]pyrazine-2-carboxylic acid (1.089 g) was suspended in tert-butyl alcohol (20 mL), and triethylamine (0.66 mL) and diphenylphosphoryl azide (0.9 mL) were added thereto. The reaction mixture was heated under reflux overnight and left to be cooled to room temperature. To the reaction mixture was added water, followed by extraction with ethyl acetate. The organic layer was sequentially washed with saturated aqueous sodium bicarbonate and saturated brine, and then dried over anhydrous magnesium sulfate. It was concentrated under reduced pressure, and the obtained crude product was purified by silica gel column chromatography (hexane:ethyl acetate=5:1-3:1) to obtain tert-butyl {5-[2-(benzyloxy)ethoxy]pyrazin-2-yl}carbamate (1.352 g) as a white solid.

Production Example 32

To a solution of tert-butyl {5-[2-(benzyloxy)ethoxy]pyrazin-2-yl}carbamate (614 mg) in dichloromethane (10 mL) was added trifluoroacetic acid (0.68 mL) at room temperature, followed by stirring at room temperature overnight. After concentration, saturated aqueous sodium bicarbonate was added thereto. After extraction with ethyl acetate, the organic layer was dried over anhydrous magnesium sulfate. The crude product obtained by concentration was purified by basic silica gel column chromatography (hexane:ethyl acetate=5:1-1:1) to obtain 5-[2-(benzyloxy)ethoxy]pyrazin-2-amine (269 mg) as a pale yellow solid.

Production Example 33

To a solution of methyl 5-aminopyrazine-2-carboxylate (2 g) in dichloromethane (20 mL) were added pyridine (36.4 mL) and allyl chloroformate (25.2 mL) in 4 divided portions respectively, under ice-cooling, followed by stirring at room temperature overnight. To the reaction mixture was added water under ice-cooling, followed by extraction with ethyl acetate. The organic layer was sequentially washed with 1 M hydrochloric acid, saturated aqueous sodium bicarbonate, and saturated brine. The organic layer was dried over anhydrous magnesium sulfate and concentrated. The obtained solid was collected by filtration while washing with a solvent (hexane:ethyl acetate=3:1) to obtain methyl 5-{[(allyloxy)carbonyl]amino}pyrazine-2-carboxylate (481 mg) as a white solid.

Production Example 34

To a solution of methyl 5-{[(allyloxy)carbonyl]amino}pyrazine-2-carboxylate (481 mg) in THF (10 mL) was added 3 M methyl magnesium bromide/THF solution (2.4 mL) under ice-cooling, followed by stirring at the same temperature for 1 hour. To the reaction mixture was added saturated aqueous ammonium chloride solution under ice-cooling, followed by extraction with ethyl acetate. The organic layer was washed with saturated brine and dried over anhydrous magnesium sulfate. The crude product obtained by concentration was purified by silica gel column chromatography (hexane:ethyl acetate=5:1-2:1) to obtain allyl [5-(1-hydroxy-1-methylethyl)pyrazin-2-yl]carbamate (123 mg) as a yellow solid.

Production Example 35

To a solution of formic acid (48 mg) and n-butylamine (76 mg) in THF (10 mL) was added tetrakistriphenylphosphine-palladium (30 mg) and allyl [5-(1-hydroxy-1-methylethyl)pyrazin-2-yl]carbamate (123 mg) at room temperature, followed by stirring at room temperature for 5 hours. To the reaction mixture was added water, saturated aqueous sodium bicarbonate, and saturated brine at room temperature, followed by extraction with a solvent (chloroform:isopropyl alcohol=4:1). The organic layer was dried over anhydrous magnesium sulfate. The crude product obtained by concentration was purified by a thin layer silica gel chromatography (chloroform:methanol=10:1) to obtain 2-(5-aminopyrazin-2-yl)propan-2-ol (51 mg) as a pale yellow oily substance.

Production Example 36

To a solution of N-(5-acetylpyrazin-2-yl)-2,2-dimethyl-propanamide (500 mg) in ethanol (10 mL) and THF (10 mL) was added sodium borohydride (86 mg) under ice-cooling, followed by stirring for 30 minutes under ice-cooling. To the reaction mixture was added 1 M hydrochloric acid under ice-cooling, followed by extraction with ethyl acetate. The organic layer was washed with saturated aqueous sodium bicarbonate and saturated brine, dried over anhydrous magnesium sulfate, and then concentrated to obtain N-[5-(1-hydroxyethyl)pyrazin-2-yl]-2,2-dimethylpropanamide (525 mg) as a brown solid.

Production Example 37

To a solution of N-[5-(1-hydroxyethyl)pyrazin-2-yl]-2,2-dimethylpropanamide (394 mg) in methanol (10 mL) was added potassium carbonate (249 mg) at room temperature, followed by stirring at room temperature overnight and stirring at 60° C. for 5 hours. Further, potassium carbonate (249 mg) was added thereto, followed by stirring at 60° C. for 3 hours. After leaving it to be cooled to room temperature, saturated brine was added to the reaction mixture, followed by extraction with a solvent (chloroform:isopropyl alcohol=4:1). The organic layer was dried over anhydrous magnesium sulfate and concentrated. The obtained solid was collected by filtration while washing with a solvent (hexane:diisopropyl ether=1:1), to obtain 1-(5-aminopyrazin-2-yl)ethanol (187 mg) as a pale yellow solid.

Production Example 38

To a solution of N-(5-acetylpyrazin-2-yl)-2,2-dimethylpropanamide (300 mg) in methanol (10 mL) was added potassium carbonate (750 mg) at room temperature. It was stirred at 60° C. overnight. To the reaction mixture were added saturated aqueous sodium bicarbonate and saturated brine at room temperature, followed by extraction with a solvent (chloroform:isopropyl alcohol=4:1). The organic layer was dried over anhydrous magnesium sulfate and concentrated. The obtained solid was collected by filtration while washing with a solvent (hexane:diisopropyl ether=1:1), to obtain 1-(5-aminopyrazin-2-yl)ethanone (180 mg) as a pale yellow solid.

Production Example 39

To a solution of methyl 5-(2-oxoethyl)pyrazine-2-carboxylate (5.08 g) in methanol (50 mL) was added sodium borohydride (1.07 g) under ice-cooling, followed by stirring at the same temperature for 60 minutes. To the reaction mixture was added 1 M hydrochloric acid under ice-cooling to adjust the pH to 3. Saturated brine was added thereto, followed by extraction with a solvent (ethyl acetate:isopropyl alcohol=4:1). The organic layer was dried over anhydrous magnesium sulfate and concentrated. The obtained crude product was purified by silica gel column chromatography (hexane:ethyl acetate=4:1-0:1, chloroform:methanol=1:0-30:1) to obtain methyl 5-(2-hydroxyethyl)pyrazine-2-carboxylate (1.34 g) as a red-brown oily substance.

Production Example 40

To a solution of methyl 5-(2-hydroxyethyl)pyrazine-2-carboxylate (1.07 g) in dichloromethane (20 mL) were added 3,4-dihydro-2H-pyrane (1.6 mL) and pyridinium p-toluenesulfonate (295 mg) at room temperature, followed by stirring at room temperature overnight. To the reaction mixture was added water, followed by extraction with ethyl acetate. The organic layer was washed with saturated brine and dried over anhydrous magnesium sulfate. The crude product obtained by concentration was purified by silica gel column chromatography (hexane:ethyl acetate=2:1-1:2) to obtain methyl 5-[2-(tetrahydro-2H-pyran-2-yloxy)ethyl]pyrazine-2-carboxylate (1.25 g) as a pale yellow oily substance.

Production Example 41

To a solution of methyl 5-[2-(tetrahydro-2H-pyran-2-yloxy)ethyl]pyrazine-2-carboxylate (1.36 g) in methanol (20 mL) was added 1 M aqueous sodium hydroxide solution (15 mL) under ice-cooling. It was stirred at room temperature for 2 hours. To the reaction mixture was added 1 M hydrochloric acid under ice-cooling to adjust the pH to 3. A saturated brine was added, followed by extraction with a solvent (chloroform:methanol=4:1). The organic layer was dried over anhydrous magnesium sulfate, filtered, and concentrated to obtain 5-[2-(tetrahydro-2H-pyran-2-yloxy)ethyl]pyrazine-2-carboxylic acid (1.50 g) as a brown oily substance.

Production Example 42

To a solution of 5-[2-(tetrahydro-2H-pyran-2-yloxy)ethyl]pyrazine-2-carboxylic acid (1.28 g) in toluene (20 mL) were added triethylamine (0.85 ml) and diphenylphosphoryl azide (1.3 mL) at room temperature, followed by stirring at room temperature for 15 minutes. The reaction solution was warmed to 90° C., followed by stirring for 30 minutes. To the reaction solution was added benzyl alcohol (1.05 mL), followed by reflux for 3 hours. After leaving it to be cooled to room temperature, water was added to the reaction mixture, followed by extraction with ethyl acetate. The organic layer was sequentially washed with saturated aqueous sodium bicarbonate and saturated brine, and dried over anhydrous magnesium sulfate. After filtration and concentration, the obtained crude product was purified by silica gel column chromatography (hexane:ethyl acetate=5:1-2:1). The obtained solid was collected by filtration while washing with a solvent (hexane:diisopropyl ether=5:1), to obtain benzyl {5-[2-(tetrahydro-2H-pyran-2-yloxy)ethyl]pyrazin-2-yl}carbamate (461 mg) as a white solid.

Production Example 43

To a solution of benzyl {5-[2-(tetrahydro-2H-pyran-2-yloxy)ethyl]pyrazin-2-yl}carbamate (416 mg) in methanol (20 mL) and THF (10 mL) was added 10% palladium carbon (100 mg), followed by stirring for 2 hours under a hydrogen atmosphere. It was filtered through Celite and concentrated to obtain 5-[2-(tetrahydro-2H-pyran-2-yloxy)ethyl]pyrazin-2-amine (305 mg) as a pale yellow oily substance.

Production Example 44

To a solution of ethyl 2-[3-cyclopropyl-4-(cyclopropylsulfonyl)phenyl]-3-(tetrahydro-2H-pyran-4-yl)acrylate (2.62 g) in ethanol (24 mL) and THF (12 mL) was added nickel(II) chloride hexahydrate (154 mg) under ice-cooling. Subsequently, sodium borohydride (489 mg) was added thereto under ice-cooling, followed by stirring at room temperature overnight. To the reaction mixture were added 1 M hydrochloric acid and water under ice-cooling. The resulting black solid was removed by filtration through Celite and the filtrate was extracted with ethyl acetate. The organic layer was washed with saturated brine and dried over anhydrous magnesium sulfate. After concentration, ethyl 2-[3-cyclopropyl-4-(cyclopropylsulfonyl)phenyl]-3-(tetrahydro-2H-pyran-4-yl)propionate (2.82 g) was obtained as a colorless oily substance.

Production Example 45

To a mixed solution of lithium aluminum hydride (3.36 g) in THF (215 mL) was added a solution of (2S,3S)-2,3-diphenyl-1,4-dioxaspiro[4.5]decane-8-carboxylate (43.3 g) in THF (215 mL) at an internal temperature of 10° C. or lower over 30 minutes in a methanol-ice bath, followed by stirring at an internal temperature of 10° C. or lower for 1 hour and then stirring in an ice bath for 2 hours. To the reaction mixture were sequentially added water (8.6 mL), 10% aqueous sodium hydroxide solution (8.6 mL), and water (27.5 mL) in an ice bath, followed by stirring at room temperature for 30 minutes. The solid was removed by filtration through Celite and the filtrate was concentrated to obtain [(2S,3S)-2,3-diphenyl-1,4-dioxaspiro[4.5]dec-8-yl]methanol (38.4 g) as a pale peach pink oily substance.

Production Example 46

To a solution of [(2S,3S)-2,3-diphenyl-1,4-dioxaspiro[4.5]dec-8-yl]methanol (47.2 g) in dichloromethane (500 mL) were added triethylamine (25.4 mL) and methanesulfonyl chloride (13.5 mL) at 3° C. or lower over 30 minutes under ice-cooling, followed by stirring for 3 hours under ice-cooling. It was warmed to room temperature, the precipitated solid was filtered through Celite, and the filtrate was concentrated to obtain methyl [(2S,3S)-2,3-diphenyl-1,4-dioxaspiro[4.5]dec-8-yl]methanesulfonate (64.5 g) as a pale peach pink oily substance.

Production Example 47

To a solution of methyl [(2S,3S)-2,3-diphenyl-1,4-dioxaspiro[4.5]dec-8-yl]methanesulfonate (58.6 g) in acetone (800 mL) was added sodium iodide (52.3 g) at room temperature. The mixture was heated under reflux overnight and again cooled to room temperature. To the reaction mixture were added water and ethyl acetate. The organic layer was separated, sequentially washed with saturated aqueous sodium hydrogen carbonate solution and saturated brine, and then dried over anhydrous magnesium sulfate. The crude product obtained by concentration under reduced pressure was purified by silica gel column chromatography (hexane:ethyl acetate=1:0-50:1-30:1-10:1) to obtain (2S,3S)-8-(iodomethyl)-2,3-diphenyl-1,4-dioxaspiro[4.5]decane (40.6 g) as a pale yellow oily substance.

Production Example 48

To a mixture of 60% sodium hydride (2.30 g) and DMF (60.2 mL) was slowly added methyl 2-hydroxy-2-methylpropanoate (6.02 mL) under ice-cooling. Further, 4-(chloromethyl)phenyl methyl ether (7.83 mL) was added thereto, followed by stirring at room temperature for 2 hours. To the reaction mixture was added saturated aqueous ammonium chloride solution, followed by extraction with ethyl acetate. The organic layer was washed with saturated brine and dried over anhydrous sodium sulfate. The solvent was evaporated and the obtained residue was purified by silica gel column chromatography (chloroform:hexane=20:80) to obtain methyl 2-[(4-methoxybenzyl)oxy]-2-methylpropanoate (12.5 g) as a colorless oily substance.

Production Example 49

To a mixture of lithium borohydride (2.29 g) and THF (200 mL) was added dropwise methyl 2-[(4-methoxybenzyl)oxy]-2-methylpropanoate (12.5 g) under ice-cooling, followed by stirring at 60° C. for 2 hours. To the reaction mixture was added water under ice-cooling, followed by extraction with ethyl acetate. The organic layer was washed with saturated brine and dried over anhydrous sodium sulfate. The solvent was evaporated and the obtained residue was purified by silica gel column chromatography (ethyl acetate:hexane=20:80) to obtain 2-[(4-methoxybenzyl)oxy]-2-methylpropan-1-ol (6.72 g) as a colorless oily substance.

Production Example 50

To a solution of 2-[(4-methoxybenzyl)oxy]-2-methylpropan-1-ol (0.30 g) in N-methylpyrrolidone (4.5 mL) was added sodium hydride (63 mg) under ice-cooling, followed by stirring at 60° C. for 30 minutes. To the reaction mixture was added methyl 5-chloropyrazine-2-carboxylate (246 mg), followed by stirring at 120° C. overnight. To the reaction mixture was added 1 M hydrochloric acid for neutralization in an ice bath, followed by extraction with ethyl acetate. The organic layer was washed with saturated brine, dried over anhydrous magnesium sulfate, and then concentrated under reduced pressure. The obtained residue was purified by silica gel column chromatography (hexane:ethyl acetate=80:20) to obtain methyl 5-{2-[(4-methoxybenzyl)oxy]-2-methylpropoxy}pyrazine-2-carboxylate (0.20 g) as a colorless oily substance.

Production Example 51

A mixture of methyl 5-{2-[(4-methoxybenzyl)oxy]-2-methylpropoxy}pyrazine-2-carboxylate (3.5 g), 1 M aqueous sodium hydroxide solution (35 mL), methanol (35 mL), and THF (35 mL) was stirred at room temperature for 1 hour. To the reaction mixture was added water, followed by washing with ethyl acetate. To the aqueous layer was added 1 M hydrochloric acid to adjust the pH to 4, followed by extraction with ethyl acetate. The organic layer was washed with saturated brine and dried over anhydrous sodium sulfate. The solvent was evaporated to obtain 5-{2-[(4-methoxybenzyl)oxy]-2-methylpropoxy}pyrazine-2-carboxylic acid (2.5 g) as a pale yellow solid.

Production Example 52

A mixture of tert-butyl (5-{2-[(4-methoxybenzyl)oxy]-2-methylpropoxy}pyrazin-2-yl)carbamate (330 mg), hydrazine monohydrate (198 µL), potassium hydroxide (1.15 g), and ethylene glycol (9.9 mL) was stirred at 120° C. for 3 hours. To the reaction mixture was added water, followed by extraction with chloroform. The organic layer was washed with saturated brine and dried over anhydrous sodium sulfate. The solvent was evaporated and the obtained residue was purified by silica gel column chromatography (ethyl acetate:hexane=50:50) to obtain 5-{2-[(4-methoxybenzyl)oxy]-2-methylpropoxy}pyrazin-2-amine (220 mg) as a yellow oily substance.

Production Example 53

To a mixture of methyl [3-bromo-4-(cyclopropylsulfonyl)phenyl]acetate (300 mg) and DMF (2 mL) was added sodium hydride (43 mg) under ice-cooling, followed by stirring for 10 minutes. Further, bromomethylbenzene (129 µL) was added thereto under ice-cooling, followed by stirring at room temperature for 2 hours. To the reaction mixture was added saturated aqueous ammonium chloride solution, followed by extraction with ethyl acetate. The organic layer was washed with saturated brine and dried over anhydrous sodium sulfate. The solvent was evaporated and the obtained residue was purified by silica gel column chromatography (ethyl acetate:hexane=20:80) to obtain methyl 2-[3-bromo-4-(cyclopropylsulfonyl)phenyl]-3-phenylpropanotate (217 mg) as a colorless oily substance.

Production Example 54

To a solution of (4R)-4-benzyl-3-{2-[3-cyclopropyl-4-(cyclopropylsulfonyl)phenyl]-3-[(2S,3S)-2,3-diphenyl-1,4-dioxaspiro[4.5]dec-8-yl]propanoyl}-1,3-oxazolidin-2-one (4.8 g) in acetone (48 mL) was added 1 M hydrochloric acid (16 mL), followed by stirring at 50° C. overnight. To the reaction mixture was added water, followed by extraction with ethyl acetate. The organic layer was washed with saturated brine and dried over anhydrous magnesium sulfate. The solvent was evaporated and the obtained residue was purified by silica gel column chromatography (hexane:ethyl acetate=3:1-1:1) to obtain a white amorphous substance (3.54 g). To a solution, which was prepared by adding a solution of lithium hydroxide (30.5 mg) in water (1 mL) to 30% aqueous hydrogen peroxide (150 μL) under ice-cooling, was added dropwise a solution of the obtained white amorphous substance (165 mg) in THF (1.6 mL) under ice-cooling, followed by stirring at 0° C. for 2 hours. To the reaction mixture was added a solution of sodium thiosulfate (0.7 g) in water (5 mL), followed by washing with diethyl ether. To the obtained aqueous layer was added 1 M hydrochloric acid under ice-cooling to adjust the pH to 4, followed by extraction with a solvent (chloroform:isopropyl alcohol=4:1). The obtained organic layer was dried over anhydrous magnesium sulfate. The crude product obtained by concentration was purified by silica gel column chromatography (chloroform:methanol=1:0-10:1) to obtain a mixture (125 mg) of (2R)-2-[3-cyclopropyl-4-(cyclopropylsulfonyl)phenyl]-3-(4-oxocyclohexyl)propanoic acid with (4R)-4-benzyl-1,3-oxazolidin-2-one as a white amorphous substance.

Production Example 55

To a mixture of methyl tetrahydro-2H-thiopyrane-4-carboxylate (2.0 g) and chloroform (20 mL) was added methachloroperbenzoic acid (8.62 g) under ice-cooling, followed by stirring at room temperature for 4 hours. To the reaction mixture was added aqueous sodium sulfite solution under ice-cooling, followed by extraction with ethyl acetate. The organic layer was washed with saturated brine and dried over anhydrous sodium sulfate. The solvent was evaporated and the obtained residue was purified by silica gel column chromatography (ethyl acetate:hexane=50:50) to obtain a white solid (2 g). To a mixture of the above white solid and THF (30 mL) was added lithium borohydride (600 mg) under ice-cooling, followed by stirring at 40° C. for 3 hours. To the reaction mixture was added water under ice-cooling, followed by saturation with ammonium sulfate. After extraction with chloroform/isopropanol, the organic layer was dried over anhydrous sodium sulfate. The solvent was evaporated to obtain a white solid (1.1 g). To a mixture of triphenylphosphine (88 mg), imidazole (25 mg), and dichloromethane (1 mL) was added iodine (85 mg) under ice-cooling, followed by stirring for 10 minutes. Thereafter, the above white solid was added thereto under ice-cooling, followed by stirring at room temperature for 2 hours. To the reaction mixture was added water, followed by extraction with ethyl acetate. The organic layer was washed with saturated brine and dried over anhydrous sodium sulfate. The solvent was evaporated and the obtained residue was purified by silica gel column chromatography (ethyl acetate:hexane=50:50) to obtain 4-(iodomethyl)tetrahydro-2H-thiopyrane-1,1-dioxide (52 mg) as a white solid.

Production Example 56

A mixture of (2R)-2-[3-cyclopropyl-4-(cyclopropylsulfonyl)phenyl]-3-(4-oxocyclohexy)propanoic acid (45 mg), diazomethyltrimethylsilane (2.0 M diethyl ether solution, 0.1 mL), methanol (0.2 mL), and toluene (0.8 mL) was stirred at room temperature for 10 minutes. The solvent was evaporated and the obtained residue was purified by silica gel column chromatography (ethyl acetate:hexane=50:50) to obtain methyl (2R)-2-[3-cyclopropyl-4-(cyclopropylsulfonyl)phenyl]-3-(4-oxocyclohexyl)propanoate (29 mg) as a colorless oil.

Production Example 57

A mixture of methyl (2R)-2-[3-cyclopropyl-4-(cyclopropylsulfonyl)phenyl]-3-(4-oxocyclohexyl)propanoate (178 mg), 2-methoxy-N-(2-methoxyethyl)-N-(trifluoro-$\lambda^4$-sulfanyeethanamine (406 μL), ethanol (5 μL) and dichloromethane (2.7 mL) was stirred at room temperature for 4 hours. To the reaction mixture was added water, followed by extraction with ethyl acetate. The organic layer was washed with saturated brine and dried over anhydrous sodium sulfate. The solvent was evaporated and the residue was purified by silica gel column chromatography (ethyl acetate:hexane=30:70) to obtain methyl (2R)-2-[3-cyclopropyl-4-(cyclopropylsulfonyl)phenyl]-3-(4,4-difluorocyclohexyl)propanoate (85 mg) as a colorless oily substance.

Production Example 58

A mixture of (5-aminopyrazin-2-yl)methyl acetate (1 g), potassium carbonate (83 mg), and methanol (15.1 mL) was heated under reflux for 2 hours. The solvent was evaporated to obtain a pale yellow solid (740 mg). A mixture of the above pale yellow solid, tert-butyl(chloro)dimethylsilane (1.34 g), imidazole (805 mg) and DMF (10 mL) was stirred at room temperature overnight. To the reaction mixture was added water, followed by extraction with ethyl acetate. The organic layer was washed with saturated brine and dried over anhydrous sodium sulfate. The solvent was evaporated and the obtained residue was purified by silica gel column chromatography (ethyl acetate:hexane=10:90) to obtain 5-({[tert-butyl(dimethyl)silyl]oxy}methyl)pyrazin-2-amine (805 mg) as a white solid.

Production Example 59

To a solution of ethyl 2-(2-{[(allyloxy)carbonyl]amino}-1,3-thiazol-4-yl)-2-hydroxypropionate (2.75 g) in 1,4-dioxane (25 mL) was added sodium borohydride (0.962 g) under ice-cooling. Further, water (0.5 mL) was added thereto at room temperature, followed by stirring at room temperature for 2 hours. Concentrated hydrochloric acid (8 mL) was added thereto at an internal temperature of 20° C. or lower under ice-cooling, followed by concentration. A white solid was separated by filtration while washing the obtained residue with methanol. The obtained white solid was dissolved in pyridine (15 mL), and acetic anhydride (2.59 mL) was added thereto at room temperature, followed by stirring for 2.5 hours. To the reaction mixture was added water at room temperature, followed by extraction with ethyl acetate. The organic layer was sequentially washed with 1 M hydrochloric acid, saturated aqueous sodium bicarbonate, and saturated brine, and then dried over anhydrous magnesium sulfate. After concentration, 2-(2-{[(allyloxy)carbonyl]amino}-1,3-thiazol-4-yl)-2-hydroxypropyl acetate (2.71 g) was obtained as a pale yellow oily substance.

Production Example 60

To a solution of 2-(2-{[(allyloxy)carbonyl]amino}-1,3-thiazol-4-yl)-2-hydroxypropyl acetate (790 mg) in THF (10 mL) were added n-butylamine (0.52 mL), formic acid (0.20 mL), and tetrakistriphenylphosphine palladium (33 mg) at room temperature, followed by stirring at room temperature for 30 minutes. To the reaction mixture was added 1 M hydrochloric acid (30 mL) at room temperature, followed by extraction with ethyl acetate. The aqueous layer was adjusted to pH 9 using saturated aqueous sodium bicarbonate, followed by extraction with a solvent (ethyl acetate:isopropyl alcohol=3:1, 100 mL×3). The organic layer was washed with saturated brine and dried over anhydrous magnesium sulfate. After concentration, 2-(2-amino-1,3-thiazol-4-yl)-2-hydroxypropyl acetate (261 mg) was obtained as a pale yellow oily substance. The obtained pale yellow oily substance was subjected to optical resolution with chiral column chromatography (Product Name: Chiralcel OJ-H, hexane:ethanol:diethylamine=30:70:0.1) to obtain optical active products of 2-(2-amino-1,3-thiazol-4-yl)-2-hydroxypropyl acetate at a first peak and a second peak in yields of 37% and 25%, respectively (>95% ee) (absolute arrangement was not determined).

Production Example compounds 61 to 100 were prepared in the same manner as the methods of Production Examples 1 to 60. The structures of Production Example compounds are shown in Tables 5 to 23 below, and the preparation methods and the physicochemical data are shown in Tables 24 to 27 below.

Example 1

To a solution of triphenylphosphine (320 mg) in dichloromethane (10 mL) was added N-bromosuccinimide (217 mg) under ice-cooling, followed by stirring for 15 minutes under ice-cooling. A solution of (2E)-3-cyclopentyl-2-[3-cyclopropyl-4-(cyclopropylsulfonyl)phenyl]acrylic acid (200 mg) in dichloromethane (5 mL) was added thereto under ice-cooling, followed by stirring at room temperature for 0.5 hour. A solution of 1-[3-(benzyloxy)propyl]-1H-pyrazol-3-amine (141 mg) in dichloromethane (5 mL) and pyridine (0.09 mL) were added thereto at room temperature, followed by stirring at room temperature overnight. To the reaction mixture was added water, followed by extraction with ethyl acetate. The organic layer was sequentially washed with 1 M hydrochloric acid, saturated aqueous sodium bicarbonate, and saturated brine, and dried over anhydrous magnesium sulfate. The crude product obtained by concentration was purified by silica gel column chromatography (hexane:ethyl acetate=3:1-1:1). To a solution of the obtained colorless oily substance in trifluoroacetic acid (5 mL) was added 1,2,3,4,5-pentamethylbenzene (823 mg) at room temperature, followed by stirring at room temperature for 48 hours. To a solution of the oily substance obtained by concentration in methanol (4 mL) was added a 1 M aqueous sodium hydroxide solution (1 mL) at room temperature, followed by stirring at room temperature for 30 minutes. Saturated brine was added thereto, followed by extraction with chloroform. The organic layer was dried over anhydrous magnesium sulfate and concentrated. The obtained crude product was purified by silica gel column chromatography (hexane:ethyl acetate=2:1, chloroform:methanol=1:0-20:1) to obtain (2E)-3-cyclopentyl-2-[3-cyclopropyl-4-(cyclopropylsulfonyl)phenyl]-N-[1-(3-hydroxypropyl)-1H-pyrazol-3-yl]acrylamide (155 mg) as a white amorphous substance.

Example 2

To a solution of triphenylphosphine (131 mg) in dichloromethane (2 mL) was added N-bromosuccinimide (89 mg) under ice-cooling, followed by stirring for 15 minutes under ice-cooling. A solution of (2E)-2-[3-cyclopropyl-4-(cyclopropylsulfonyl)phenyl]-3-(tetrahydro-2H-pyran-4-yl)acrylic acid (100 mg) in dichloromethane (1 mL) was added thereto, followed by stirring at room temperature for 30 minutes. A solution of 1-methyl-1H-pyrazol-3-amine (39 mg) in dichloromethane (1 mL) and pyridine (0.086 mL) were added thereto at room temperature, followed by stirring at room temperature for 15 hours. To the reaction mixture was added water, followed by extraction with ethyl acetate. The organic layer was sequentially washed with 1 M hydrochloric acid, a saturated aqueous sodium hydrogen carbonate solution, and saturated brine, and dried over anhydrous magnesium sulfate. The crude product obtained by concentration was purified by silica gel column chromatography to obtain (2E)-2-[3-cyclopropyl-4-(cyclopropylsulfonyl)phenyl]-N-(1-methyl-1H-pyrazol-3-yl)-3-(tetrahydro-2H-pyran-4-yl)acrylamide (97 mg).

Example 3

To a solution of triphenylphosphine (320 mg) in dichloromethane (10 mL) was added N-bromosuccinimide (217 mg) under ice-cooling, followed by stirring for 15 minutes under ice-cooling. A solution of (2E)-3-cyclopentyl-2-[3-cyclopropyl-4-(cyclopropylsulfonyl)phenyl]acrylic acid (200 mg) in dichloromethane (10 mL) was added thereto under ice-cooling, followed by stirring at room temperature for 0.5 hour. A solution of 1-{[(4S)-2,2-dimethyl-1,3-dioxolan-4-yl]methyl}-1H-pyrazol-3-amine (142 mg) in dichloromethane (5 mL) and pyridine (0.09 mL) were added thereto at room temperature, followed by stirring at room temperature overnight. Water was added thereto, followed by extraction with ethyl acetate. The organic layer was sequentially washed with 1 M hydrochloric acid, saturated aqueous sodium bicarbonate, and saturated brine, and dried over anhydrous magnesium sulfate. The crude product obtained by concentration was purified by silica gel column chromatography (hexane:ethyl acetate=2:1-1:2). To a solution of the obtained oily substance in THF (15 mL) was added 1 M hydrochloric acid (15 mL), followed by stirring overnight. Saturated brine was added thereto, followed by extraction with a solvent (chloroform:isopropyl alcohol=4:1). The organic layer was dried over anhydrous magnesium sulfate and concentrated. The obtained crude product was purified by silica gel column chromatography (chloroform:methanol=1:0-20:1) to obtain (2E)-3-cyclopentyl-2-[3-cyclopropyl-4-(cyclopropylsulfonyl)phenyl]-N-{1-[(2S)-2,3-dihydroxypropyl]-1H-pyrazol-3-yl}acrylamide (197 mg) as a white amorphous substance.

Example 4

To a solution of triphenylphosphine (84.2 g) in dichloromethane (1.94 L) was added N-bromosuccinimide (56.7 g) in 5 divided portions under ice-cooling (at an internal temperature of 10° C. or lower), followed by stirring for 15 minutes under ice-cooling. A solution of (2E)-2-[3-cyclopropyl-4-(cyclopropylsulfonyl)phenyl]-3-[(2R,3R,7S)-2,3-diphenyl-1,4-dioxaspiro[4.4]non-7-yl]acrylic acid (81 g) in dichloromethane (486 ml) was added dropwise thereto under ice-cooling and warmed to room temperature, followed by stirring for 0.5 hour. A solution of 1-methyl-1H-pyrazol-3-amine (16.5 g) in dichloromethane (10 mL) was added thereto at room temperature, followed by adding pyridine (24.3 mL) and stirring at room temperature for 45 minutes. A saturated aqueous sodium hydrogen carbonate solution (400 ml) was added thereto to stop the reaction. The organic layer was separated, and the organic layer was washed with water and saturated brine, and then dried over anhydrous sodium sulfate. The solvent was evaporated under reduced pressure and the obtained residue was purified by silica gel column chromatography. After concentration, to the residue was added hexane-ethyl acetate mixed solvent (1:1) to separate the precipitated triphenylphosphine oxide partially by filtration, and the solid was washed with hexane-ethyl acetate mixed solvent (1:1). The filtrate was combined and concentrated under reduced pressure to obtain (2E)-2-[3-cyclopropyl-4-(cyclopropylsulfonyl)phenyl]-3-[(2R,3R,7S)-2,3-diphenyl-1,4-dioxaspiro[4.4]non-7-yl]-N-(1-methyl-1H-pyrazol-3-yl)acrylamide as a mixture with triphenylphosphine oxide. To a solution of the obtained mixture (112.4 g) in dioxane (439 mL) was added 4 M hydrochloric acid (439 mL), followed by heating in an oil bath at 50° C. and stirring for 30 minutes, and then leaving it to be cooled at room temperature. The solvent was evaporated under reduced pressure, followed by addition of chloroform, and the organic layer was then separated. The aqueous layer was neutralized and then extracted with chloroform again. The organic layer was combined and washed with water, saturated aqueous sodium hydrogen carbonate solution, and saturated brine, and then dried over anhydrous sodium sulfate. The solvent was evaporated under reduced pressure and the residue was purified by silica gel column chromatography to obtain (2E)-2-[3-cyclopropyl-4-(cyclopropylsulfonyl)phenyl]-N-(1-methyl-1H-pyrazol-3-yl)-3-[(1S)-3-oxocyclopentyl]acrylamide (40.3 g, Example 4-1). Further, (2Z)-2-[3-cyclopropyl-4-(cyclopropylsulfonyl)phenyl]-N-(1-methyl-1H-pyrazol-3-yl)-3-[(1S)-3-oxocyclopentyl]acrylamide (0.17 g, Example 4-2) was obtained as a side product.

Example 5

To a solution of 6-({(2E)-2-[3-cyclopropyl-4-(cyclopropylsulfonyl)phenyl]-3-[(2R,3R,7S)-2,3-diphenyl-1,4-dioxaspiro[4.4]non-7-yl]prop-2-enoyl}amino)nicotinic acid (194 mg) in 1,4-dioxane (4 mL) was added 4 M hydrochloric acid (4 mL), followed by stirring at 50° C. for 2 hours. After leaving it to be cooled to room temperature, saturated brine was added thereto. After extraction with chloroform, the organic layer was dried over anhydrous magnesium sulfate. The crude product obtained by concentration was dissolved in ethyl acetate (4 mL), and 4 M hydrogen chloride/ethyl acetate (1 mL) was added thereto. It was stirred at room temperature for 30 minutes and concentrated. The obtained oily substance was solidified with diisopropyl ether and collected by filtration to obtain 6-({(2E)-2-[3-cyclopropyl-4-(cyclopropylsulfonyl)phenyl]-3-[(1S)-3-oxocyclopentyl]prop-2-enoyl}amino)nicotinic acid monohydrochloride (87 mg) as a white solid.

Example 6

To a solution of (5-{[(2E)-2-[3-cyclopropyl-4-(cyclopropylsulfonyl)phenyl]-3-(3-oxocyclopentyl)prope-2-noyl]amino}pyrazin-2-yl)methyl acetate (0.2065 g) in methanol (6 mL) was added 1 M sodium hydroxide (2 mL), followed by stirring at room temperature for 1 hour. The liquid was neutralized, followed by extraction with chloroform. The organic layer was washed with saturated brine and dried over anhydrous magnesium sulfate. The crude product obtained by concentration under reduced pressure was purified by preparative TLC (chloroform:methanol=10:1) to obtain (2E)-2-[3-cyclopropyl-4-(cyclopropylsulfonyl)phenyl]-N-[5-(hydroxymethyl)pyrazin-2-yl]-3-(3-oxocyclopentyl)acrylamide (40.6 mg) as a white amorphous substance.

Example 7

To a solution of triphenylphosphine (600 mg) in dichloromethane (10 mL) was added N-bromosuccinimide (400 mg) under ice-cooling (at an internal temperature of 5° C. or lower), followed by stirring for 15 minutes, and then a solution of (2E)-2-[3-cyclopropyl-4-(cyclopropylsulfonyl)phenyl]-3-[(2R,3R,7S)-2,3-diphenyl-1,4-dioxaspiro[4.4]non-7-yl]acrylic acid (600 mg) in dichloromethane (10 mL) was added thereto under ice-cooling, followed by stirring at room temperature for 20 minutes. To the reaction mixture were added a mixture of ethyl 2-[(2-amino[1,3]thiazolo[5,4-b]pyridin-5-yl)oxy]acetate (270 mg) in dichloromethane (10 mL) and pyridine (0.17 mL), followed by stirring at room temperature overnight. A saturated sodium bicarbonate solution and dichloromethane were added thereto, and the organic layer was sequentially washed with 1 M hydrochloric acid and saturated brine, and then dried over anhydrous magnesium sulfate. The solvent was evaporated under reduced pressure, and the residue thus obtained was purified by silica gel column chromatography (hexane/ethyl acetate). To the obtained colorless amorphous in THF (3 mL)-methanol (3 mL) mixed solution was added 1 M aqueous sodium hydroxide solution (0.6 mL), followed by stirring at room temperature for 30 minutes. The solvent was evaporated under reduced pressure, followed by addition of 1 M hydrochloric acid and ethyl acetate, and the organic layer was sequentially washed with saturated aqueous sodium bicarbonate and saturated brine, and dried over anhydrous magnesium sulfate. The solvent was evaporated under reduced pressure, and the residue thus obtained was purified by silica gel column chromatography (hexane/ethyl acetate). To a solution of the obtained colorless amorphous in dioxane (5 mL) was added 4 M hydrochloric acid (2 mL), followed by stirring at 50° C. for 3 hours and leaving it to be cooled at room temperature. The solvent was evaporated under reduced pressure, followed by addition of water and ethyl acetate and the organic layer was sequentially washed with saturated aqueous sodium bicarbonate and saturated brine, and dried over anhydrous magnesium sulfate. The solvent was evaporated under reduced pressure, and the residue thus obtained was purified by silica gel column chromatography (hexane/ethyl acetate) to obtain (2E)-2-[3-cyclopropyl-4-(cyclopropylsulfonyl)phenyl]-N-[5-(2-hydroxyethoxy)[1,3]thiazolo[5,4-b]pyridin-2-yl]-3-[(1S)-3-oxocyclopentyl]acrylamide (89 mg) as a colorless amorphous substance.

Example 8

To a solution of (2E)-2-[3-cyclopropyl-4-(cyclopropylsulfonyl)phenyl]-3-[(1S)-3-hydroxycyclopentyl]-N-(1-methyl-1H-pyrazol-3-yl)acrylamide (124 mg) in dichloromethane (4 ml) was added diethylaminosulfur trifluoride (100 µl) under ice-cooling, followed by stirring at room temperature for 15 minutes. The reaction mixture was diluted with dichloromethane, and water was added thereto. The organic layer was sequentially washed with saturated aqueous sodium bicarbonate and saturated brine, and dried over anhydrous magnesium sulfate. After concentrating under reduced pressure, the obtained residue was purified by silica gel column chromatography (ethyl acetate:hexane=7:3-1:0) to obtain (2E)-2-[3-cyclopropyl-4-(cyclopropylsulfonyl)phenyl]-3-[(1S)-3-fluorocyclopentyl]-N-(1-methyl-1H-pyrazol-3-yl)acrylamide (78 mg) as a colorless amorphous substance.

Example 9

To a solution of (2R)-2-[3-cyclopropyl-4-(cyclopropylsulfonyl)phenyl]-3-(tetrahydro-2H-pyran-4-yl)propionic acid (200 mg) in dichloromethane (5 mL) was added sequentially a solution of oxalyl chloride in 1 M dichloromethane (0.64 mL) and DMF (16 µL), followed by stirring for 1 hour under ice-cooling. Thereafter, a solution of 5-methylpyridin-2-amine (63 mg) in dichloromethane (5 mL) and pyridine (0.09 mL) were added thereto under ice-cooling, followed by stirring for 2 hours under ice-cooling. To the reaction mixture was added water under ice-cooling, followed by extraction with ethyl acetate. The organic layer was sequentially washed with a 5% aqueous citric acid solution, saturated aqueous sodium bicarbonate, and saturated brine, and dried over anhydrous magnesium sulfate. The oily substance obtained by concentration was purified by silica gel column chromatography (wetting with hexane:ethyl acetate=1:1, chloroform:methanol=1:0-10:1). The obtained oily substance was dissolved in ethyl acetate (4 mL), and 4 M hydrogen chloride/ethyl acetate (1 mL) was added thereto, followed by stirring at room temperature for 30 minutes. The oily substance obtained by concentration was solidified with diisopropyl ether and collected by filtration to obtain (2R)-2-[3-cyclopropyl-4-(cyclopropylsulfonyl)phenyl]-N-(5-methylpyridin-2-yl)-3-[(1R)-3-oxocyclopentyl]propanamide monohydrochloride (210 mg) as a white solid.

Example 10

To a solution of (2R)-2-[3-cyclopropyl-4-(cyclopropylsulfonyl)phenyl]-3-[(1R)-3-oxocyclopentyl]propanoic acid (99 mg) in dichloromethane (2.0 mL) were added oxalyl chloride (27 µL) and DMF (3 µL) under ice-cooling, followed by stirring for 10 minutes. Thereafter, pyridine (28 µL) and 5-{2-[(4-methoxybenzyl)oxy]-2-methylpropoxy}pyrazin-2-amide (53 mg) were added thereto under ice-cooling, followed by stirring for 20 minutes. To the reaction mixture was added water, followed by extraction with ethyl acetate. The organic layer was washed with saturated brine and dried over anhydrous sodium sulfate. The solvent was evaporated and the obtained residue was purified by silica gel column chromatography (hexane:ethyl acetate=3:1-1:1) to obtain (2R)-2-[3-cyclopropyl-4-(cyclopropylsulfonyl)phenyl]-N-(5-{2-[(4-methoxybenzyl)oxy]-2-methylpropoxy}pyrazin-2-yl)-3-[(1R)-3-oxocyclopentyl]propanamide (82 mg) as a white amorphous substance. A mixture of (2R)-2-[3-cyclopropyl-4-(cyclopropylsulfonyl)phenyl]-N-(5-{2-[(4-methoxybenzyl)oxy]-2-methylpropoxy}pyrazin-2-yl)-3-[(1R)-3-oxocyclopentyl]propanamide (82 mg), 2,3-dichloro-5,6-dicyano-1,4-benzoquinone (56 mg), dichloromethane (7.5 mL), and water (0.38 mL) was stirred at room temperature for 10 minutes. To the reaction mixture was added water, followed by extraction with chloroform. The organic layer was dried over anhydrous sodium sulfate. The solvent was evaporated and the obtained residue was purified by silica gel column chromatography (ethyl acetate:hexane=80:20). The obtained residue was sonicated with diethyl ether and the resulting precipitate was collected by filtration to obtain (2R)-2-[3-cyclopropyl-4-(cyclopropylsulfonyl)phenyl]-N-[5-(2-hydroxy-2-methylpropoxy)pyrazin-2-yl]-3-[(1R)-3-oxocyclopentyl]propanamide (52 mg) as a white solid.

Example 11

To a solution of (2R)-2-[3-cyclopropyl-4-(cyclopropylsulfonyl)phenyl]-3-[(1R)-3-oxocyclopentyl]propionic acid (120 mg) in dichloromethane (5 mL) was sequentially added a solution of 0.5 M oxalyl chloride in dichloromethane (0.77 mL) and DMF (10 μL) under ice-cooling, followed by stirring under ice-cooling for 1 hour. Thereafter, 5-[2-(benzyloxy)ethoxy]pyrazin-2-amine (86 mg) and pyridine (0.05 mL) were added thereto under ice-cooling, followed by stirring for 2 hours under ice-cooling. To the reaction mixture was added water under ice-cooling, followed by extraction with ethyl acetate. The organic layer was sequentially washed with 1 M hydrochloric acid, saturated aqueous sodium bicarbonate, and saturated brine, and then dried over anhydrous magnesium sulfate. The oily substance obtained by concentration was purified by silica gel column chromatography (hexane:ethyl acetate=5:1-1:1) to obtain (2R)—N-{5-[2-(benzyloxy)ethoxy]pyrazin-2-yl}-2-[3-cyclopropyl-4-(cyclopropylsulfonyl)phenyl]-3-[(1R)-3-oxocyclopentyl]propanamide (175 mg) as a pale yellow amorphous substance. To a solution of the obtained (2R)—N-{5-[2-(benzyloxy)ethoxy]pyrazin-2-yl}-2-[3-cyclopropyl-4-(cyclopropylsulfonyl)phenyl]-3-[(1R)-3-oxocyclopentyl]propanamide (175 mg) in methanol (10 mL) was added 10% palladium carbon (50 mg). Under a hydrogen atmosphere, it was stirred at room temperature at 4 atm for 7 hours. The reaction mixture was filtered through Celite and concentrated. To a solution of the obtained oily substance in THF (10 mL) was added 1 M hydrochloric acid (10 mL) at room temperature, followed by stirring at room temperature for 30 minutes. The reaction mixture was extracted with ethyl acetate. The organic layer was sequentially washed with saturated aqueous sodium bicarbonate and saturated brine, and dried over anhydrous magnesium sulfate. The oily substance obtained by concentration was purified by silica gel column chromatography (wetting with hexane:ethyl acetate=1:1, chloroform:methanol=1:0-10:1) to obtain (2R)-2-[3-cyclopropyl-4-(cyclopropylsulfonyl)phenyl]-N-[5-(2-hydroxyethoxy)pyrazin-2-yl]-3-[(1R)-3-oxocyclopentyl]propanamide (103 mg) as a pale yellow amorphous substance.

Example 12

To a solution of (2R)-2-[3-cyclopropyl-4-(cyclopropylsulfonyl)phenyl]-3-[(1R)-3-oxocyclopentyl]propionic acid (110 mg) in dichloromethane (3 mL) were added sequentially oxalyl chloride (0.03 mL) and a catalytic amount of DMF under ice-cooling, followed by stirring for 1 hour, and then ethyl (6-aminopyridin-3-yl)acetate (58 mg) and pyridine (0.05 mL) were added thereto under ice-cooling, followed by stirring for 2 hours. To the reaction mixture were added water and ethyl acetate. The organic layer was sequentially washed with water, saturated aqueous sodium bicarbonate, and saturated brine, and dried over anhydrous magnesium sulfate, and the solvent was then evaporated under reduced pressure. The residue was purified by silica gel column chromatography (hexane/ethyl acetate) to obtain ethyl [6-({(2R)-2-[3-cyclopropyl-4-(cyclopropylsulfonyl)phenyl]-3-[(1R)-3-oxocyclopentyl]propanoyl}amino)pyridin-3-yl]acetate (57 mg) as a pale yellow amorphous substance. To a solution of the obtained ethyl [6-({(2R)-2-[3-cyclopropyl-4-(cyclopropylsulfonyl)phenyl]-3-[(1R)-3-oxocyclopentyl]propanoyl}amino)pyridin-3-yl]acetate (57 mg) in THF (3 mL) was added 1 M aqueous sodium hydroxide solution (0.22 mL), and further added a drop of ethanol, followed by stirring at room temperature overnight. To the reaction solution was added 1 M hydrochloric acid (0.22 mL) to adjust the pH to 4, followed by dilution with saturated brine and dichloromethane for liquid separation. The organic layer was dried over anhydrous magnesium sulfate and the solvent was then evaporated under reduced pressure. To a solution of the residue in ethyl acetate (3 mL) was added a 4 M hydrogen chloride/ethyl acetate solution (0.07 mL) under ice-cooling, followed by stirring for 10 minutes under ice-cooling, and the solvent was then evaporated under reduced pressure. To the residue was added ethyl acetate (3 mL), and the precipitate was collected by filtration and dried under reduced pressure to obtain [6-({(2R)-2-[3-cyclopropyl-4-(cyclopropylsulfonyl)phenyl]-3-[(1R)-3-oxocyclopentyl]propanoyl}amino)pyridin-3-yl]acetic acid hydrochloride (30 mg) as a colorless solid.

Example 13

To a solution of (5-{[(2R)-2-[3-cyclopropyl-4-(cyclopropylsulfonyl)phenyl]-3-(tetrahydro-2H-pyran-4-yl)propanoyl]amino}pyrazin-2-yl)methyl acetate (120 mg) in methanol (4 mL) was added 1 M aqueous sodium hydroxide solution (1 mL) at room temperature, followed by stirring at room temperature for 2 hours. 1 M Hydrochloric acid was added to adjust the pH to 3, followed by extraction with ethyl acetate. The organic layer was washed with saturated aqueous sodium bicarbonate and saturated brine, and dried over anhydrous magnesium sulfate. The crude product obtained by concentration was purified by silica gel column chromatography (wetting with hexane:ethyl acetate=1:1, chloroform:methanol=1:0-10:1) to obtain (2R)-2-[3-cyclopropyl-4-(cyclopropylsulfonyl)phenyl]-N-[5-(hydroxymethyl)pyrazin-2-yl]-3-(tetrahydro-2H-pyran-4-yl)propanamide (93 mg) as a white amorphous substance.

Example 14

A mixture of (2R)-2-[3-cyclopropyl-4-(cyclopropylsulfonyl)phenyl]-3-(tetrahydro-2H-pyran-4-yl)-N-{5-[2-(tetrahydro-2H-pyran-2-yloxy)ethyl]pyrazin-2-yl}propanamide (118 mg) in THF (10 mL) was added 1 M hydrochloric acid (10 mL) at room temperature, followed by stirring for 2 hours. To the reaction mixture was added water, followed by extraction with ethyl acetate. The organic layer was sequentially washed with saturated aqueous sodium bicarbonate and saturated brine, and dried over anhydrous magnesium sulfate. After concentration, the obtained crude product was purified by silica gel column chromatography (wetting with hexane:ethyl acetate=1:1, chloroform:methanol=1:0-10:1) to obtain (2R)-2-[3-cyclopropyl-4-(cyclopropylsulfonyl)phenyl]-N-[5-(2-hydroxyethyl)pyrazin-2-yl]-3-(tetrahydro-2H-pyran-4-yl)propanamide (94 mg) as a white amorphous substance.

Example 15

To a solution of (2R)-2-[3-cyclopropyl-4-(cyclopropylsulfonyl)phenyl]-3-[(1R)-3-oxocyclopentyl]propanoic acid (252 mg) in dichloromethane (2.5 mL) were added oxalyl chloride (68 μL) and DMF (104 μL) under ice-cooling, followed by stirring for 20 minutes. Thereafter, pyridine (65 μL) and 5-({[tert-butyl(dimethyl)silyl]oxy}methyl)pyrazin-2-amine (240 mg) were added thereto under ice-cooling, followed by stirring for 20 minutes under ice-cooling. To the reaction mixture was added water, followed by extraction with ethyl acetate. The organic layer was washed with saturated brine and dried over anhydrous sodium sulfate. The solvent was evaporated and the obtained residue was purified by silica gel column chromatography (ethyl acetate:chloroform=20:80). Further, it was purified by preparative TLC using the same solvent system to obtain a white amorphous substance (200 mg). A mixture of the obtained amorphous substance, 2 M hydrochloric acid (1 mL), and THF (1 mL) was stirred at room temperature for 2 hours. To the reaction mixture was added water, followed by extraction with ethyl acetate. The organic layer was washed with saturated brine and dried over anhydrous sodium sulfate. The solvent was evaporated and the obtained residue was purified by silica gel column chromatography (ethyl acetate:hexane=50:50) to obtain (2R)-2-[3-cyclopropyl-4-(cyclopropylsulfonyl)phenyl]-N-[5-(hydroxymethyl)pyrazin-2-yl]-3-[(1R)-3-oxocyclopentyl]propanamide (136 mg) as a white amorphous substance.

Example 16

To a solution of triphenylphosphine (300 mg) in dichloromethane (4 mL) was added N-bromosuccinimide (200 mg) under ice-cooling, followed by stirring for 15 minutes under ice-cooling, and a solution of (2E)-2-[3-cyclopropyl-4-(cyclopropylsulfonyl)phenyl]-3-[(2R,3R,7S)-2,3-diphenyl-1,4-dioxaspiro[4.4]non-7-yl]acrylic acid (300 mg) in dichloromethane (3 mL) was then slowly added thereto, followed by stirring at room temperature for 30 minutes. To the reaction mixture was added a solution of tert-butyl 3-amino-1H-pyrazole-1-carboxylate (190 mg) in dichloromethane (3 mL), and further added pyridine (0.1 mL), followed by stirring at room temperature for 3 hours. To the reaction mixture were added water (20 mL) and dichloromethane (20 mL), and the organic layer was sequentially washed with 1 M hydrochloric acid (20 mL) and saturated brine (20 mL), and dried over anhydrous magnesium sulfate, and the solvent was then evaporated under reduced pressure. The residue was purified by silica gel column chromatography (hexane:ethyl acetate=75:25→60:40) to obtain tert-butyl 3-({(2E)-2-[3-cyclopropyl-4-(cyclopropylsulfonyl)phenyl]-3-[(2R,3R,7S)-2,3-diphenyl-1,4-dioxaspiro[4.4]non-7-yl] prop-2-enoyl}amino)-1H-pyrazole-1-carboxylate (338 mg) as a colorless amorphous substance. To a solution of tert-butyl 3-({(2E)-2-[3-cyclopropyl-4-(cyclopropylsulfonyl)phenyl]-3-[(2R,3R,7S)-2,3-diphenyl-1,4-dioxaspiro[4.4]non-7-yl]prop-2-enoyl}amino)-1H-pyrazole-1-carboxylate (330 mg) in 1,4-dioxane (3 mL) was added 4 M hydrochloric acid (3 mL), followed by stirring at 50° C. for 3 hours. After leaving it to be cooled at room temperature, 1 M sodium hydroxide (12 mL), saturated brine (20 mL), and dichloromethane (20 mL) were added thereto, the organic layer was dried over anhydrous magnesium sulfate, and the solvent was then evaporated under reduced pressure. To a solution of the residue in ethyl acetate (3 mL) was added 4 M hydrogen chloride/ethyl acetate (0.3 mL), followed by stirring at room temperature for a while, and the solvent was then evaporated under reduced pressure. The obtained colorless solid was purified by silica gel column chromatography (ethyl acetate→chloroform→chloroform/methanol (95/5)) and again purified by silica gel column chromatography (ethyl acetate/methanol 100/0→90/10) to obtain (2E)-2-[3-cyclopropyl-4-(cyclopropylsulfonyl)phenyl]-3-[(1S)-3-oxocyclopentyl]-N-1H-pyrazol-3-yl acrylamide (100 mg) as a colorless amorphous substance.

Example 17

To a solution of (2R)-2-[3-cyclopropyl-4-(cyclopropylsulfonyl)phenyl]-3-[(1R)-3-oxocyclopentyl]propionic acid (160 mg) in dichloromethane (5 mL) were added oxalyl chloride (0.04 mL) and a drop of DMF under ice-cooling, followed by stirring for 1 hour under ice-cooling. To the reaction mixture were sequentially added pyridine (0.04 mL) and tert-butyl 3-amino-1H-pyrazole-1-carboxylate (90 mg), followed by stirring at room temperature overnight. To the reaction mixture were added ethyl acetate (30 mL) and 1 M hydrochloric acid (30 mL), and the organic layer was sequentially washed with saturated aqueous sodium bicarbonate (30 mL) and saturated brine (30 mL). After drying over anhydrous magnesium sulfate, the solvent was then evaporated under reduced pressure to obtain tert-butyl 3-({(2R)-2-[3-cyclopropyl-4-(cyclopropylsulfonyl)phenyl]-3-[(1R)-3-oxocyclopentyl]propanoyl}amino)-1H-pyrazole-1-carboxylate (197 mg) as a pale yellow amorphous substance. To a solution of tert-butyl 3-({(2R)-2-[3-cyclopropyl-4-(cyclopropylsulfonyl)phenyl]-3-[(1R)-3-oxocyclopentyl]propanoyl}amino)-1H-pyrazole-1-carboxylate (190 mg) in ethyl acetate (5 mL) was added 4 M hydrogen chloride/ethyl acetate (5 mL) under ice-cooling, followed by stirring at room temperature overnight. The solvent was evaporated under reduced pressure, ethyl acetate (20 mL) and saturated aqueous sodium bicarbonate (20 mL) were added thereto, and the organic layer was washed with saturated brine (20 mL) and dried over anhydrous magnesium sulfate. The solvent was evaporated under reduced pressure, and the residue was then purified by silica gel column chromatography (ethyl acetate) to obtain (2R)-2-[3-cyclopropyl-4-(cyclopropylsulfonyl)phenyl]-3-[(1R)-3-oxocyclopentyl]-N-1H-pyrazol-3-yl propanamide (62 mg) as a colorless amorphous substance.

Example 18

To a solution of (2R)-2-[3-cyclopropyl-4-(cyclopropylsulfonyl)phenyl]-N-[5-(2,2-dimethyl-1,3-dioxolan-4-yl)pyrazin-2-yl]-3-(tetrahydro-2H-pyran-4-yl)propanamide (150 mg) in THF (10 mL) was added 1 M hydrochloric acid at room temperature, followed by stirring at room temperature for 3 hours. After extraction with ethyl acetate, the organic layer was sequentially washed with saturated aqueous sodium bicarbonate and saturated brine. The organic layer was dried over anhydrous magnesium sulfate and concentrated to obtain (2R)-2-[3-cyclopropyl-4-(cyclopropylsulfonyl)phenyl]-N-[5-(1,2-dihydroxyethyl)pyrazin-2-yl]-3-(tetrahydro-2H-pyran-4-yl)propanamide (133 mg) as a white amorphous substance.

Example 19

To a solution of 5-({(2R)-2-[3-cyclopropyl-4-(cyclopropylsulfonyl)phenyl]-3-[(1R)-3-oxocyclopentyl]propanoyl}amino)pyrazine-2-carboxylic acid (102 mg), 1-hydroxybenzotriazole (44 mg), and N-[3-(dimethylamino)propyl]-N'-ethylcarbodiimide monohydrochloride (59 mg) in DMF (5 mL) were added dimethylamine monohydrochloride (22 mg) and triethylamine (0.09 mL) at room temperature. The reaction mixture was stirred at room temperature overnight, and water was then added thereto for liquid separation. The organic layer was sequentially washed with 1 M hydrochloric acid, saturated aqueous sodium bicarbonate, and saturated brine, and dried over anhydrous magnesium sulfate. The crude product obtained by concentration was purified by silica gel column chromatography (wetting with hexane:ethyl acetate=1:1, chloroform:methanol=1:0-10:1) to obtain 5-({(2R)-2-[3-cyclopropyl-4-(cyclopropylsulfonyl)phenyl]-3-[(1R)-3-oxocyclopentyl]propanoyl}amino)-N,N-dimethylpyrazine-2-carboxyamide (64 mg) as a pale yellow amorphous substance.

Example 20

To a suspension of (2E)-2-[3-cyclopropyl-4-(cyclopropylsulfonyl)phenyl]-N-(1-methyl-1H-pyrazol-3-yl)-3-[(1S)-3-oxocyclopentyl]acrylamide (140 mg) in ethanol (2 mL) was added sodium borohydride (12 mg) at 0° C., followed by stirring for 15 minutes. The reaction mixture was diluted with chloroform and the reaction was stopped with water. The organic layer was washed with saturated brine, dried over anhydrous magnesium sulfate, and then concentrated to obtain (2E)-2-[3-cyclopropyl-4-(cyclopropylsulfonyl)phenyl]-3-[(1S)-3-hydroxycyclopentyl]-N-(1-methyl-1H-pyrazol-3-yl)acrylamide (140 mg) as a colorless amorphous substance.

Example 21

To a solution of triphenylphosphine (606 mg) in dichloromethane (10 mL) was added N-bromosuccinimide (412 mg) under ice-cooling, followed by stirring for 15 minutes under ice-cooling. To the reaction mixture was added a solution of (2E)-2-[3-cyclopropyl-4-(cyclopropylsulfonyl)phenyl]-3-[(2R,3R,7S)-2,3-diphenyl-1,4-dioxaspiro[4.4]non-7-yl]acrylic acid (600 mg) in dichloromethane (10 mL) under ice-cooling, followed by stirring at room temperature for 30 minutes. A solution of an optically active product of 2-(2-amino-1,3-thiazol-4-yl)-2-hydroxypropyl acetate (the optically active product obtained at the first peak of Production Example 60) (227 mg) in dichloromethane (10 mL) and pyridine (0.17 mL) were added to the reaction mixture at room temperature, followed by stirring at room temperature overnight. To the reaction mixture was added water, followed by extraction with ethyl acetate. The organic layer was sequentially washed with 1 M hydrochloric acid, saturated aqueous sodium bicarbonate, and saturated brine and dried over anhydrous magnesium sulfate. After concentration, the obtained residue was purified by silica gel column chromatography (hexane:ethyl acetate=1:1-1:2) to obtain 2-[2-({(2E)-2-[3-cyclopropyl-4-(cyclopropylsulfonyl)phenyl]-3-[(2R,3R,7S)-2,3-diphenyl-1,4-dioxaspiro[4.4]non-7-yl]prop-2-enoyl}amino)-1,3-thiazol-4-yl]-2-hydroxypropyl acetate (690 mg) as a white amorphous substance. To a solution of 2-[2-({2E)-2-[3-cyclopropyl-4-(cyclopropylsulfonyl)phenyl]-3-[(2R,3R,7S)-2,3-diphenyl-1,4-dioxaspiro[4.4]non-7-yl]prop-2-enoyl}amino)-1,3-thiazol-4-yl]-2-hydroxypropyl acetate (690 mg) in methanol (4 mL) was added 1 M aqueous sodium hydroxide solution (1 mL), followed by stirring at room temperature for 3 hours. 1 M Hydrochloric acid was added thereto to adjust the pH to 4, followed by extraction with chloroform. The organic layer was dried over anhydrous magnesium sulfate and then concentrated to obtain (2E)-2-[3-cyclopropyl-4-(cyclopropylsulfonyl)phenyl]-N-[4-(1,2-dihydroxy-1-methylethyl)-1,3-thiazol-2-yl]-3-[(2R,3R,7S)-2,3-diphenyl-1,4-dioxaspiro[4.4]non-7-yl]acrylamide (655 mg) as a white amorphous substance. To a solution of (2E)-2-[3-cyclopropyl-4-(cyclopropylsulfonyl)phenyl]-N-[4-(1,2-dihydroxy-1-methylethyl)-1,3-thiazol-2-yl]-3-[(2R,3R,7S)-2,3-diphenyl-1,4-dioxaspiro[4.4]non-7-yl]acrylamide (655 mg) in 1,4-dioxane (4 mL) and THF (2 mL) was added 4 M hydrochloric acid (4 mL), followed by stirring at 50° C. for 2 hours. The reaction mixture was left to be cooled to room temperature and saturated brine was added thereto. After extraction with chloroform, the organic layer was dried over anhydrous magnesium sulfate. The crude product obtained by concentration was purified by silica gel column chromatography (hexane:ethyl acetate=1:1-1:3→chloroform:methanol=1:0-10:1) to obtain (2E)-2-[3-cyclopropyl-4-(cyclopropylsulfonyl)phenyl]-N-[4-(1,2-dihydroxy-1-methylethyl)-1,3-thiazol-2-yl]-3-[(1S)-3-oxocyclopentyl]acrylamide (329 mg) as a white amorphous substance.

Example 22

The (2E)-2-[3-cyclopropyl-4-(cyclopropylsulfonyl)phenyl]-3-[(1S)-3-hydroxycyclopentyl]-N-(1-methyl-1H-pyrazol-3-yl)acrylamide (145 mg) obtained in Example 20 was purified by silica gel column chromatography (chloroform:methanol=100:1) to obtain 2(E)-[3-cyclopropyl-4-(cyclopropylsulfonyl)phenyl]-3-[(1S,3S)-3-hydroxycyclopentyl]-N-(1-methyl-1H-pyrazol-3-yl)acrylamide (40 mg) (low polarity fraction, Example 22-1) and 2(E)-[3-cyclopropyl-4-(cyclopropylsulfonyl)phenyl]-3-[(1S,3R)-3-hydroxycyclopentyl]-N-(1-methyl-1H-pyrazol-3-yl)acrylamide (37 mg) (high polarity fraction, Example 22-2) as a colorless amorphous substance, respectively.

Example 23

To a solution of (2R)-2-[3-cyclopropyl-4-(cyclopropylsulfonyl)phenyl]-3-[(1R)-3-oxocyclopentyl]propionic acid (200 mg) in dichloromethane (10 mL) were sequentially added a solution of oxalyl chloride in 0.5 M dichloromethane (1.3 mL) and DMF (16 μL) under ice-cooling, followed by stirring for 30 minutes under ice-cooling. Thereafter, 1-(5-aminopyrazin-2-yl)ethanol (81 mg) and pyridine (0.09 mL) were added thereto under ice-cooling, followed by stirring for 3 hours. To the reaction mixture was added water under ice-cooling, followed by extraction with ethyl acetate. The organic layer was sequentially washed with 1 M hydrochloric acid, saturated aqueous sodium bicarbonate, and saturated brine, and dried over anhydrous magnesium sulfate. To a solution of the oily substance obtained by concentration in methanol (4 mL) was added 1 M aqueous sodium hydroxide solution (1 mL) at room temperature, followed by stirring at room temperature for 1 hour. To the reaction mixture was added 1 M hydrochloric acid to adjust the pH to 3, followed by extraction with ethyl acetate. The organic layer was sequentially washed with 1 M aqueous sodium hydroxide solution and saturated brine, and dried over anhydrous magnesium sulfate. The crude product obtained by concentration was purified by silica gel column chromatography (wetting with hexane:ethyl acetate=1:1, chloroform:methanol=1:0-10:1) to obtain (2R)-2-[3-cyclopropyl-4-(cyclopropylsulfonyl)phenyl]-N-[5-(1-hydroxyethyl)pyrazin-2-yl]-3-(tetrahydro-2H-pyran-4-yl)propanamide (170 mg) as a white amorphous substance.

In the same manner as the methods in Examples 1 to 23, Example compounds 24 to 103 were prepared. The structures of Example compounds are shown in Tables 28 to 48 below, and the preparation methods and the physicochemical data are shown in Tables 49 to 63 below.

Furthermore, the structures of the other compounds of the present invention are shown in Tables 64 to 65. These can be easily synthesized by the preparation methods above or the methods described in Examples, methods which are apparent to a skilled person in the art, or modified methods thereof.

In addition, the following abbreviations are used in Tables below. PEx: Production Example number, Ex: Example number, No: Compound number, Data: Physicochemical Data (EI: m/z value in EI-MS, FAB+: m/z value in FAB-MS (cation) ESI+: m/z value in ESI-MS (cation), ESI−: m/z value in ESI-MS (anion), NMR1: δ (ppm) of $^1$H NMR in DMSO-$d_6$, NMR2: δ (ppm) of $^1$H NMR in CDCl$_3$, NMR3: δ (ppm) of $^1$H NMR in CDCl$_3$ added with CD$_3$OD, diastereo mixture: mixture of diastereomers), Structure: Structural Formula (HCl in the structural formula represents hydrochloride), and Syn: Production Method (The numeral shows that the compound was prepared using a corresponding starting material, in the same manner as the Example Compound having its number as the Example number. A case where a plurality of the numerals are described indicates that the compound was prepared using corresponding starting materials, sequentially in the same manner as the Example Compounds having the numbers as the Example numbers). PSyn: Production Method (The numeral shows that the compound was prepared using a corresponding starting material, in the same manner as a Production Example Compound having its number as the Production Example number.)

Provided that indicates that the double bond is a mixture of an E isomer and a Z isomer.

TABLE 5

| PEx | Structure |
|---|---|
| 18 | 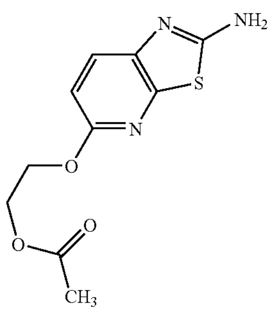 |
| 61 | 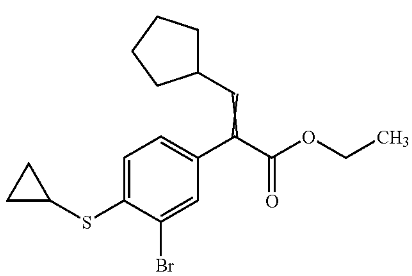 |
| 62 | 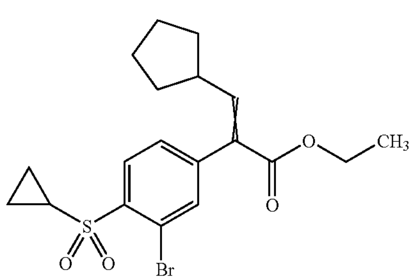 |
| 1 | 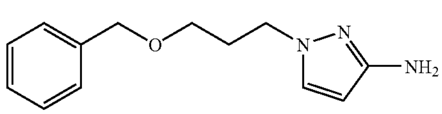 |

TABLE 5-continued

| PEx | Structure |
|---|---|
| 63 | 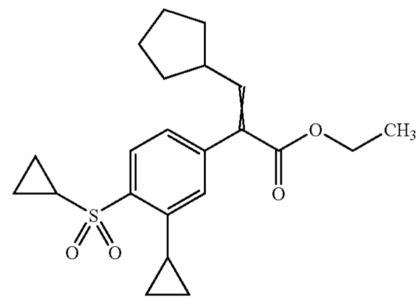 |
| 64 | 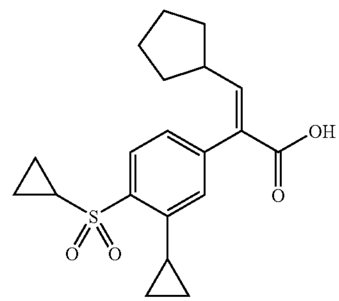 |

TABLE 6

| | |
|---|---|
| 2 | |
| 3 | |
| 8 | |
| 4 | |

TABLE 6-continued
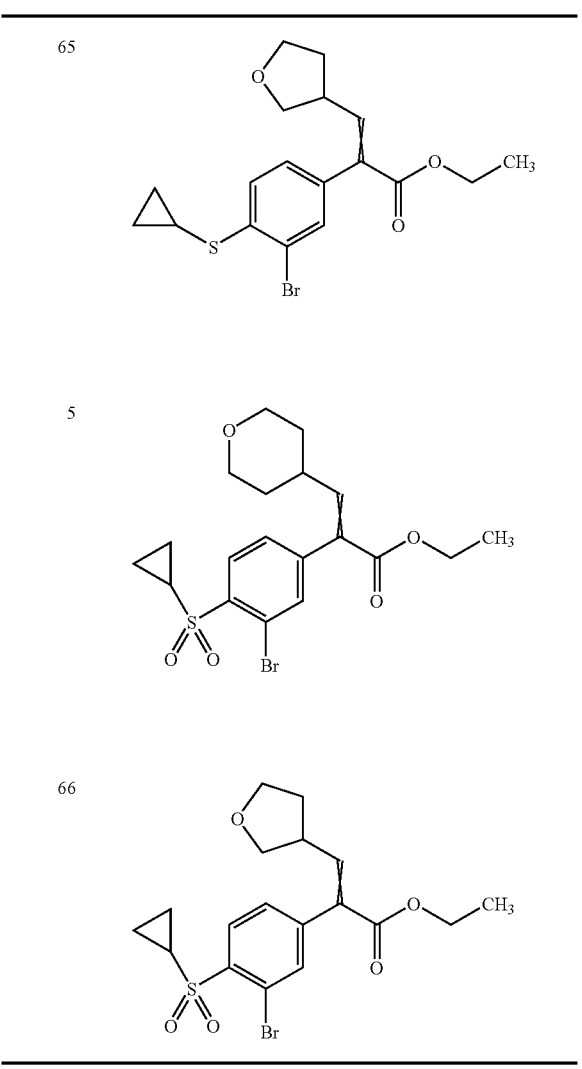
TABLE 7
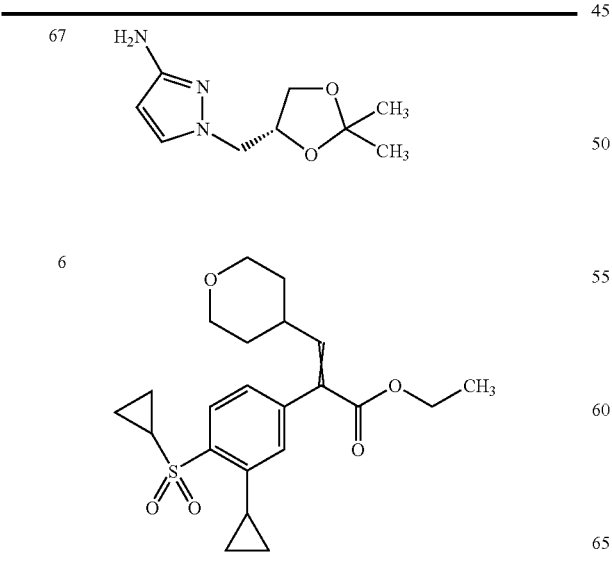
TABLE 7-continued
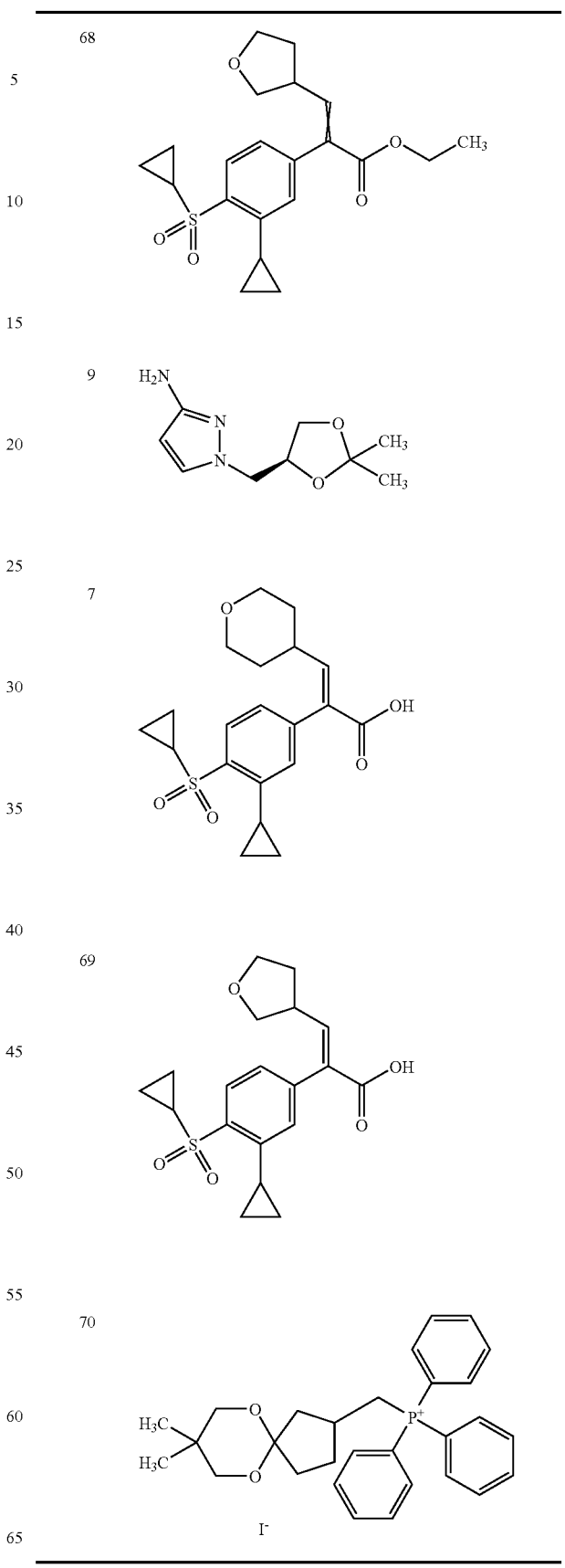

TABLE 8
71 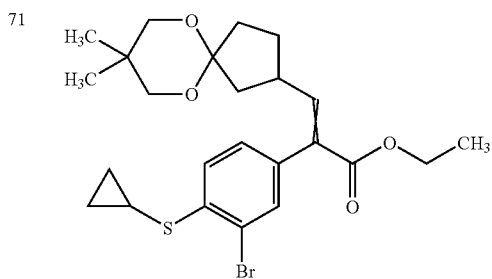
10 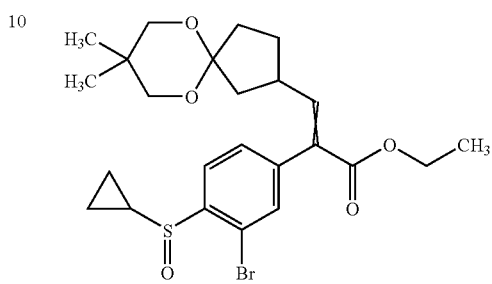
11 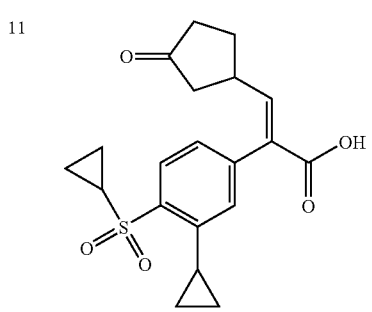
15 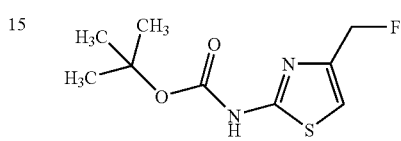
16 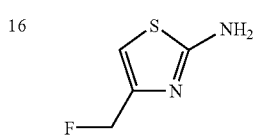
72 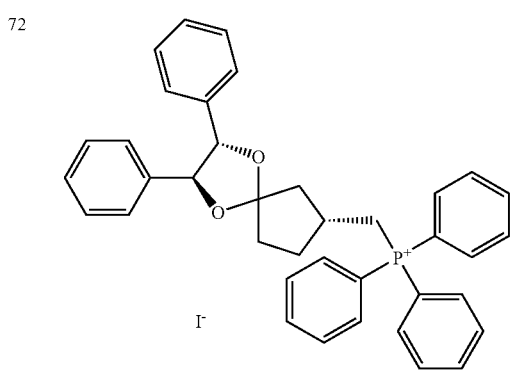
TABLE 9
73 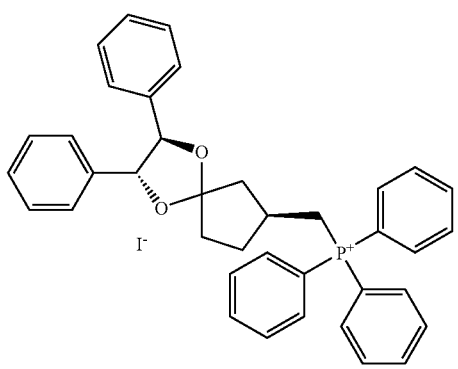
74 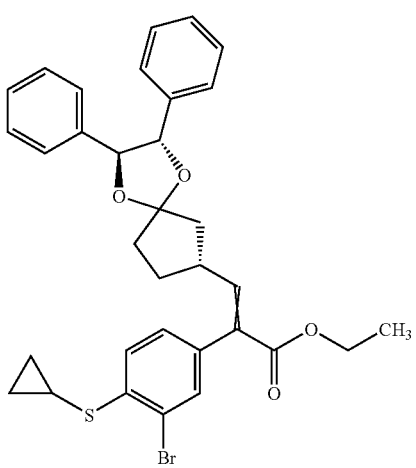
12 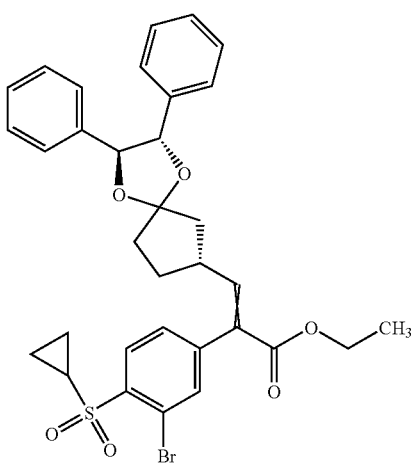

TABLE 9-continued
75
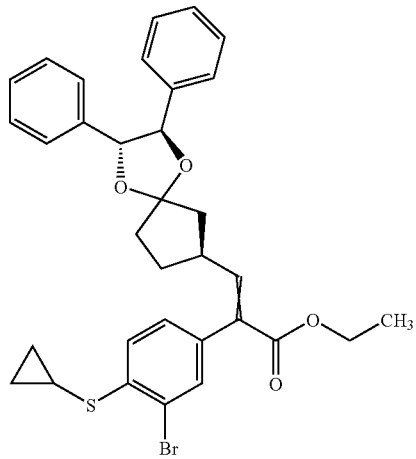
TABLE 10
76
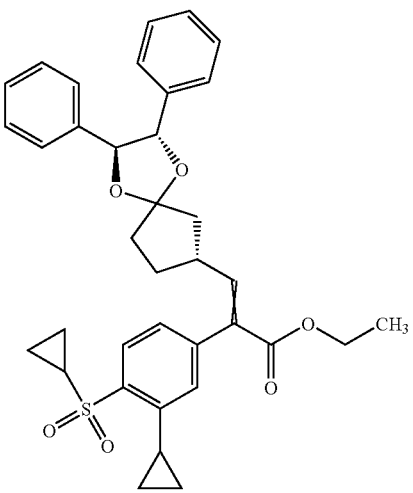
77
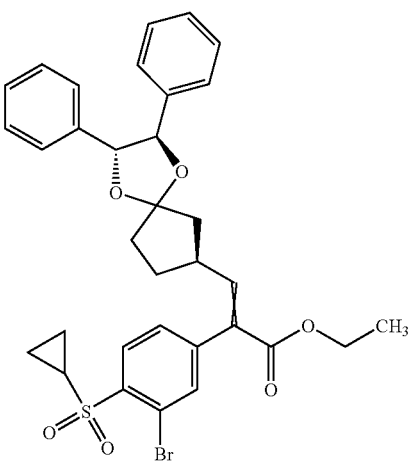
TABLE 10-continued
13
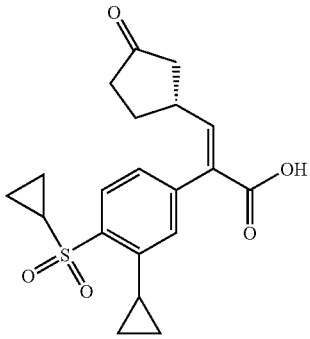
TABLE 11
78
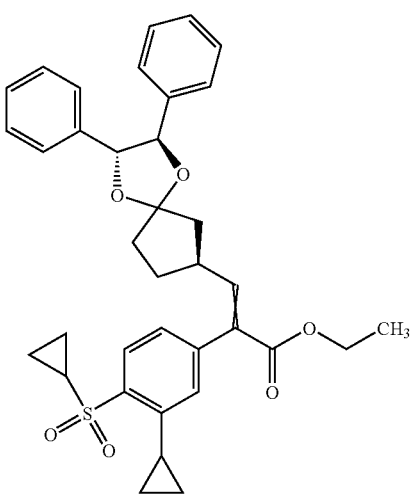
79
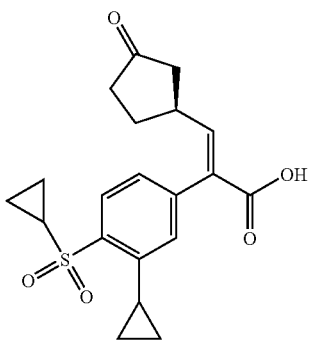
14
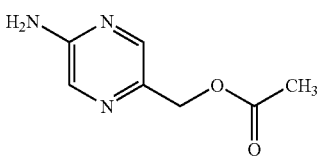

TABLE 11-continued
80 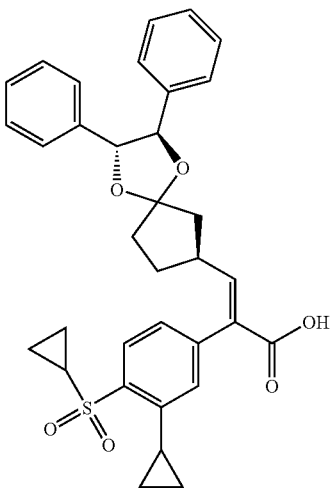
TABLE 12
17 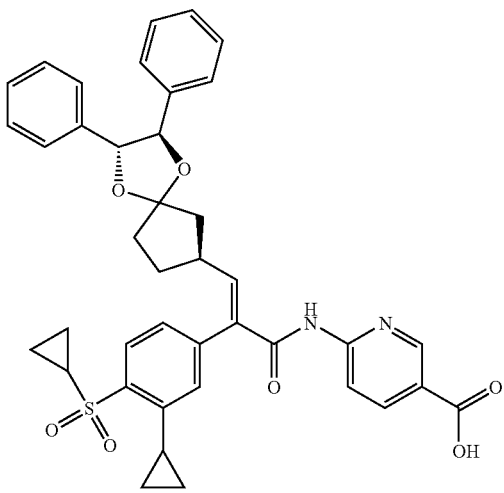
59 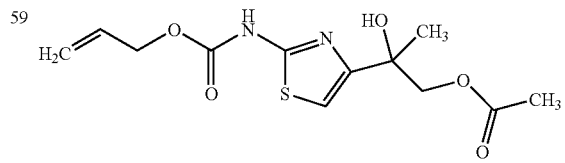
60 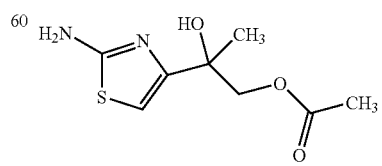
TABLE 12-continued
19 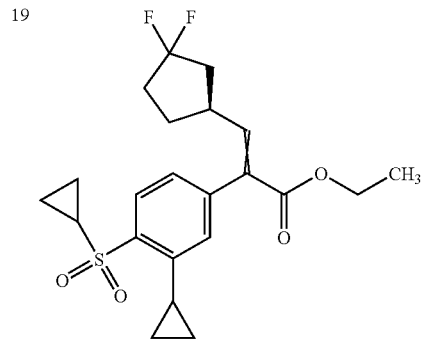
81 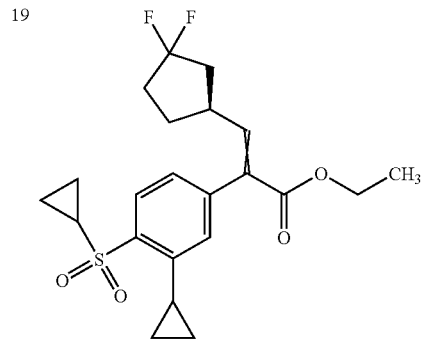
TABLE 13
33 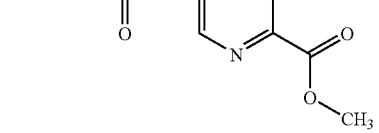
34 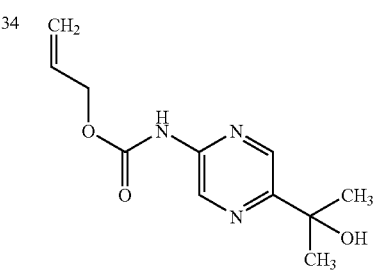
35 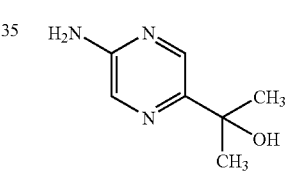

TABLE 13-continued
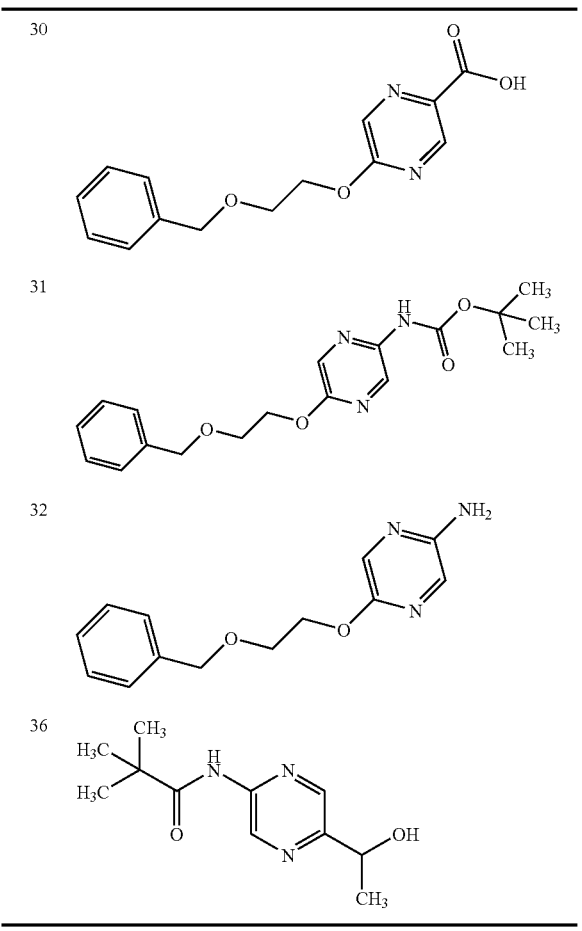
TABLE 14
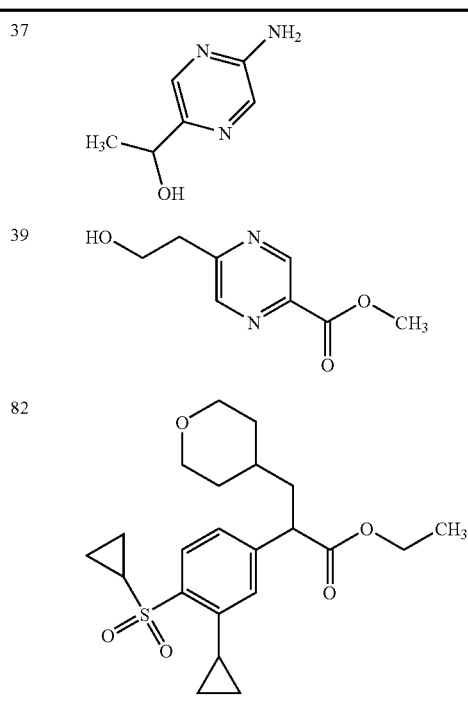
TABLE 14-continued
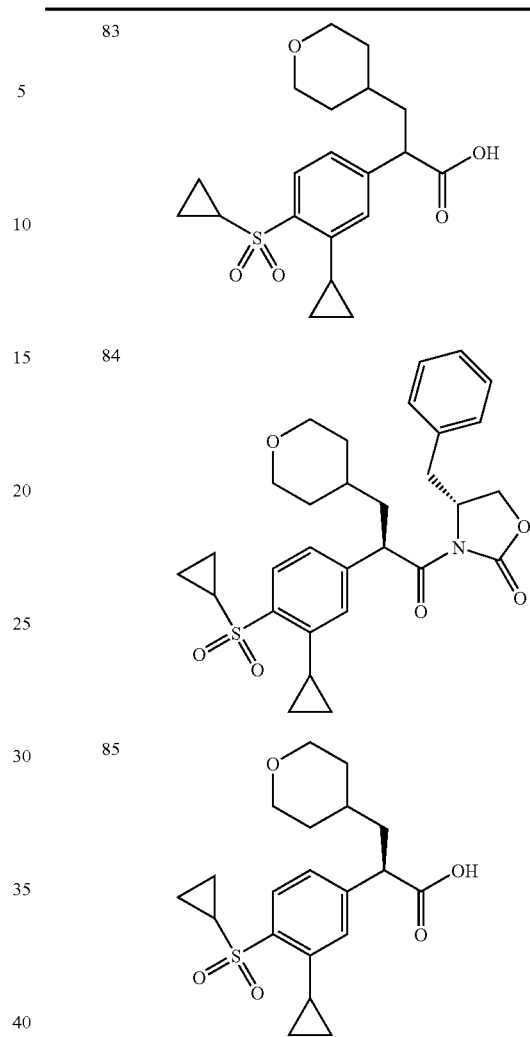
TABLE 15
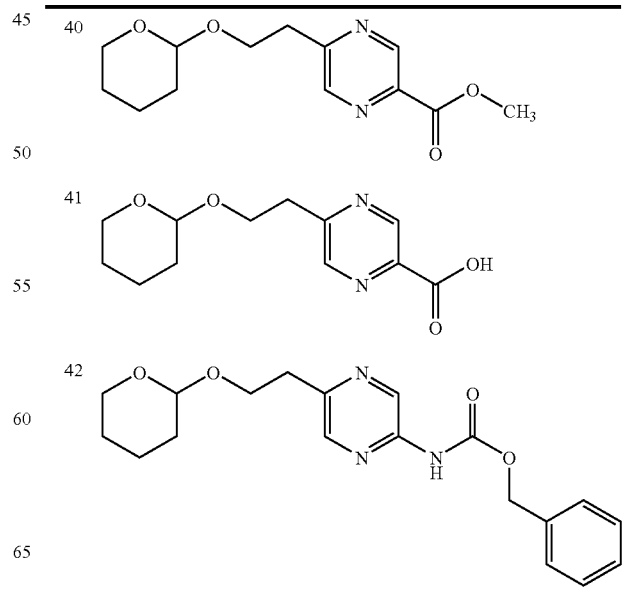

TABLE 15-continued
43 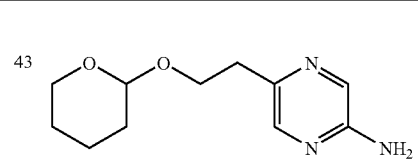
86 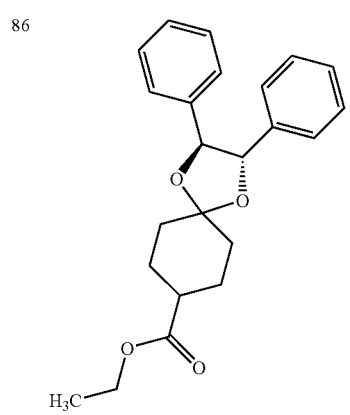
45 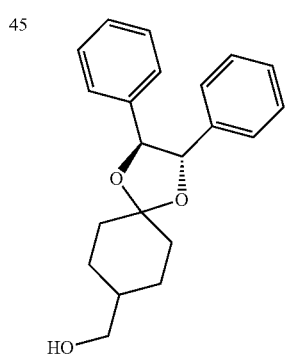
TABLE 16
46 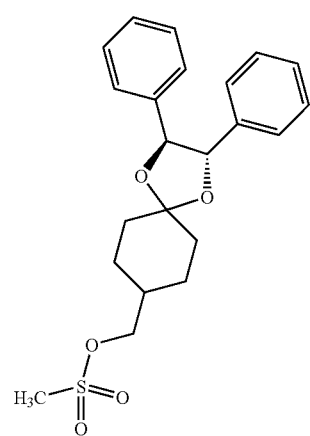
TABLE 16-continued
47 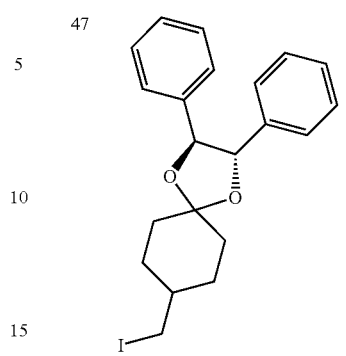
87 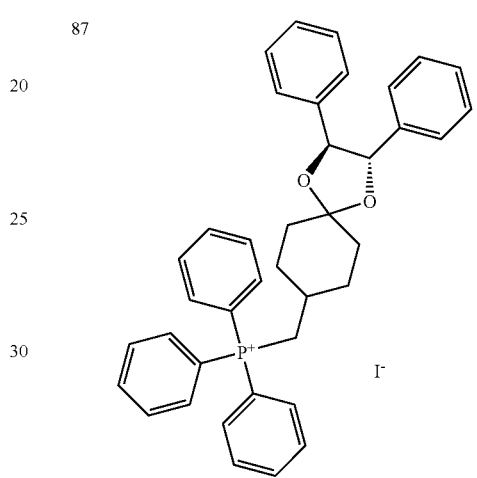
88 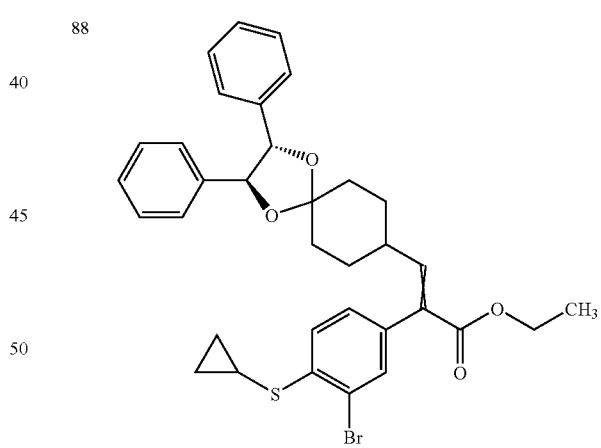
TABLE 17
38 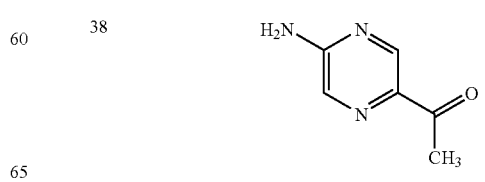

TABLE 17-continued
89
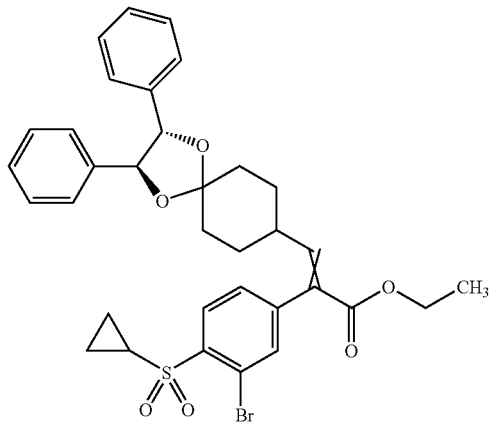
90
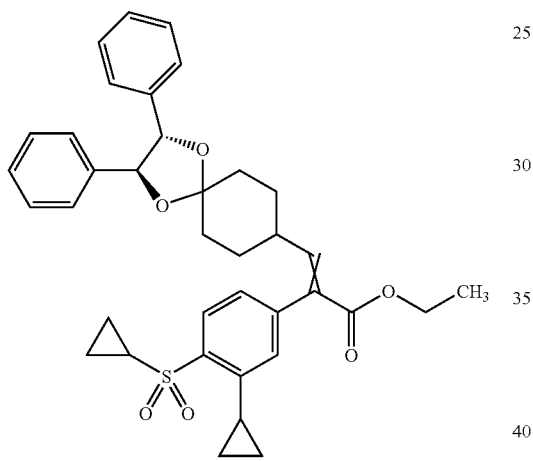
44
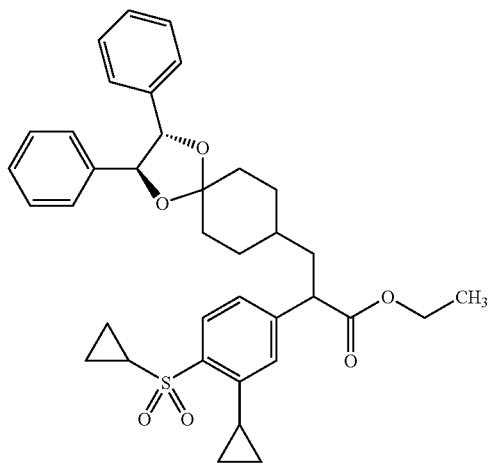
TABLE 18
91
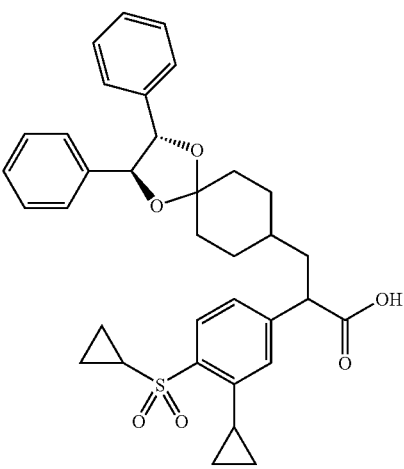
92
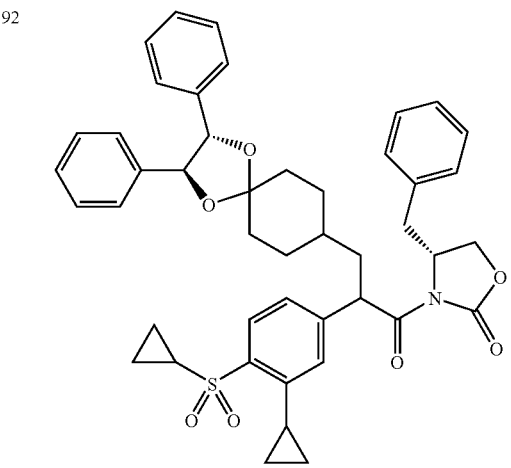
54
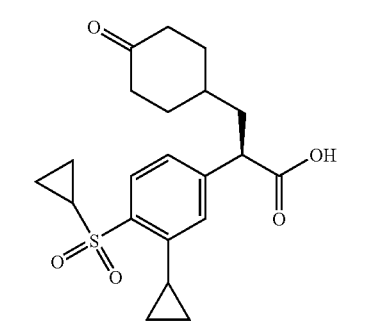
58
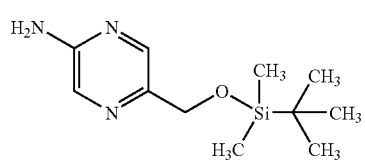

TABLE 18-continued
| | |
|---|---|
| 48 | 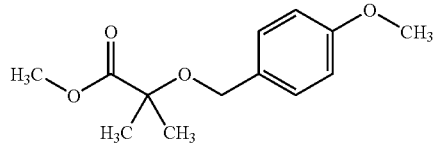 |
| 49 | 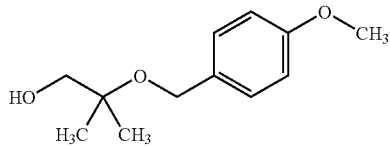 |
TABLE 19
| | |
|---|---|
| 50 | 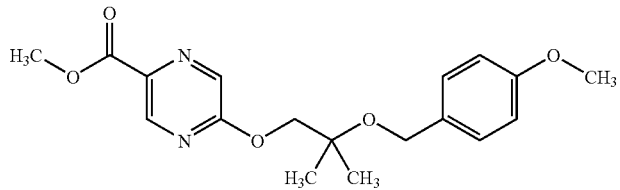 |
| 56 | 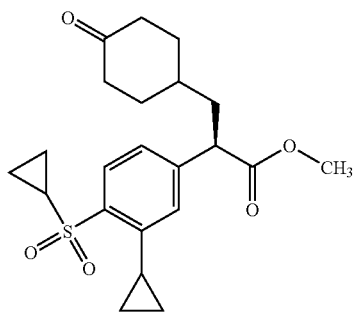 |
| 51 | 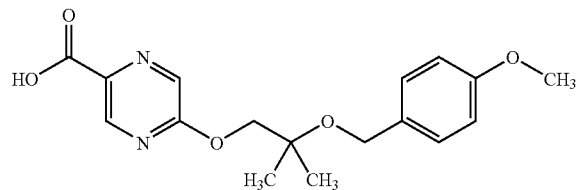 |
| 20 | 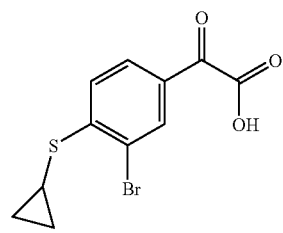 |
| 21 | 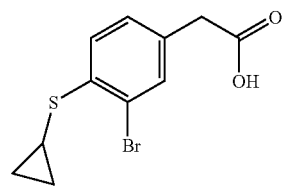 |
| 22 | 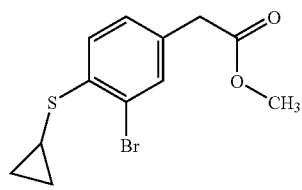 |

TABLE 19-continued
| 93 | 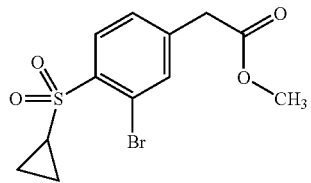 |
TABLE 20
| 23 | 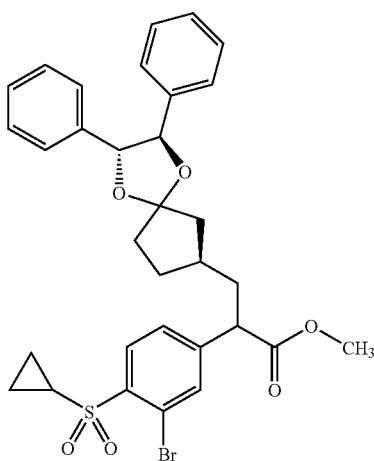 |
TABLE 20-continued
| 24 | 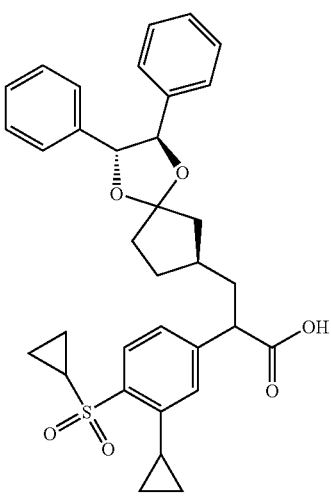 |
| 94 | 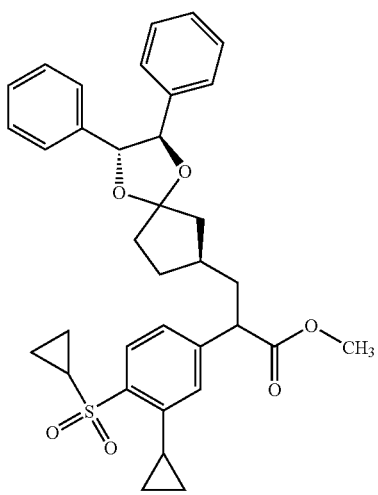 |
TABLE 21
| 25 | 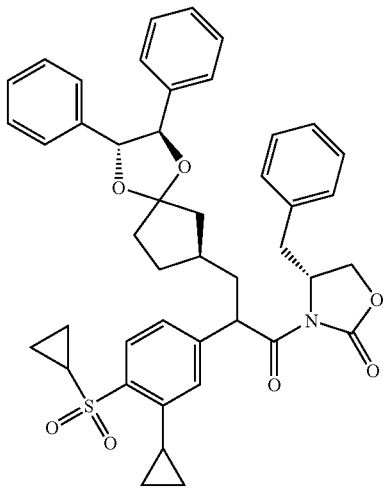 |

TABLE 21-continued
| | |
|---|---|
| 26 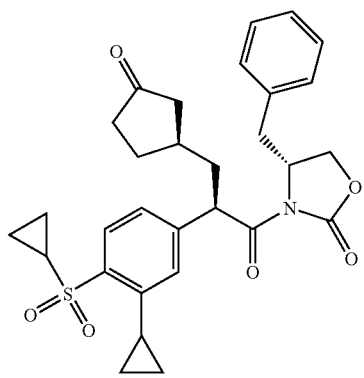 | 5 |
| | 28 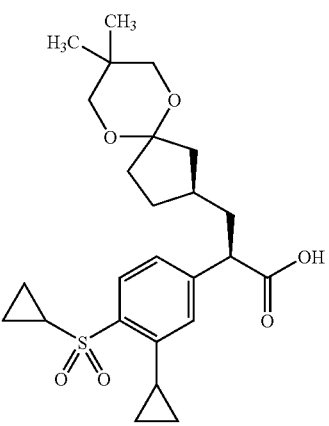 |
| 27 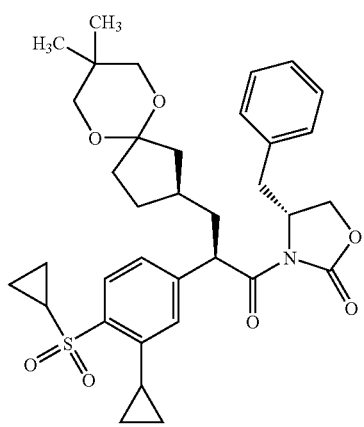 | |
TABLE 22
29 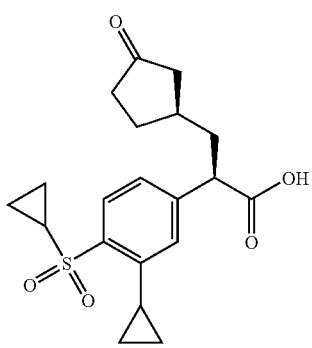
95 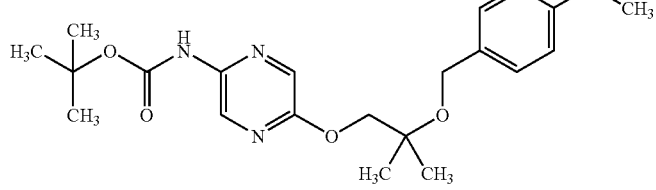
52 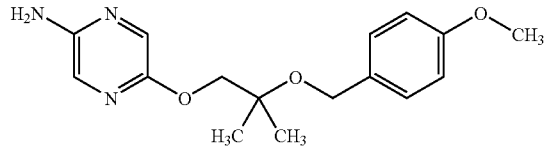

TABLE 22-continued
| | |
|---|---|
| 55 | 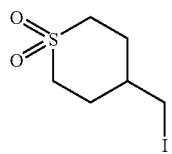 |
| 57 | 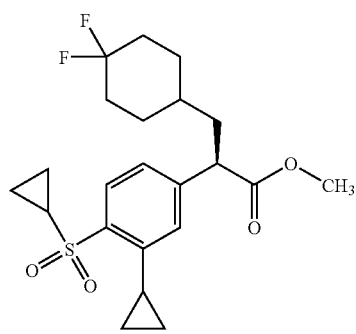 |
| 53 | 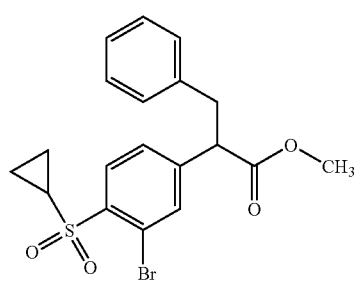 |
TABLE 23
| | |
|---|---|
| 96 | 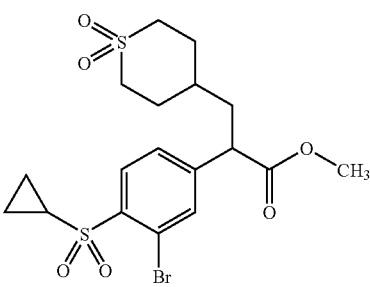 |
| 97 | 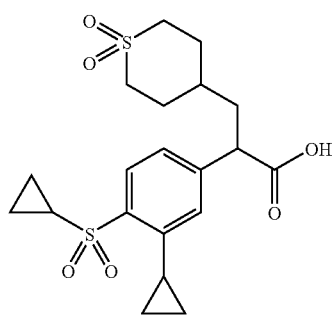 |
TABLE 23-continued
| | |
|---|---|
| 98 | 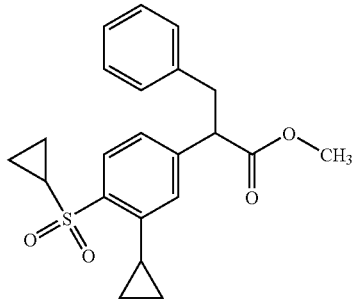 |
| 99 | 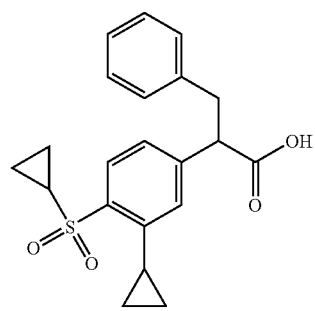 |

TABLE 23-continued

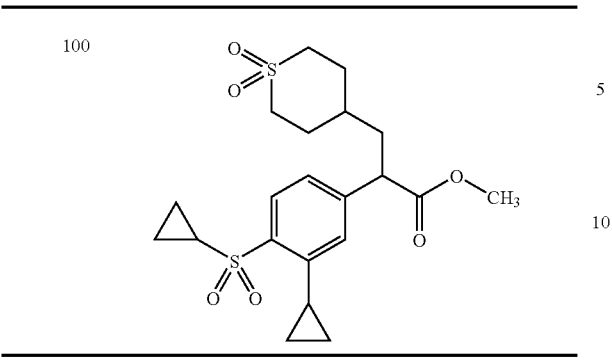

100

TABLE 24

| PEx | PSyn | Data |
|---|---|---|
| 18 | 18 | NMR2: 2.11 (3H, s), 3.50-3.80 (2H, br), 4.39-4.46 (2H, m), 4.47-4.54 (2H, m), 6.73 (1H, d, J = 8.7 Hz), 7.61 (1H, d, J = 8.7 Hz)<br>ESI+: 254 |
| 61 | 4 | EI: 394, 396 |
| 62 | 5 | EI: 426, 428 |
| 1 | 1 | NMR2: 2.02-2.18 (2H, m), 3.42 (2H, t, J = 6.0 Hz), 3.48-3.72 (2H, br s), 4.04 (2H, t, J = 6.0 Hz), 4.78 (2H, s), 5.53 (1H, d, J = 2.0 Hz), 7.05 (1H, d, J = 2.0 Hz), 7.26-7.41 (5H, m)<br>EI: 231 |
| 63 | 6 | EI: 388 |
| 64 | 7 | NMR2: 0.81-0.94 (2H, m), 1.00-1.11 (2H, m), 1.12-1.20 (2H, m), 1.25-1.83 (10H, m), 2.27-2.49 (1H, m), 2.75-2.89 (1H, m), 2.90-3.02 (1H, m), 6.80 (1H, d, J = 1.5 Hz), 7.09-7.15 (2H, m), 7.92 (1H, d, J = 8.1 Hz)<br>FAB+: 361 |
| 2 | 2 | EI: 228, 230 |
| 3 | 3 | EI: 328, 330 |
| 8 | 8 | ESI+: 347 |
| 4 | 4 | ESI+: 411, 413 |
| 65 | 4 | ESI+: 397, 399 |
| 5 | 5 | ESI+: 443, 445 |
| 66 | 5 | ESI+: 429, 431 |
| 67 | 9 | NMR2: 1.35 (3H, s), 1.39 (3H, s), 3.61 (2H, br), 3.71-3.83 (1H, m), 3.98-4.11 (3H, m), 4.35-4.46 (1H, m), 5.59 (1H, d, J = 2.3 Hz), 7.20 (1H, d, J = 2.3 Hz)<br>ESI+: 198 |
| 6 | 6 | ESI+: 405 |
| 68 | 6 | ESI+: 391 |
| 9 | 9 | NMR2: 1.35 (3H, s), 1.39 (3H, s), 3.61 (2H, br s), 3.71-3.83 (1H, m), 3.98-4.11 (3H, m), 4.35-4.46 (1H, m), 5.59 (1H, d, J = 2.3 Hz), 7.20 (1H, d, J = 2.3 Hz)<br>EI: 197 |
| 7 | 7 | ESI+: 377 |
| 69 | 7 | ESI+: 363 |
| 70 | 8 | FAB+: 445 |
| 71 | 4 | EI: 494, 496 |
| 10 | 10 | ESI+: 511, 513 |

TABLE 25

| | | |
|---|---|---|
| 11 | 11 | NMR2: 0.82-0.91 (2H, m), 1.01-1.12 (2H, m), 1.12-1.21 (2H, m), 1.33-1.41 (2H, m), 1.76-1.89 (1H, m), 2.04-2.23 (3H, m), 2.28-2.40 (2H, m), 2.74-2.89 (2H, m), 2.90-3.04 (1H, m), 6.81 (1H, br s), 7.22 (1H, d, J = 10.4 Hz), 7.13 (1H, dd, J = 8.1, 1.6 Hz), 7.96 (1H, d, J = 8.1 Hz) |
| 15 | 15 | NMR2: 1.56 (9H, s), 5.36 (2H, d, J = 47.2 Hz), 6.94 (1H, d, J = 3.3 Hz), 9.25 (1H, br)<br>FAB+: 233 |
| 16 | 16 | NMR2: 5.00 (2H, br s), 5.22 (2H, d, J = 47.5 Hz), 6.59 (1H, d, J = 3.5 Hz)<br>ESI+: 133 |
| 72 | 8 | ESI+: 555 |
| 73 | 8 | ESI+: 555 |
| 74 | 4 | FAB+: 604, 606 |
| 12 | 12 | FAB+: 637, 639 |
| 75 | 4 | FAB+: 604, 606 |

TABLE 25-continued

| | | |
|---|---|---|
| 76 | 6 | FAB+: 599 |
| 77 | 12 | FAB+: 637, 639 |
| 13 | 13 | FAB+: 375 |
| 78 | 6 | FAB+: 599 |
| 79 | 13 | ESI+: 375 |
| 14 | 14 | EI: 167 |
| 80 | 7 | FAB+: 571 |
| 17 | 17 | NMR2: 0.82-1.00 (2H, m), 1.02-1.15 (2H, m), 1.16-1.29 (2H, m), 1.34-1.46 (2H, m), 1.55-2.42 (6H, m), 2.67-3.14 (3H, m), 4.63-4.77 (2H, m), 6.92 (1H, s), 7.10 (1H, d, J = 10.5 Hz), 7.14-7.41 (12H, m), 8.05 (1H, d, J = 8.3 Hz), 8.32-8.54 (2H, m), 8.89 (1H, s) |
| 59 | 59 | NMR2: 1.56 (3H, s), 2.06 (3H, s), 4.22 (1H, d, J = 11.3 Hz), 4.35 (1H, d, J = 11.3 Hz), 4.75 (2H, d, J = 5.7 Hz), 5.32 (1H, dd, J = 10.4, 1.1 Hz), 5.40 (1H, dd, J = 17.2, 1.1 Hz), 5.88-6.06 (1H, m), 6.83 (1H, s) |
| 60 | 60 | NMR1: 1.31 (3H, s), 1.98 (3H, s), 3.95 (1H, d, J = 11.0 Hz), 4.16 (1H, d, J = 11.0 Hz), 5.13 (1H, s), 6.34 (1H, s), 6.83 (2H, br s) |
| 19 | 19 | EI: 424 |
| 81 | 7 | FAB+: 397 |
| 33 | 33 | ESI+: 238 |
| 34 | 34 | ESI+: 238 |
| 35 | 35 | ESI+: 154 |
| 30 | 30 | ESI+: 275 |
| 31 | 31 | ESI+: 346 |

TABLE 26

| | | |
|---|---|---|
| 32 | 32 | ESI+: 246 |
| 36 | 36 | ESI+: 224 |
| 37 | 37 | ESI+: 140 |
| 39 | 39 | ESI+: 183 |
| 82 | 44 | FAB+: 407 |
| 83 | 24 | FAB+: 379 |
| 84 | 25 | ESI+: 538 |
| 85 | 28 | FAB+: 379 |
| 40 | 40 | ESI+: 267 |
| 41 | 41 | ESI+: 253 |
| 42 | 42 | ESI+: 358 |
| 43 | 43 | ESI+: 224 |
| 86 | 27 | FAB+: 367 |
| 45 | 45 | FAB+: 325 |
| 46 | 46 | FAB+: 403 |
| 47 | 47 | FAB+: 435 |
| 87 | 8 | FAB+: 570 |
| 88 | 4 | FAB+: 618, 620 |
| 38 | 38 | ESI+: 138 |
| 89 | 5 | FAB+: 651, 653 |
| 90 | 6 | FAB+: 613 |
| 44 | 44 | FAB+: 615 |
| 91 | 24 | ESI+: 391 (—$C_{14}H_{12}O$; deketalization) |
| 92 | 25 | FAB+: 550 (—$C_{14}H_{12}O$; deketalization) |
| 54 | 54 | ESI+: 391 |
| 58 | 58 | ESI+: 240 |
| 48 | 48 | NMR2: 1.52 (6H, s), 3.78 (3H, s), 3.81 (3H, s), 4.41 (2H, s), 6.88-6.91 (2H, m), 7.27-7.34 (2H, m) |
| 49 | 49 | NMR2: 1.27 (6H, s), 3.48 (2H, d, J = 6.3 Hz), 3.81 (3H, s), 4.41 (2H, s), 6.87-6.90 (2H, m), 7.25-7.27 (2H, m) |
| 50 | 50 | NMR2: 1.39 (6H, s), 3.76 (3H, s), 3.99 (3H, s), 4.38 (2H, s), 4.46 (2H, s), 6.81-6.88 (2H, m), 7.20-7.26 (2H, m), 8.31 (1H, d, J = 1.3 Hz), 8.82 (1H, d, J = 1.3 Hz) |
| 56 | 56 | ESI+: 405 |
| 51 | 51 | ESI−: 331 |
| 20 | 20 | ESI−: 299 |
| 21 | 21 | ESI+: 287, 289 |
| 22 | 22 | NMR2: 0.71-0.75 (2H, m), 1.11-1.16 (2H, m), 2.10-2.15 (1H, m), 3.57 (2H, s), 3.70 (3H, s), 7.22 (1H, dd, J = 1.8, 8.1 Hz), 7.43 (1H, d, J = 1.8 Hz), 7.49 (1H, d, J = 8.8) |
| 93 | 5 | ESI+: 333, 335 |
| 23 | 23 | ESI+: 429, 431 (—$C_{14}H_{12}O$; deketalization) |

TABLE 27

| | | |
|---|---|---|
| 94 | 6 | ESI+: 391 (—C$_{14}$H$_{12}$O; deketalization) |
| 24 | 24 | ESI+: 377 (—C$_{12}$H$_{14}$O; deketalization) |
| 25 | 25 | ESI+: 536 (—C$_{14}$H$_{12}$O; deketalization) |
| 26 | 26 | ESI+: 536 |
| 27 | 27 | ESI+: 622 |
| 28 | 28 | ESI+: 377 (—C$_5$H$_{10}$O; deketalization) |
| 29 | 29 | ESI+: 377 |
| 95 | 31 | NMR2: 1.40 (9H, s), 1.56 (6H, s), 3.78 (3H, s), 4.31 (2H, s), 4.48 (2H, s), 6.83-6.86 (2H, m), 7.24-7.29 (3H, m), 8.02-8.03 (1H, m) |
| 52 | 52 | NMR2: 1.36 (6H, s), 3.78 (3H, s), 4.20 (2H, s), 4.47 (2H, s), 6.83-6.86 (2H, m), 7.23-7.26 (2H, m), 7.52 (1H, d, J = 1.5 Hz), 7.82 (1H, d, J = 1.5 Hz) |
| 55 | 55 | ESI+: 275 |
| 57 | 57 | NMR2: 0.86-0.91 (2H, m), 1.01-1.07 (2H, m), 1.13-1.19 (2H, m), 1.22-1.28 (1H, m), 1.30-1.36 (2H, m), 1.50-1.84 (6H, m), 1.98-2.22 (4H, m), 2.77-2.80 (1H, m), 2.86-2.99 (1H, m), 3.62-3.74 (4H, m), 6.88-6.96 (1H, m), 7.21-7.27 (1H, m), 7.86-7.90 (1H, m) |
| 53 | 53 | NMR2: 1.02-1.10 (2H, m), 1.30-1.36 (2H, m), 3.02 (1H, dd, J = 9.5, 22.3 Hz), 3.08-3.10 (1H, m), 3.42 (1H, dd, J = 11.3, 22.3 Hz), 3.65 (3H, s), 3.90 (1H, dd, J = 9.5, 11.3 Hz), 7.06-7.11 (2H, m), 7.16-7.30 (3H, m), 7.39 (1H, dd, J = 2.3, 11.0 Hz), 7.72 (1H, d, J = 2.3 Hz), 7.95 (1H, d, J = 11.0) |
| 96 | 53 | ESI−: 477, 479 |
| 97 | 24 | NMR2: 0.84-0.90 (2H, m), 1.01-1.09 (2H, m), 1.14-1.22 (2H, m), 1.24-1.27 (1H, m), 1.30-1.37 (2H, m), 1.70-1.80 (1H, m), 1.81-1.97 (2H, m), 2.05-2.20 (3H, m), 2.76-3.10 (6H, m), 3.63-3.71 (1H, m), 6.91-6.94 (1H, m), 7.22-7.28 (1H, m), 7.89-7.94 (1H, m) |
| 98 | 6 | ESI+: 385 |
| 99 | 24 | ESI+: 371 |
| 100 | 6 | NMR2: 0.84-0.91 (2H, m), 1.01-1.09 (2H, m), 1.14-1.22 (2H, m), 1.24-1.29 (1H, m), 1.30-1.38 (2H, m), 1.68-1.78 (1H, m), 1.80-1.98 (2H, m), 2.05-2.20 (3H, m), 2.77-3.09 (6H, m), 3.61-3.67 (1H, m), 3.69 (3H, s), 6.89 (1H, d, J = 2.0 Hz), 7.21 (1H, dd, J = 2.0, 12.0 Hz), 7.90 (1H, d, J = 12.0 Hz) |

TABLE 28

| Ex | Structure |
|---|---|
| 24 | 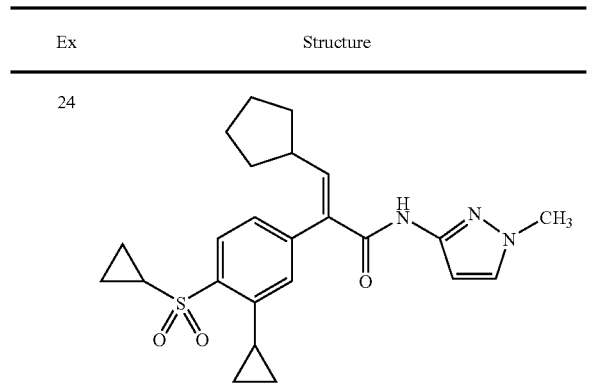 |
| 1 | 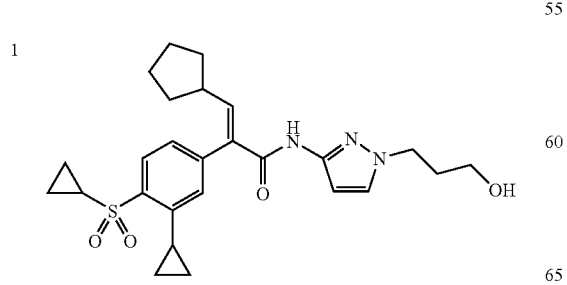 |

TABLE 28-continued

| Ex | Structure |
|---|---|
| 2 | 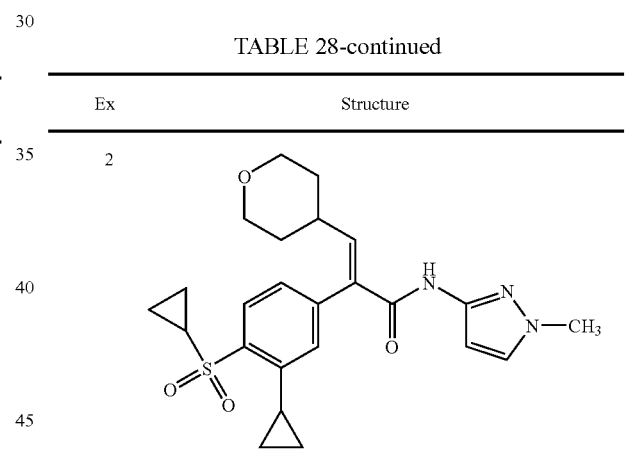 |
| 25 | 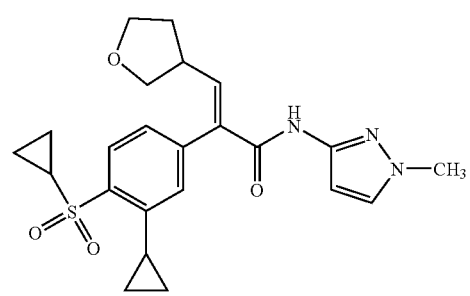 |

TABLE 28-continued

| Ex | Structure |
|---|---|
| 26 | (structure) |

TABLE 29

| Ex | Structure |
|---|---|
| 27 | (structure) |
| 28 | (structure) |
| 29 | (structure) |
| 3 | (structure) |
| 30 | (structure) |
| 31 | (structure) |

TABLE 30

| Ex | Structure |
|---|---|
| 32 | (structure) |
| 33 | (structure) |
| 34 | (structure) |

TABLE 30-continued
35
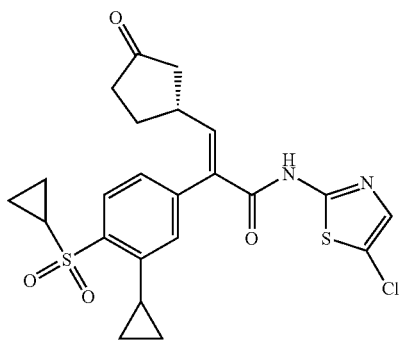
36
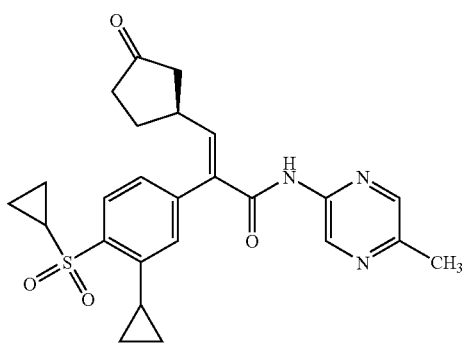
TABLE 31
37
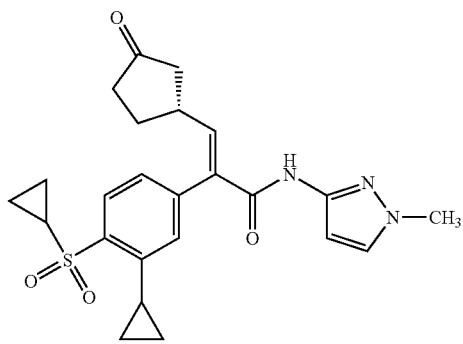
38
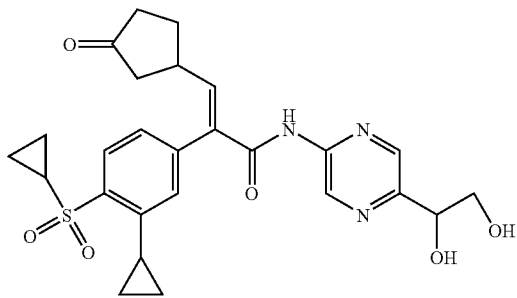
TABLE 31-continued
6
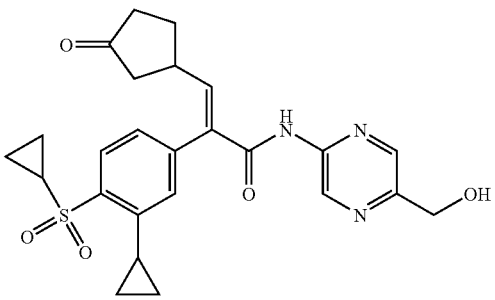
4-1
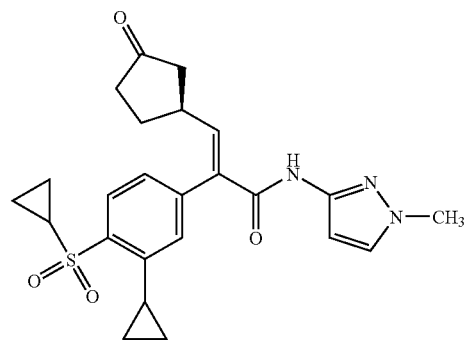
4-2
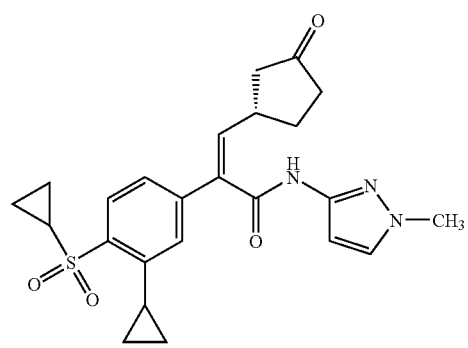
TABLE 32
39
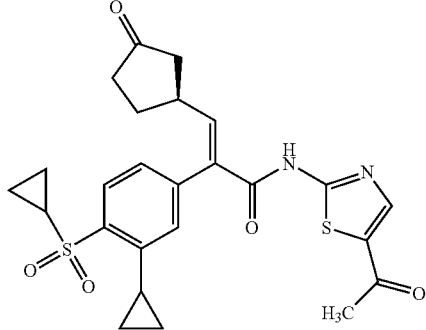

TABLE 32-continued
40 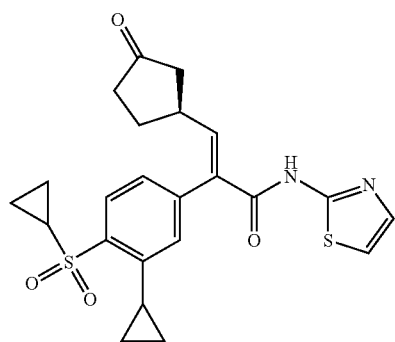
41 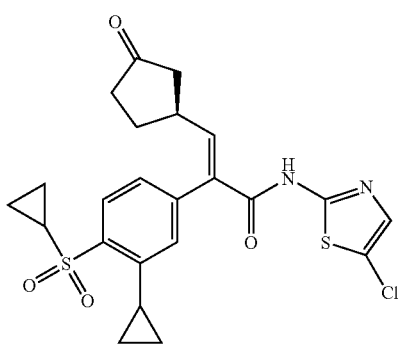
42 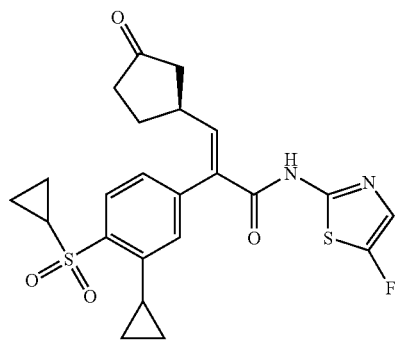
43 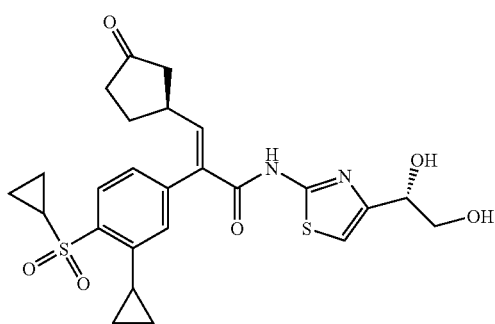
TABLE 33
44 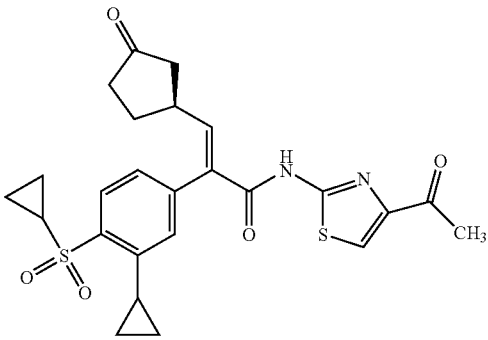
45 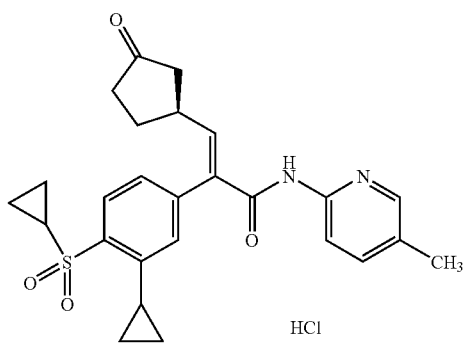
HCl
46 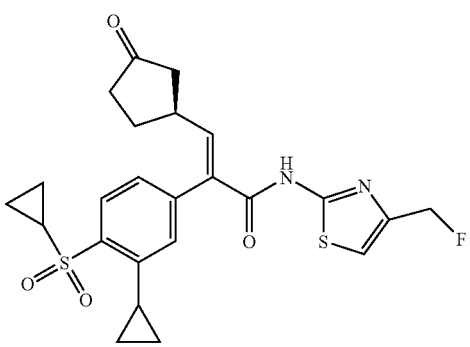
5 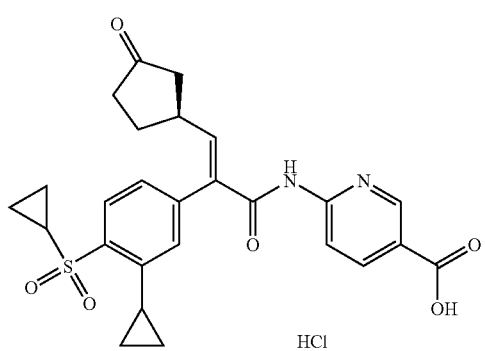
HCl TABLE 33-continued
7
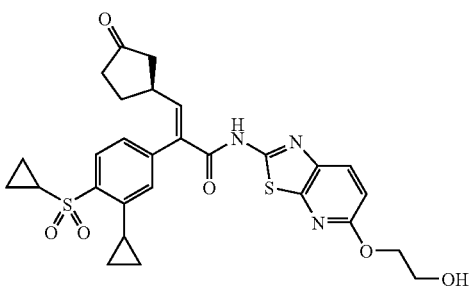
TABLE 34
47
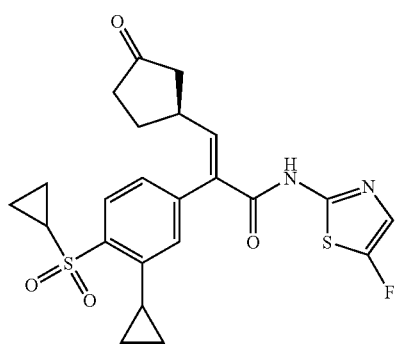
48
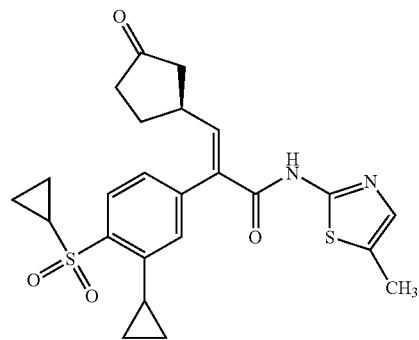
21
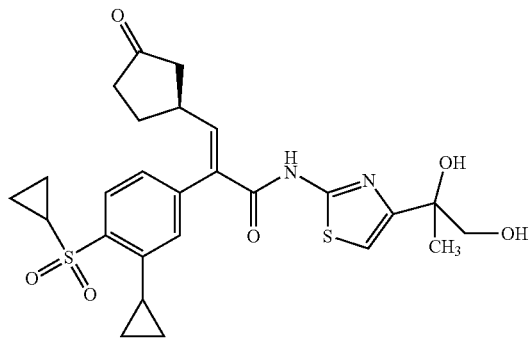
TABLE 34-continued
49
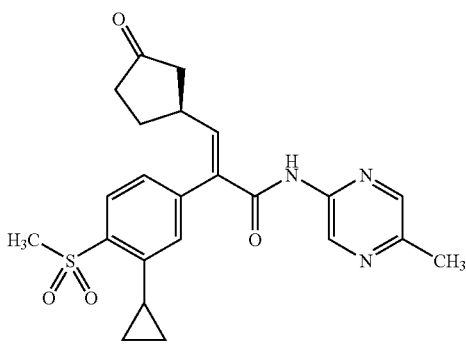
50
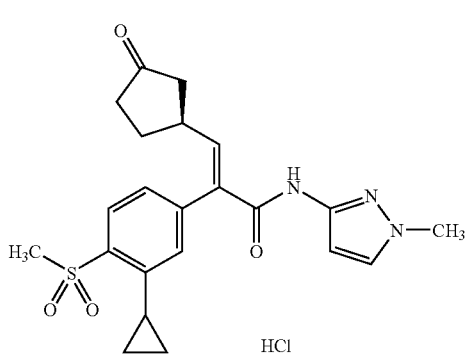
HCl
TABLE 35
51
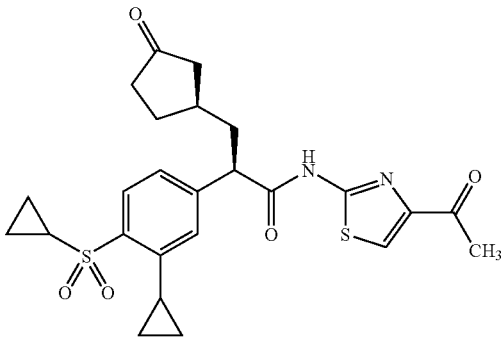
52
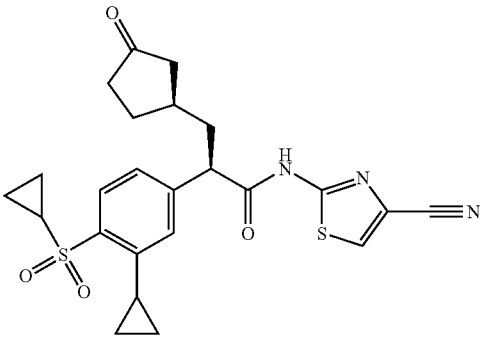

TABLE 35-continued
53 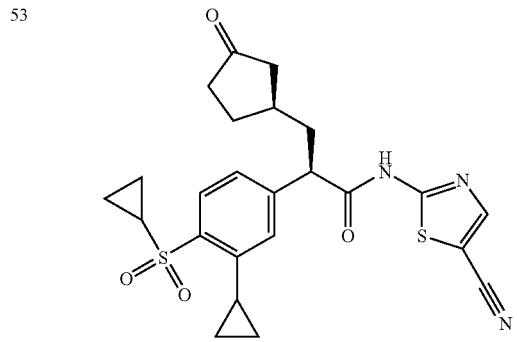
9 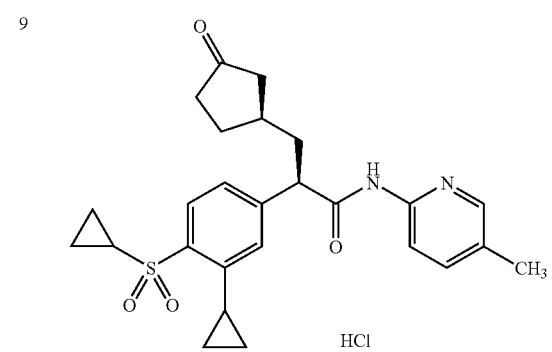
54 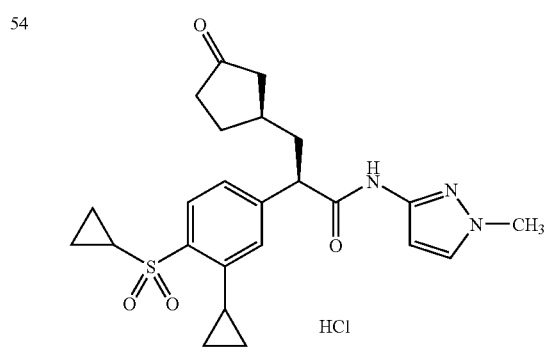
TABLE 36
55 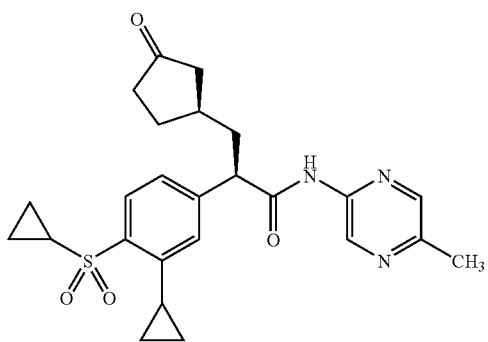
TABLE 36-continued
56 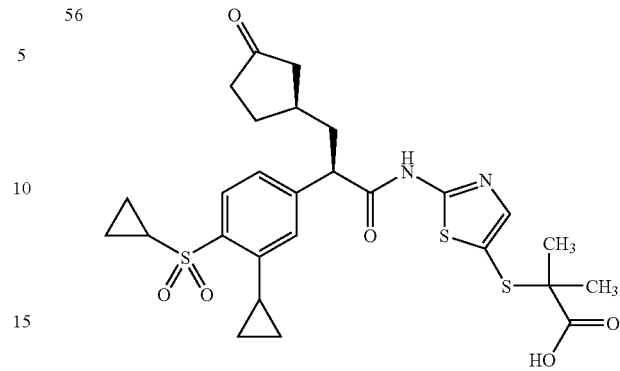
57 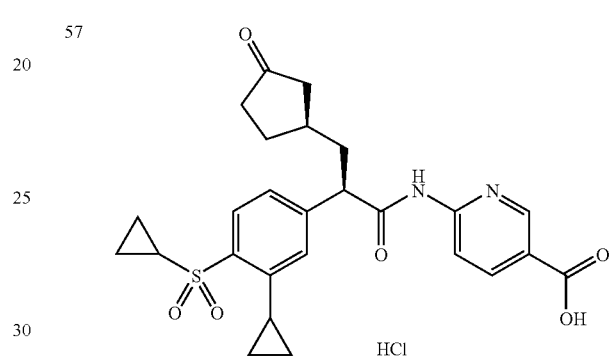
58 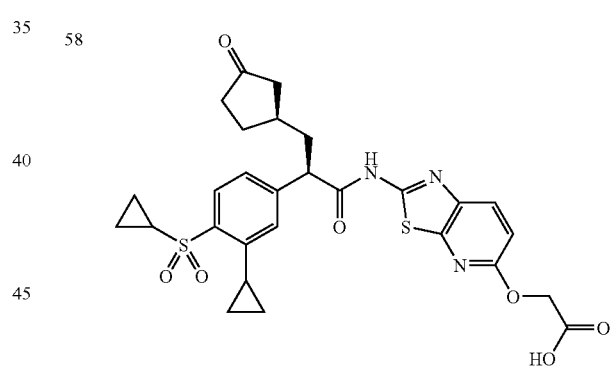
TABLE 37
59 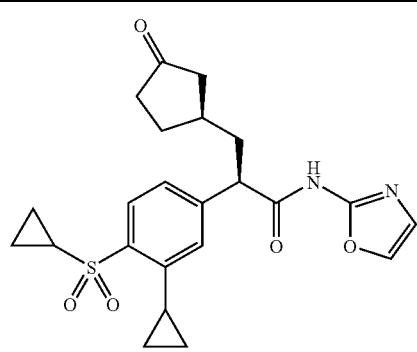

TABLE 37-continued
60
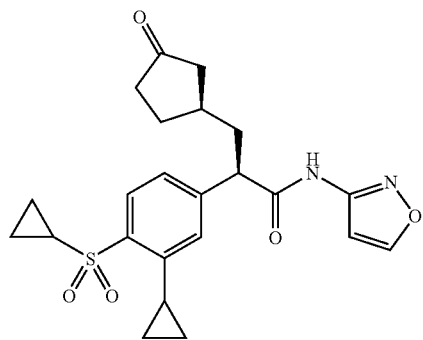
61
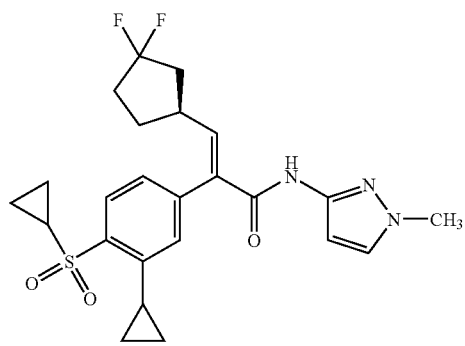
62
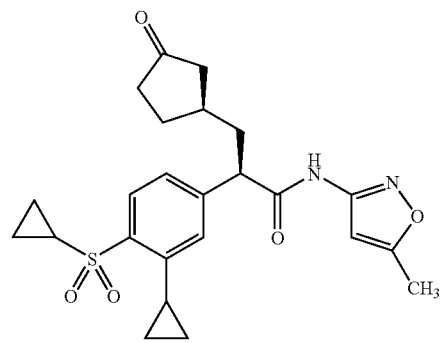
63
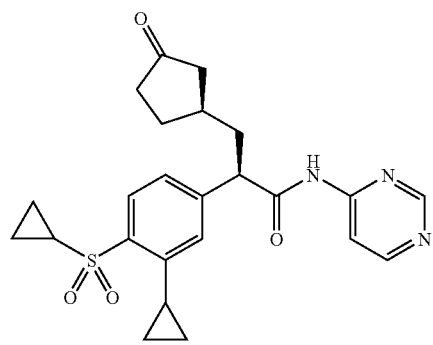
TABLE 38
64
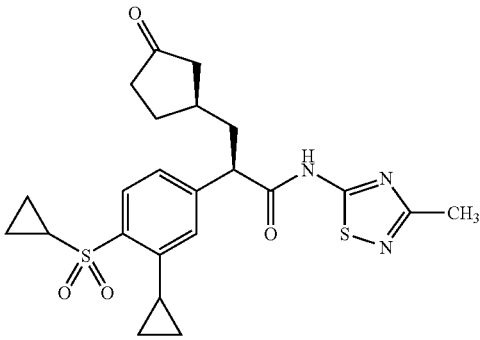
65
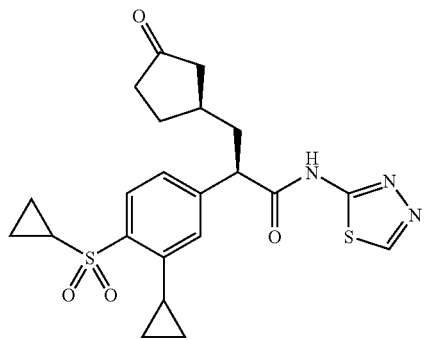
66
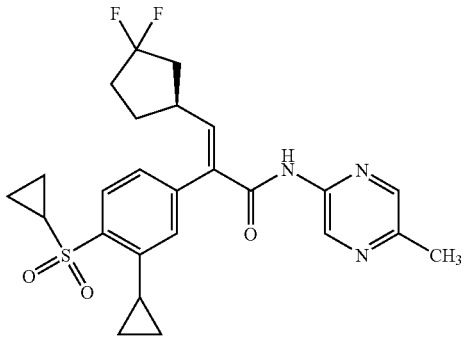
67
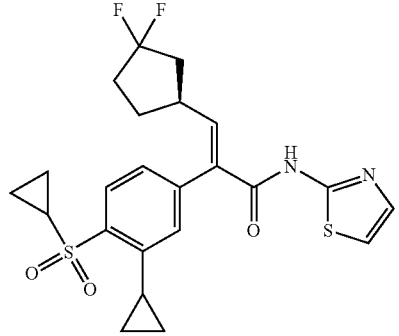

TABLE 38-continued
68
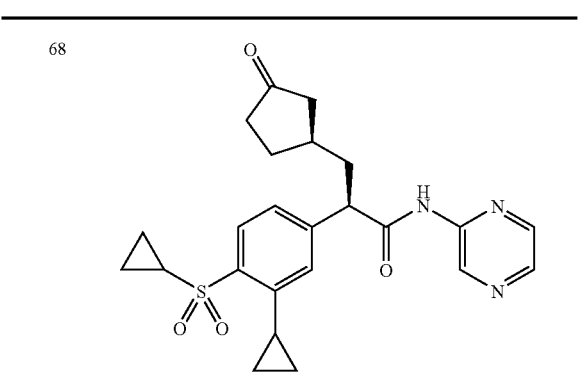
TABLE 39
69
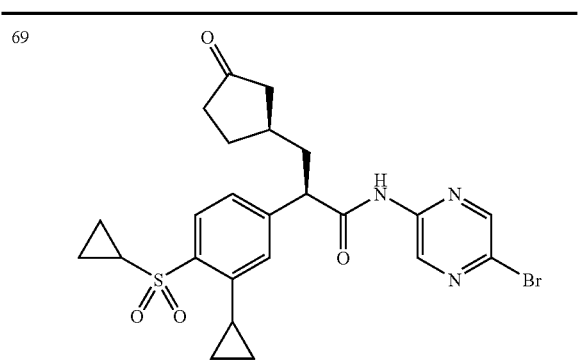
20
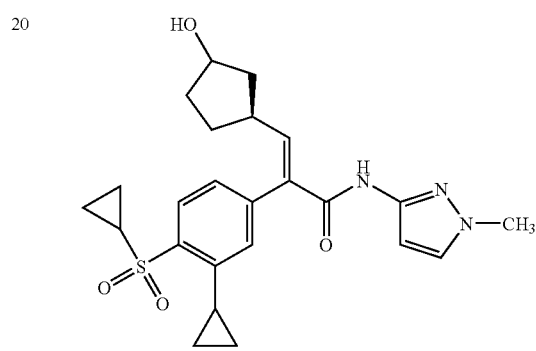
8
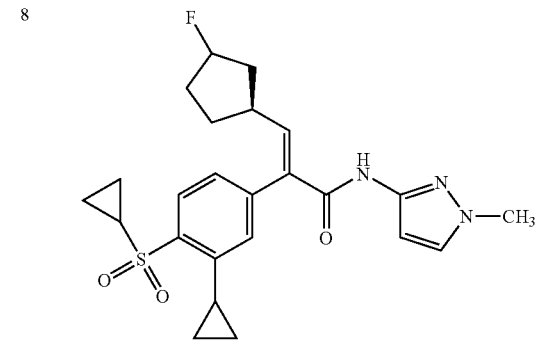
TABLE 39-continued
70
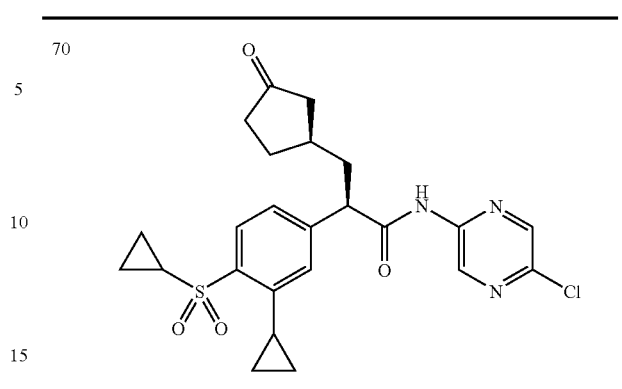
71
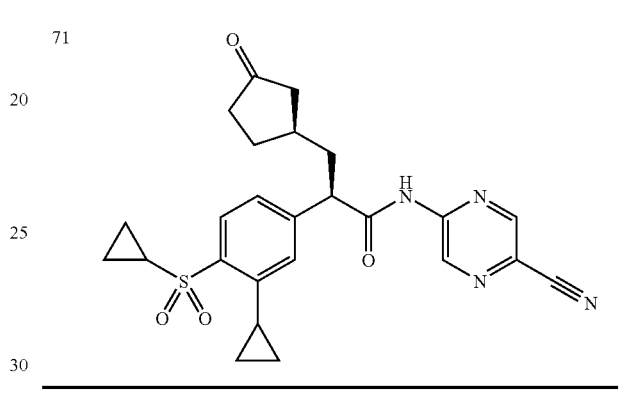
TABLE 40
72
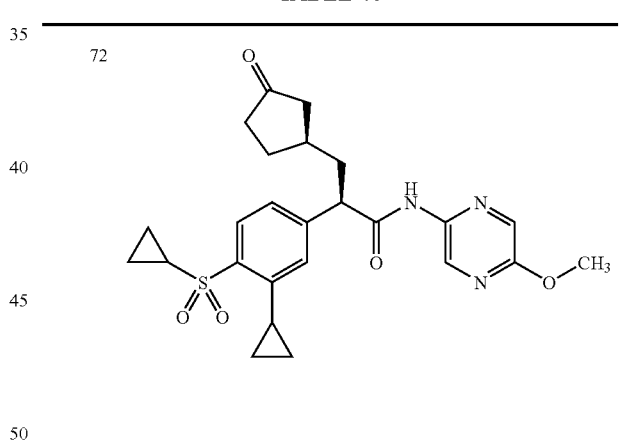
73
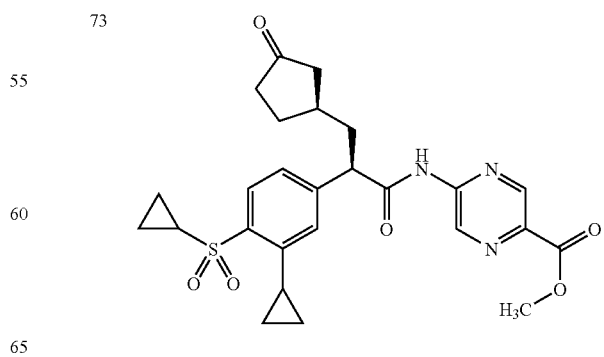

TABLE 40-continued
74
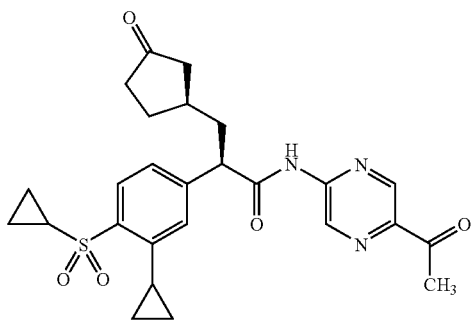
75
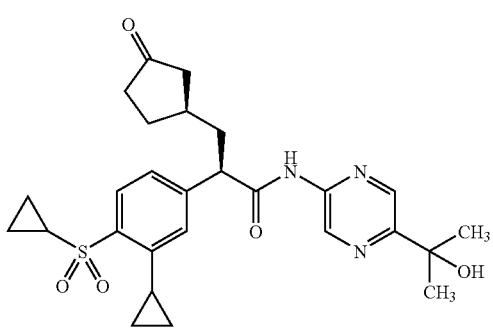
76
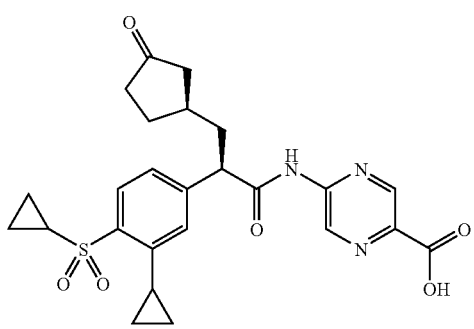
TABLE 41
19
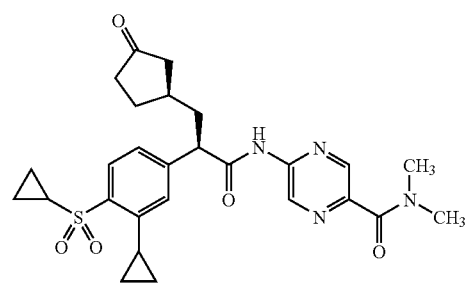
TABLE 41-continued
77
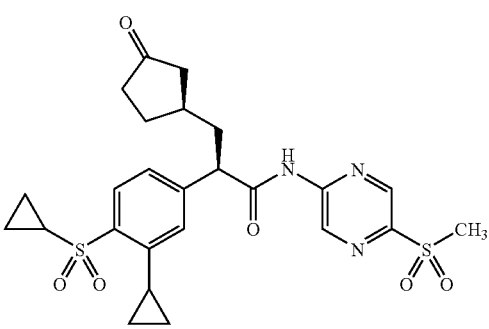
78
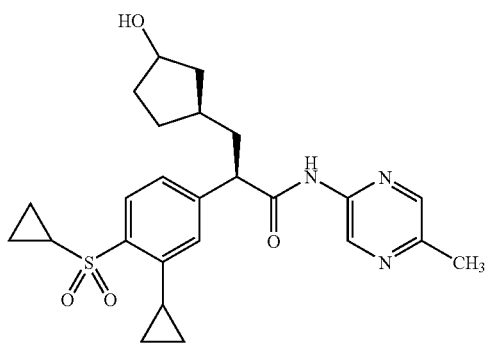
79
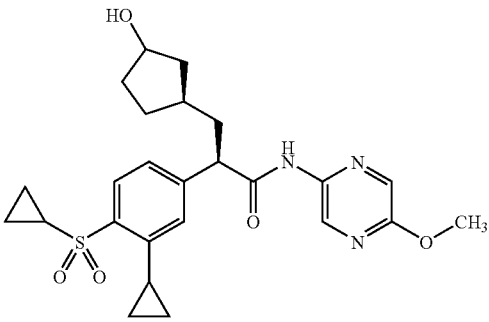
80
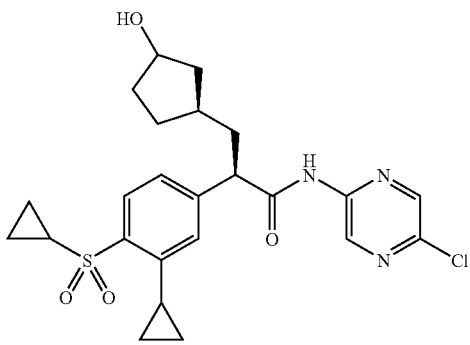

TABLE 42
81
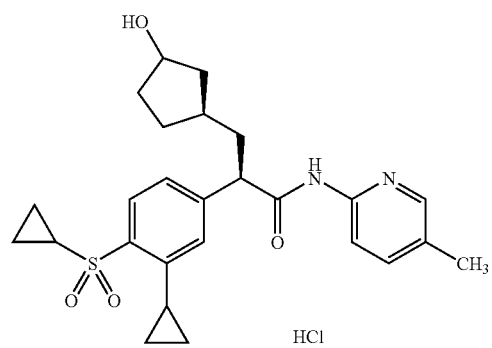
HCl
11
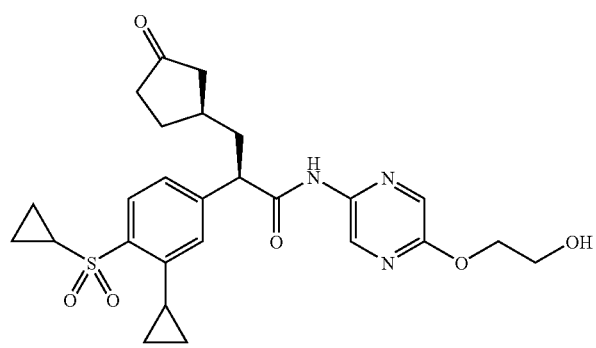
82
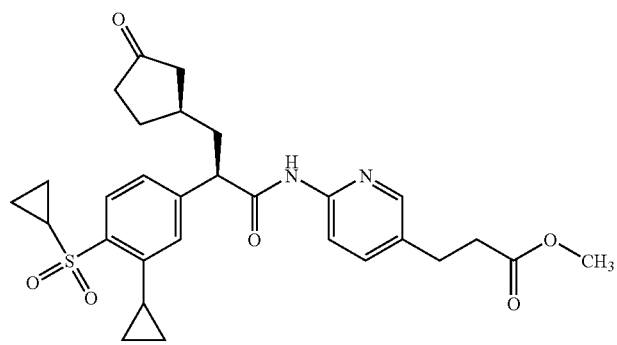
83
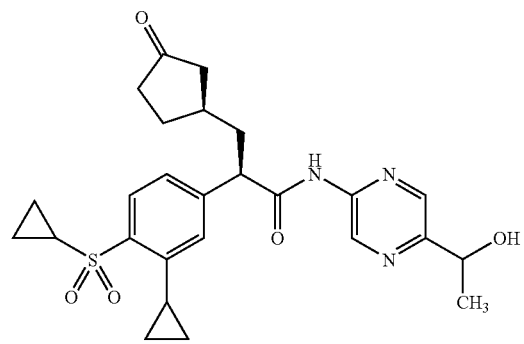

TABLE 42-continued
84 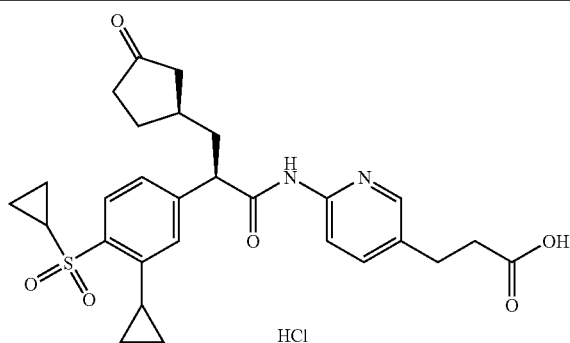
HCl
TABLE 43
12 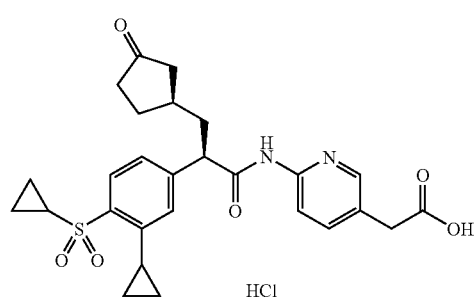
HCl
22-1 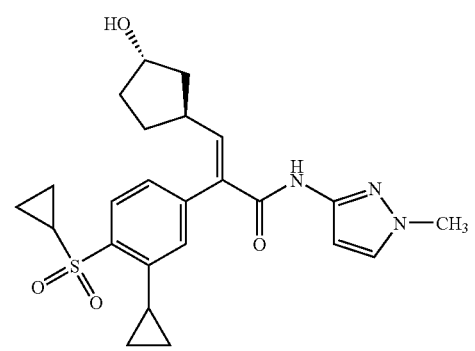
22-2 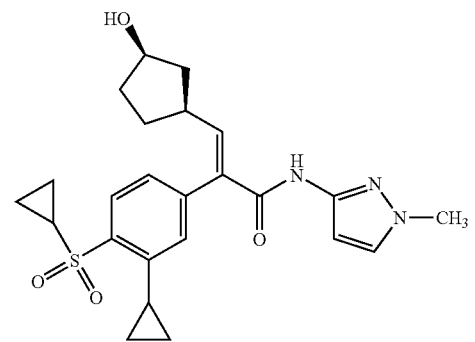
TABLE 43-continued
16 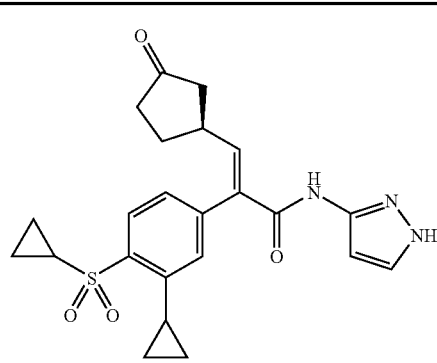
85 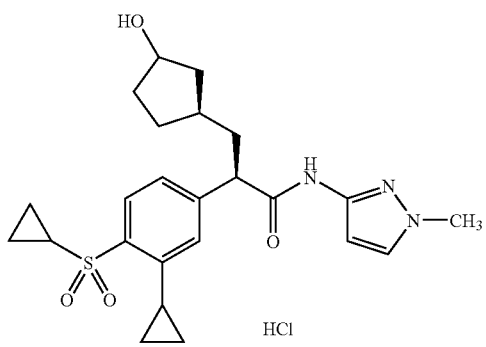
HCl
TABLE 44
86 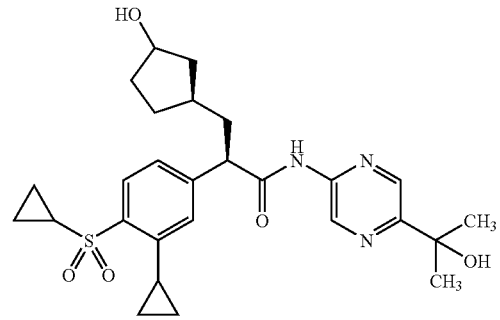

TABLE 44-continued
87
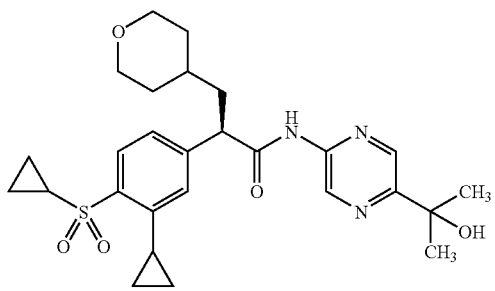
88
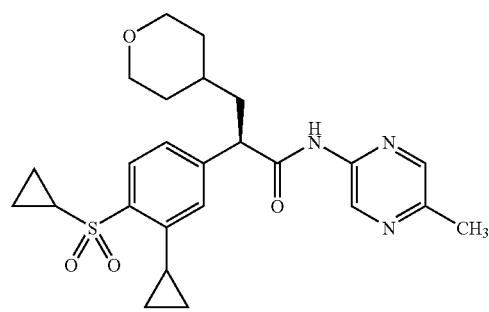
TABLE 44-continued
89
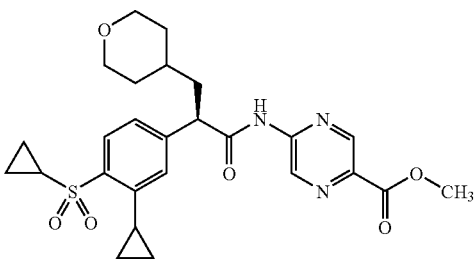
90
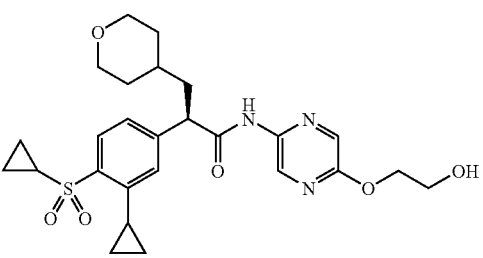
TABLE 45
23
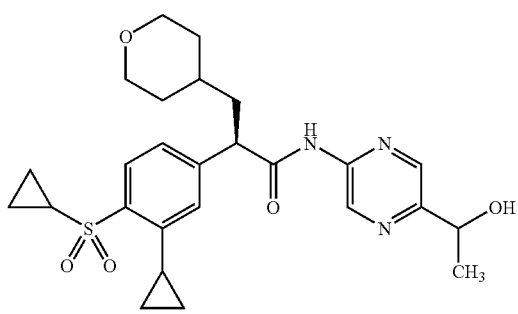
91
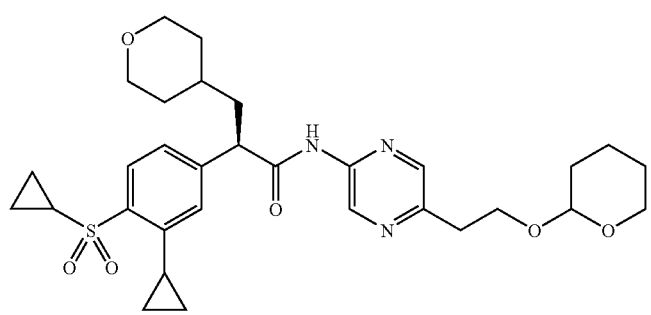
14
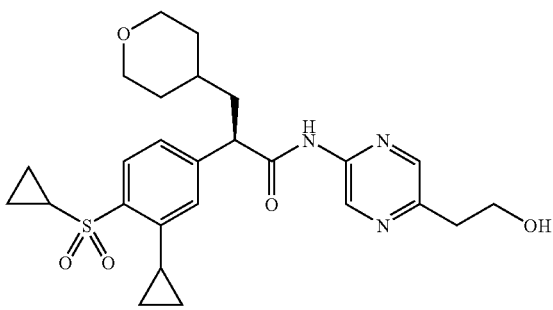

TABLE 45-continued
17 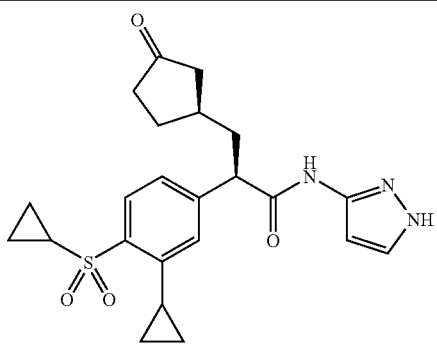
92 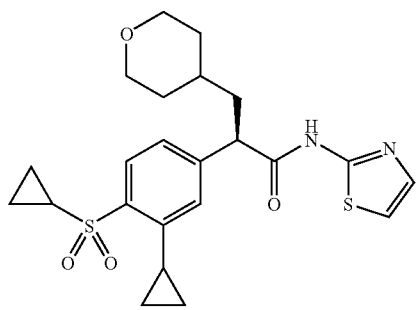
TABLE 46
93 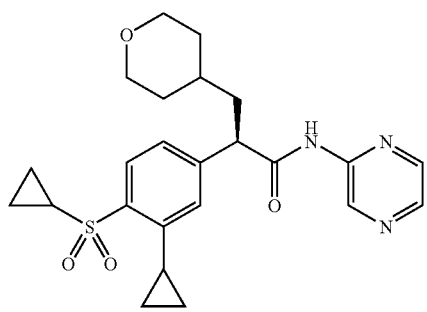
94 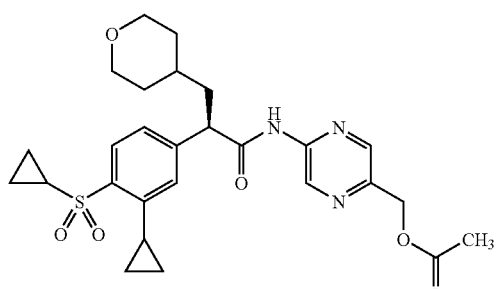
95 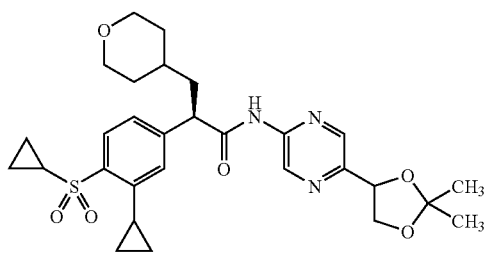
TABLE 46-continued
13 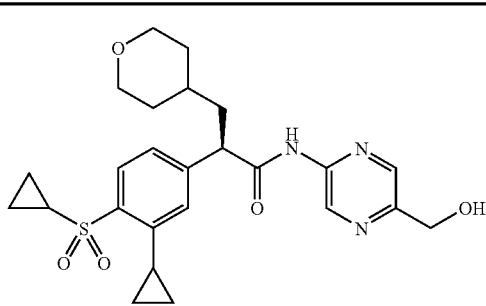
18 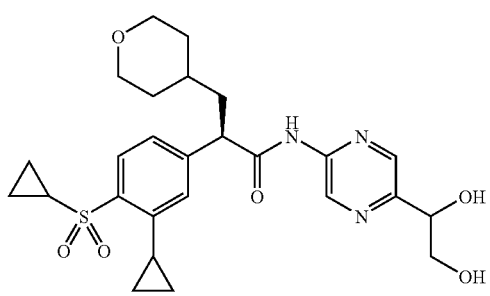

TABLE 47
96
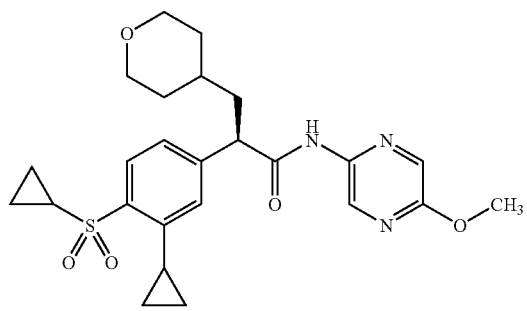
97
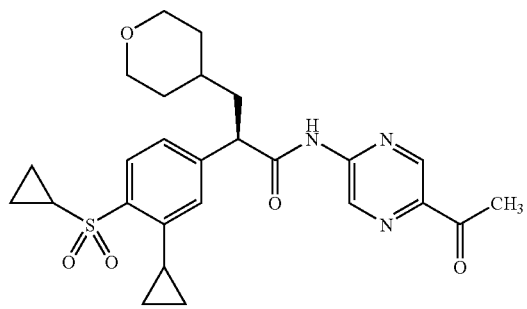
98
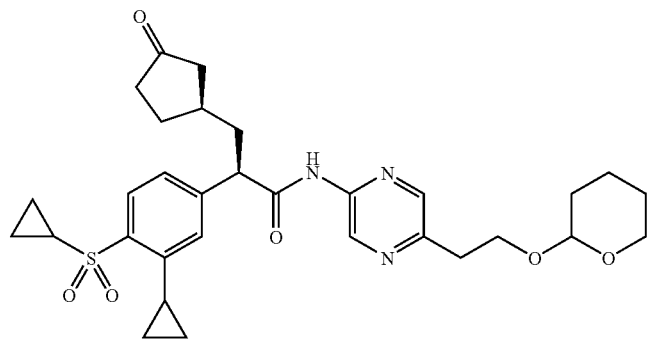
15
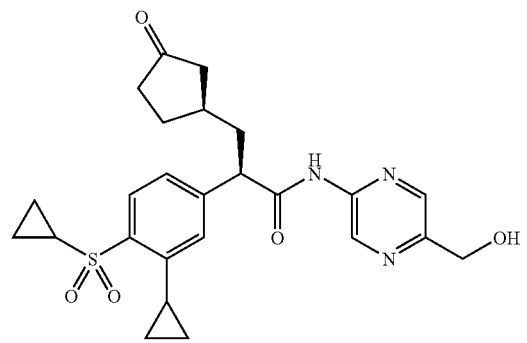
99
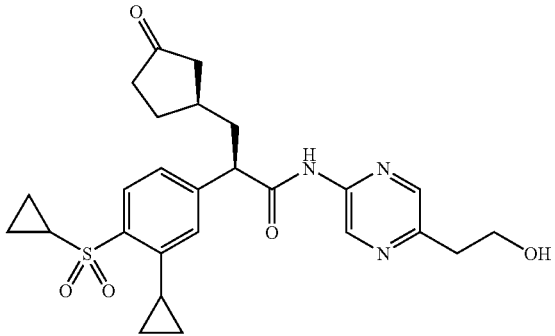

TABLE 48

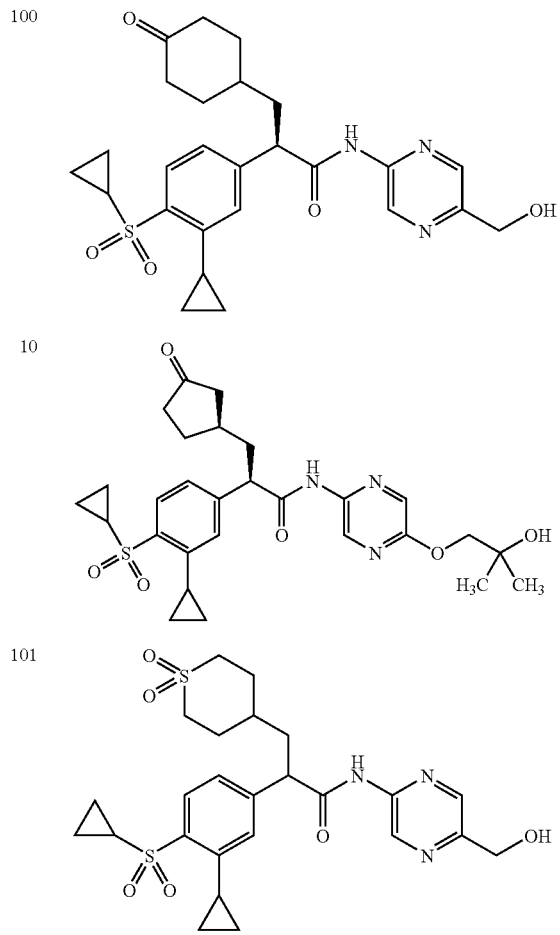

TABLE 48-continued

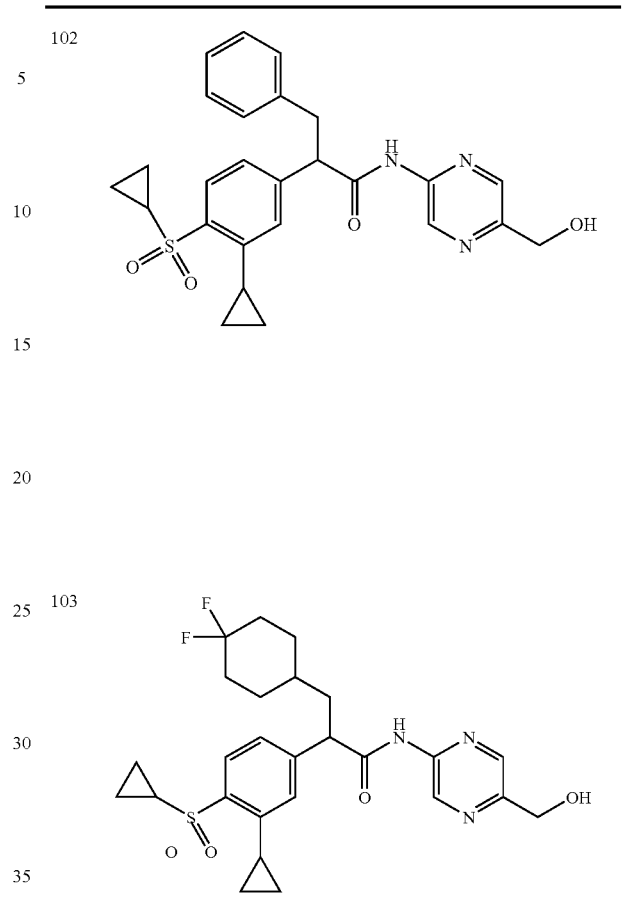

TABLE 49

| Ex | Syn | Data |
|---|---|---|
| 24 | 2 | NMR2: 0.85-0.92 (2H, m), 1.09-1.24 (4H, m), 1.36-1.78 (10H, m), 2.10-2.27 (1H, m), 2.82-2.93 (1H, m), 2.94-3.06 (1H, m), 3.75 (3H, s), 6.77 (1H, d, J = 2.2 Hz), 6.85 (1H, d, J = 1.5 Hz), 7.04 (1H, d, J = 10.9 Hz), 7.20 (1H, dd, J = 7.7, 1.5 Hz), 7.25 (1H, d, J = 2.2 Hz), 7.47 (1H, br), 8.00 (1H, d, J = 7.7 Hz)<br>ESI+: 440 |
| 1 | 1 | NMR2: 0.83-0.93 (2H, m), 1.09-1.23 (4H, m), 1.35-1.81 (10H, m), 1.93-2.06 (2H, m), 2.15-2.29 (1H, m), 2.83-2.94 (1H, m), 2.96-3.05 (1H, m), 3.58 (2H, t, J = 5.7 Hz), 4.13 (2H, t, J = 5.7 Hz), 6.76 (1H, d, J = 2.3 Hz), 6.86 (1H, d, J = 1.3 Hz), 7.01 (1H, d, J = 10.7 Hz), 7.20 (1H, dd, J = 8.0, 1.3 Hz), 7.31 (1H, d, J = 2.3 Hz), 7.50 (1H, br s), 8.00 (1H, d, J = 8.0 Hz)<br>ESI+: 484 |
| 2 | 2 | NMR2: 0.82-0.90 (2H, m), 1.11-1.30 (4H, m), 1.36-1.48 (3H, m), 1.54-1.71 (3H, m), 2.02-2.18 (1H, m), 2.84-2.95 (1H, m), 2.95-3.07 (1H, m), 3.27 (2H, br t, J = 11.8 Hz), 3.76 (3H, s), 3.91 (2H, br d, J = 10.1 Hz), 6.77 (1H, d, J = 2.2 Hz), 6.84 (1H, br s), 6.95 (1H, d, J = 10.3 Hz), 7.19 (1H, dd, J = 8.0, 1.4 Hz), 7.26 (1H, d, J = 3.0 Hz), 7.49 (1H, br s), 8.03 (1H, d, J = 8.1 Hz)<br>ESI+: 456 |
| 25 | 2 | NMR2: 0.84-0.92 (2H, m), 1.10-1.28 (4H, m), 1.39-1.47 (2H, m), 1.75-1.90 (1H, m), 1.93-2.06 (1H, m), 2.54-2.70 (1H, m), 2.83-2.93 (1H, m), 2.95-3.06 (1H, m), 3.54 (1H, br t, J = 7.7 Hz), 3.69-3.82 (2H, m), 3.76 (3H, s), 3.93 (1H, dt, J = 4.5, 8.3 Hz), 6.76 (1H, d, J = 2.2 Hz), 6.84 (1H, br s), 7.05 (1H, d, J = 10.5 Hz), 7.19 (1H, dd, J = 8.0, 1.6 Hz), 7.25 (1H, d, J = 2.3 Hz), 7.45 (1H, br s), 8.03 (1H, d, J = 8.0 Hz)<br>ESI+: 442 |

TABLE 49-continued

| Ex | Syn | Data |
|---|---|---|
| 25 | 2 | NMR2: 0.82-0.92 (2H, m), 1.13-1.30 (4H, m), 1.38-1.49 (3H, m), 1.53-1.72 (3H, m), 2.06-2.22 (1H, m), 2.84-2.96 (1H, m), 2.97-3.09 (1H, m), 3.28 (2H, dt, J = 1.8, 10.4 Hz), 3.92 (2H, dd, J = 9.1, 2.8 Hz), 6.83 (1H, br s), 7.08 (1H, d, J = 10.5 Hz), 7.18 (1H, dd, J = 8.0, 1.6 Hz), 7.24 (1H, s), 8.07 (1H, d, J = 8.1 Hz), 8.35 (1H, br s)<br>ESI+: 493, 495 |

TABLE 50

| Ex | Syn | Data |
|---|---|---|
| 27 | 2 | NMR2: 0.82-0.93 (2H, m), 1.10-1.33 (4H, m), 1.39-1.48 (2H, m), 1.76-1.92 (1H, m), 1.95-2.10 (1H, m), 2.58-2.75 (1H, m), 2.83-2.94 (1H, m), 2.96-3.09 (1H, m), 3.57 (1H, br t, J = 8.0 Hz), 3.70-3.84 (2H, m), 3.89-4.02 (1H, m), 6.84 (1H, d, J = 0.9 Hz), 7.19 (1H, d, J = 10.6 Hz), 7.20 (1H, d, J = 1.8 Hz), 7.25 (1H, d, J = 7.0 Hz), 8.07 (1H, d, J = 8.1 Hz), 8.30-8.42 (1H, br)<br>ESI+: 479, 481 |
| 28 | 2 | NMR2: 0.82-0.92 (2H, m), 1.10-1.32 (4H, m), 1.39-1.50 (3H, m), 1.54-1.73 (3H, m), 2.07-2.24 (1H, m), 2.53 (3H, s), 2.83-2.94 (1H, m), 2.96-3.08 (1H, m), 3.29 (2H, dt, J = 2.1, 11.9 Hz), 3.93 (2H, dd, J = 11.8, 2.4 Hz), 6.87 (1H, d, J = 1.6 Hz), 6.99 (1H, d, J = 10.4 Hz), 7.22 (1H, dd, J = 8.0, 1.7 Hz), 7.51 (1H, br s), 8.05 (1H, s), 8.06 (1H, d, J = 8.1 Hz), 9.50 (1H, d, J = 1.4 Hz)<br>ESI+: 468 |
| 29 | 2 | NMR2: 0.84-0.94 (2H, m), 1.09-1.30 (4H, m), 1.38-1.46 (2H, m), 1.77-1.93 (1H, m), 1.96-2.11 (1H, m), 2.53 (3H, s), 2.60-2.76 (1H, m), 2.82-2.94 (1H, m), 2.96-3.09 (1H, m), 3.57 (1H, br t, J = 7.9 Hz), 3.71-3.86 (2H, m), 3.90-4.01 (1H, m), 6.87 (1H, s), 7.10 (1H, d, J = 10.4 Hz), 7.22 (1H, br d, J = 7.7 Hz), 7.49 (1H, br s), 8.05 (1H, s), 8.07 (1H, d, J = 8.3 Hz), 9.49 (1H, s)<br>ESI+: 454 |
| 3 | 3 | NMR2: 0.82-0.99 (2H, m), 1.05-1.29 (4H, m), 1.36-1.82 (10H, m), 2.12 (1H, t, J = 6.5 Hz), 2.16-2.31 (1H, m), 2.82-2.94 (1H, m), 2.95-3.05 (1H, m), 3.09 (1H, d, J = 4.2 Hz), 3.46-3.70 (2H, m), 3.94-4.06 (1H, m), 4.07-4.13 (2H, m), 6.79 (1H, d, J = 2.1 Hz), 6.86 (1H, d, J = 1.5 Hz), 7.02 (1H, d, J = 10.5 Hz), 7.21 (1H, dd, J = 7.9, 1.5 Hz), 7.34 (1H, d, J = 2.1 Hz), 7.44 (1H, br s), 8.02 (1H, d, J = 7.9 Hz)<br>ESI+: 500 |
| 30 | 3 | NMR2: 0.82-0.99 (2H, m), 1.05-1.29 (4H, m), 1.36-1.82 (10H, m), 2.16-2.31 (1H, m), 2.82-2.94 (1H, m), 2.95-3.05 (1H, m), 3.09 (1H, br s), 3.46-3.70 (2H, m), 3.94-4.06 (1H, m), 4.07-4.13 (2H, m), 6.79 (1H, d, J = 2.1 Hz), 6.86 (1H, d, J = 1.5 Hz), 7.02 (1H, d, J = 10.5 Hz), 7.21 (1H, dd, J = 7.9, 1.5 Hz), 7.34 (1H, d, J = 2.1 Hz), 7.44 (1H, br s), 8.02 (1H, d, J = 7.9 Hz)<br>ESI+: 500 |
| 31 | 2 | ESI+: 466 |
| 32 | 2 | FAB+: 454 |
| 33 | 2 | FAB+: 491 |

TABLE 51

| Ex | Syn | Data |
|---|---|---|
| 34 | 2 | NMR2: 0.83-0.93 (2H, m), 1.11-1.32 (5H, m), 1.40-1.48 (2H, m), 1.79-1.96 (1H, m), 2.03-2.24 (3H, m), 2.26-2.46 (1H, m), 2.54 (3H, s), 2.61-2.77 (1H, m), 2.84-2.95 (1H, m), 2.96-3.09 (1H, m), 6.90 (1H, d, J = 1.6 Hz), 7.13 (1H, d, J = 10.2 Hz), 7.25 (1H, dd, J = 8.0, 1.6 Hz), 7.51 (1H, br s), 8.06 (1H, br s), 8.09 (1 H, d, J = 8.1 Hz), 9.51 (1H, d, J = 1.3 Hz)<br>ESI+: 466 |
| 35 | 2 | NMR2: 0.82-0.92 (2H, m), 1.12-1.32 (4H, m), 1.40-1.50 (1H, m), 1.54-1.69 (3H, br), 1.98-2.22 (3H, m), 2.24-2.44 (1H, m), 2.58-2.75 (1H, m), 2.84-3.08 (2H, m), 6.86 (1H, d, J = 1.4 Hz), 7.19 (1H, d, J = 10.2 Hz), 7.20 (1H, dd, J = 8.1, 1.6 Hz), 7.24 (1H, s), 8.08 (1H, d, J = 8.0 Hz), 8.4-8.6 (1H, br)<br>FAB+: 491, 493 |
| 36 | 2 | NMR2: 0.82-0.93 (2H, m), 1.11-1.30 (5H, m), 1.39-1.47 (2H, m), 1.80-1.92 (1H, m), 2.00-2.21 (3H, m), 2.25-2.46 (1H, m), 2.53 (3H, s), 2.61-2.76 (1H, m), 2.83-2.94 (1H, m), 2.96-3.08 (1H, m), 6.89 (1H, br s), 7.12 (1H, d, J = 10.3 Hz), 7.24 (1H, dd, J = 8.1, 1.6 Hz), 7.50 (1H, br s), 8.05 (1H, br s), 8.08 (1H, d, J = 8.1 Hz), 9.50 (1H, br s)<br>ESI+: 466 |
| 37 | 2 | NMR2: 0.82-0.92 (2H, m), 1.11-1.29 (4H, m), 1.39-1.47 (2H, m), 1.74-1.92 (1H, m), 1.98-2.20 (3H, m), 2.22-2.43 (2H, m), 2.52-2.70 (1H, m), 2.84-2.94 (1H, m), 2.95-3.06 (1H, m), 3.76 (3H, s), 6.76 (1H, d, J = 2.3 Hz), 6.86 (1H, d, J = 1.5 Hz), 7.06 (1H, d, J = 10.2 Hz), 7.20 (1H, dd, J = 8.1, 1.7 Hz), 7.26 (1H, d, J = 2.6 Hz), 7.49 (1H, br s), 8.04 (1H, d, J = 8.0 Hz)<br>ESI+: 454 |

TABLE 51-continued

| | | |
|---|---|---|
| 38 | 3 | ESI+: 512 |
| 6 | 6 | ESI+: 482 |
| 4-1 | 4 | NMR2: 0.82-0.92 (2H, m), 1.11-1.29 (4H, m), 1.38-1.47 (2H, m), 1.74-1.93 (1H, m), 1.98-2.20 (3H, m), 2.22-2.43 (2H, m), 2.52-2.70 (1H, m), 2.83-2.94 (1H, m), 2.95-3.07 (1H, m), 3.76 (3H, s), 6.76 (1H, d, J = 2.2 Hz), 6.86 (1H, br s), 7.07 (1H, d, J = 10.2 Hz), 7.20 (1H, dd, J = 8.0, 1.6 Hz), 7.26 (1H, d, J = 2.3 Hz), 7.47 (1H, br s), 8.04 (1H, d, J = 8.1 Hz) ESI+: 454 |
| 4-2 | 4 | FAB+: 454 |

TABLE 52

| | | |
|---|---|---|
| 39 | 4 | NMR2: 0.82-0.97 (2H, m), 1.13-1.32 (4H, m), 1.39-1.51 (2H, m), 1.77-1.98 (1H, m), 1.99-2.48 (5H, m), 2.54 (3H, s), 2.58-2.76 (1H, m), 2.82-2.96 (1H, m), 2.97-3.13 (1H, m), 6.87 (1H, d, J = 1.7 Hz), 7.16-7.32 (2H, m), 7.98 (1H, s), 8.10 (1H, d, J = 8 Hz), 8.55 (1H, br) ESI+: 499 |
| 40 | 4 | NMR2: 0.82-0.98 (2H, m), 1.09-1.32 (4H, m), 1.38-1.53 (2H, m), 1.74-1.96 (1H, m), 1.99-2.48 (5H, m), 2.55-2.77 (1H, m), 2.83-2.97 (1H, m), 2.98-3.12 (1H, m), 6.88 (1H, s), 7.03 (1H, d, J = 3.5 Hz), 7.16-7.29 (2H, m), 7.42 (1H, d, J = 3.5 Hz), 8.08 (1H, d, J = 8.1 Hz), 8.50 (1H, br) ESI+: 457 |
| 41 | 4 | NMR2: 0.80-0.99 (2H, m), 1.11-1.35 (4H, m), 1.37-1.51 (2H, m), 1.76-1.96 (1H, m), 2.00-2.49 (5H, m), 2.55-2.75 (1H, m), 2.84-2.97 (1H, m), 2.98-3.10 (1H, m), 6.86 (1H, s), 7.16-7.32 (3H, m), 8.09 (1H, d, J = 7.9 Hz), 8.32 (1H, br) ESI+: 491 |
| 42 | 4 | NMR2: 0.83-0.93 (2H, m), 1.11-1.30 (4H, m), 1.39-1.50 (2H, m), 1.74-1.95 (1H, m), 1.98-2.46 (5H, m), 2.56-2.72 (1H, m), 2.81-3.11 (2H, m), 6.85 (1H, s), 7.00 (1H, d, J = 2.8 Hz), 7.12-7.23 (2H, m), 8.08 (1H, d, J = 8.2 Hz), 8.16 (1H, br) ESI+: 475 |
| 43 | 4 | NMR2: 0.78-0.98 (2H, m), 1.08-1.33 (4H, m), 1.38-1.51 (2H, m), 1.73-1.97 (1H, m), 2.00-2.52 (5H, m), 2.58-2.78 (1H, m), 2.82-3.18 (2H, m), 3.69-3.87 (2H, m), 4.62-4.76 (1H, m), 6.87 (1H, s), 6.93 (1H, s), 7.13-7.30 (2H, m), 8.10 (1H, d, J = 7.9 Hz), 8.66 (1H, br) ESI+: 517 |
| 44 | 4 | NMR2: 0.83-1.03 (2H, m), 1.14-1.35 (4H, m), 1.45-1.55 (2H, m), 1.78-1.99 (1H, m), 2.01-2.48 (5H, m), 2.56 (3H, s), 2.60-2.75 (1H, m), 2.88-3.14 (2H, m), 6.88 (1H, s), 7.18-7.33 (2H, m), 7.82 (1H, s), 8.13 (1H, d, J = 8.1 Hz), 8.56 (1H, br) ESI+: 499 |
| 45 | 4 | NMR2: 0.84-1.00 (2H, m), 1.03-1.24 (4H, m), 1.33-1.46 (2H, m), 1.93-2.43 (6H, m), 2.47 (3H, s), 2.70-3.12 (3H, m), 6.88 (1H, s), 7.19 (1H, d, J = 8.2 Hz), 7.38 (1H, d, J = 10.0 Hz), 7.95 (1H, s), 8.00-8.10 (2H, m), 8.76 (1H, d, J = 8.8 Hz), 11.9 (1H, br) ESI+: 465 |

TABLE 53

| | | |
|---|---|---|
| 46 | 4 | NMR2: 0.79-0.98 (2H, m), 1.10-1.35 (4H, m), 1.38-1.53 (2H, m), 1.75-1.95 (1H, m), 1.97-2.50 (5H, m), 2.56-2.74 (1H, m), 2.82-3.14 (2H, m), 5.29 (2H, d, J = 47.6 Hz), 6.87 (1H, s), 7.05 (1H, d, J = 3.3 Hz), 7.16-7.29 (2H, m), 8.08 (1H, d, J = 8.0 Hz), 8.48 (1H, br) ESI+: 489 |
| 5 | 5 | NMR1: 0.82-0.99 (2H, m), 1.01-1.27 (6H, m), 1.78-2.41 (6H, m), 2.72-2.92 (2H, m), 3.05-3.18 (1H, m), 6.78 (1H, d, J = 10.4 Hz), 6.96 (1H, d, J = 1.6 Hz), 7.28 (1H, dd, J = 8.0, 1.6 Hz), 7.86 (1H, d, J = 8.0 Hz), 8.16 (1H, d, J = 8.4 Hz), 8.27 (1H, dd, J = 8.4, 2.4 Hz), 8.84 (1H, d, J = 2.4 Hz), 10.72 (1H, s) ESI+: 495 |
| 7 | 7 | NMR2: 0.81-1.00 (2H, m), 1.12-1.31 (4H, m), 1.40-1.51 (2H, m), 1.74-1.96 (1H, m), 2.06-3.12 (8H, m), 3.93-4.05 (2H, m), 4.49-4.57 (2H, m), 6.87 (1H, d, J = 8.7 Hz), 6.89 (1H, s), 7.20-7.30 (2H, m), 7.82 (1H, d, J = 8.7 Hz), 8.10 (1H, d, J = 8.0 Hz), 8.39 (1H, br) ESI−: 566 |
| 47 | 4 | NMR2: 0.83-0.93 (2H, m), 1.11-1.30 (4H, m), 1.39-1.50 (2H, m), 1.74-1.95 (1H, m), 1.98-2.46 (5H, m), 2.56-2.72 (1H, m), 2.81-3.11 (2H, m), 6.85 (1H, s), 7.00 (1H, d, J = 2.8 Hz), 7.12-7.23 (2H, m), 8.08 (1H, d, J = 8.2 Hz), 8.16 (1H, br s) ESI+: 475 |
| 48 | 4 | ESI+: 471 |
| 21 | 21 | ESI+: 531 |
| 49 | 4 | ESI+: 440 |
| 50 | 4 | FAB+: 428 |

TABLE 53-continued

| | | |
|---|---|---|
| 51 | 9 | NMR2: 0.82-0.94 (2H, m), 1.01-1.12 (2H, m), 1.13-1.24 (2H, m), 1.30-1.42 (2H, m), 1.52-1.67 (1H, m), 1.81-2.49 (8H, m), 2.57 (3H, s), 2.76-2.89 (1H, m), 2.91-3.03 (1H, m), 3.77 (1H, t, J = 7.4 Hz), 6.95 (1H, s), 7.22-7.32 (1H, m), 7.81 (1H, s), 7.96 (1H, d, J = 8.0 Hz), 8.31 (1H, br s) ESI+: 501 |
| 52 | 9 | NMR2: 0.78-0.95 (2H, m), 1.00-1.12 (2H, m), 1.13-1.23 (2H, m), 1.29-1.43 (2H, m), 1.47-1.69 (1H, m), 1.76-2.50 (8H, m), 2.78-2.89 (1H, m), 2.90-3.00 (1H, m), 3.76 (1H, t, J = 7.1 Hz), 6.96 (1H, s), 7.23-7.32 (1H, m), 7.67 (1H, s), 7.94 (1H, d, J = 8.2 Hz), 9.58 (1H, br s) ESI+: 484 |

TABLE 54

| | | |
|---|---|---|
| 53 | 9 | NMR2: 0.80-0.94 (2H, m), 1.01-1.03 (2H, m), 1.14-1.22 (2H, m), 1.30-1.41 (2H, m), 1.48-2.44 (9H, m), 2.78-2.88 (1H, m), 2.89-3.01 (1H, m), 3.72 (1H, t, J = 7.7 Hz), 6.93 (1H, s), 7.20-7.34 (1H, m), 7.92 (1H, s), 7.94 (1H, d, J = 8.1 Hz), 9.43 (1H, br s) ESI+: 484 |
| 9 | 9 | NMR2: 0.88-1.41 (8H, m), 1.42-2.57 (12H, m), 2.75-2.86 (1H, m), 2.87-2.99 (1H, m), 4.05 (1H, t, J = 7.1 Hz), 7.19-7.32 (1H, m), 7.40 (1H, d, J = 8.8 Hz), 7.90 (1H, d, J = 8.8 Hz), 7.93 (1H, s), 8.05 (1H, d, J = 8.1 Hz), 8.57 (1H, d, J = 8.1 Hz), 13.01 (1H, br s) ESI+: 467 |
| 54 | 9 | NMR2: 0.83-1.41 (8H, m), 1.45-2.52 (9H, m), 2.73-2.87 (1H, m), 2.88-3.10 (1H, m), 3.72 (1H, t, J = 7.7 Hz), 3.93 (3H, s), 6.84 (1H, s), 7.05 (1H, s), 7.33 (1H, d, J = 7.7 Hz), 7.39 (1H, s), 7.91 (1H, d, J = 7.7 Hz), 9.76 (1H, br s) ESI+: 456 |
| 55 | 9 | NMR2: 0.82-0.96 (2H, m), 0.98-1.12 (2H, m), 1.13-1.24 (2H, m), 1.29-1.44 (2H, m), 1.46-2.46 (9H, m), 2.52 (3H, s), 2.75-2.87 (1H, m), 2.89-3.03 (1H, m), 3.59 (1H, t, J = 7.2 Hz), 6.98 (1H, d, J = 1.7 Hz), 7.30 (1H, dd, J = 8.1, 1.7 Hz), 7.68 (1H, br s), 7.94 (1H, d, J = 8.1 Hz), 8.07 (1H, s), 9.38 (1H, s) ESI+: 468 |
| 56 | 12 | NMR1: 0.81-0.95 (2H, m), 1.00-1.11 (4H, m), 1.12-1.22 (2H, m), 1.38 (6H, s), 1.41-1.62 (1H, m), 1.74-2.40 (8H, m), 2.68-2.88 (1H, m), 2.95-3.10 (1H, m), 3.94-4.07 (1H, m), 7.12 (1H, d, J = 1.4 Hz), 7.39 (1H, dd, J = 8.2, 1.4 Hz), 7.52 (1H, s), 7.81 (1H, d, J = 8.2 Hz), 8.32 (1H, s), 12.62 (1H, s) ESI+: 577 |
| 57 | 12 | NMR1: 0.78-0.94 (2H, m), 0.96-1.11 (4H, m), 1.12-1.25 (2H, m), 1.38-1.63 (1H, m), 1.69-2.48 (8H, m), 2.69-2.89 (1H, m), 2.90-3.09 (1H, m), 4.08 (1H, t, J = 8.2 Hz), 7.18 (1H, d, J = 1.4 Hz), 7.41 (1H, dd, J = 8.2, 1.4 Hz), 7.79 (1H, d, J = 8.2 Hz), 8.16 (1H, d, J = 8.8 Hz), 8.24 (1H, dd, J = 8.8, 2.3 Hz), 8.81 (1H, d, J = 2.3 Hz), 11.17 (1H, br s) ESI+: 497 |
| 58 | 12 | NMR3: 0.85-0.96 (2H, m), 0.99-1.10 (2H, m), 1.11-1.23 (2H, m), 1.27-1.40 (2H, m), 1.46-1.70 (1H, m), 1.78-3.02 (10H, m), 3.82 (1H, t, J = 7.7 Hz), 4.94 (2H, s), 6.91 (1H, d, J = 8.8 Hz), 7.08 (1H, s), 7.35 (1H, d, J = 8.8 Hz), 7.85 (1H, d, J = 8.7 Hz), 7.90 (1H, d, J = 8.7 Hz) ESI+: 584 |

TABLE 55

| | | |
|---|---|---|
| 59 | 9 | NMR2: 0.76-0.94 (2H, m), 0.99-1.10 (2H, m), 1.11-1.21 (2H, m), 1.28-1.38 (2H, m), 1.43-2.44 (9H, m), 2.76-2.85 (1H, m), 2.88-2.98 (1H, m), 3.67 (1H, t, J = 7.5 Hz), 6.99 (1H, d, J = 11.6 Hz), 7.19-7.33 (2H, m), 7.44 (1H, br s), 7.89 (1H, d, J = 8.2 Hz), 9.31 (1H, br s) ESI+: 443 |
| 60 | 9 | NMR2: 0.69-0.93 (2H, m), 0.95-1.08 (2H, m), 1.09-1.19 (2H, m), 1.26-1.39 (2H, m), 1.49-1.66 (1H, m), 1.73-2.50 (8H, m), 2.72-2.84 (1H, m), 2.85-3.00 (1H, m), 3.71 (1H, t, J = 7.4 Hz), 7.02 (1H, d, J = 1.5 Hz), 7.15 (1H, d, J = 1.5 Hz), 7.33 (1H, dd, J = 8.2, 1.5 Hz), 7.90 (1H, d, J = 8.2 Hz), 8.37 (1H, d, J = 1.5 Hz), 9.67 (1H, br s) ESI+: 443 |
| 61 | 2 | FAB+: 476 |
| 62 | 9 | NMR2: 0.77-0.99 (2H, m), 1.01-1.21 (4H, m), 1.29-1.47 (2H, m), 1.52-2.65 (12H, m), 2.78-2.91 (1H, m), 2.92-3.05 (1H, m), 3.76 (1H, t, J = 7.3 Hz), 6.84 (1H, s), 7.09 (1H, s), 7.25-7.49 (1H, m), 7.96 (1H, d, J = 8.2 Hz), 9.77 (1H, br s) ESI+: 457 |

TABLE 55-continued

| | | |
|---|---|---|
| 63 | 9 | NMR2: 0.82-0.97 (2H, m), 0.98-1.11 (2H, m), 1.13-1.25 (2H, m), 1.28-1.42 (2H, m), 1.52-2.47 (9H, m), 2.76-2.89 (1H, m), 2.90-3.03 (1H, m), 3.60 (1H, t, J = 7.5 Hz), 6.97 (1H, d, J = 1.6 Hz), 7.18-7.38 (1H, m), 7.91 (1H, br s), 7.96 (1H, d, J = 8.2 Hz), 8.16 (1H, dd, J = 8.2, 1.6 Hz), 8.66 (1H, d, J = 5.7 Hz), 8.84 (1H, d, J = 1.2 Hz)<br>ESI+: 454 |
| 64 | 9 | NMR2: 0.79-0.98 (2H, m), 1.01-1.14 (2H, m), 1.15-1.28 (2H, m), 1.29-1.44 (2H, m), 1.50-2.45 (9H, m), 2.51 (3H, s), 2.78-2.90 (1H, m), 2.91-3.02 (1H, m), 3.74 (1H, t, J = 7.7 Hz), 6.93 (1H, d, J = 1.7 Hz), 7.18-7.35 (1H, m), 7.96 (1H, d, J = 8.1 Hz), 9.18 (1H, br s)<br>ESI+: 474 |
| 65 | 9 | NMR2: 0.58-0.75 (1H, m), 0.79-1.18 (5H, m), 1.21-1.38 (2H, m), 1.49-2.58 (9H, m), 2.67-2.80 (1H, m), 2.81-2.94 (1H, m), 4.40 (1H, t, J = 7.6 Hz), 7.20-7.36 (1H, m), 7.49 (1H, dd, J = 8.2, 1.6 Hz), 7.86 (1H, d, J = 8.2 Hz), 8.96 (1H, s), 13.93 (1H, br s)<br>ESI+: 460 |
| 66 | 2 | FAB+: 488 |
| 67 | 2 | FAB+: 479 |

TABLE 56

| | | |
|---|---|---|
| 68 | 9 | NMR2: 0.84-0.97 (2H, m), 0.98-1.12 (2H, m), 1.13-1.25 (2H, m), 1.29-1.41 (2H, m), 1.49-2.50 (9H, m), 2.75-2.89 (1H, m), 2.90-3.03 (1H, m), 3.62 (1H, t, J = 7.1 Hz), 7.00 (1H, d, J = 1.6 Hz), 7.20-7.37 (1H, m), 7.75 (1H, br s), 7.96 (1H, d, J = 8.1 Hz), 8.20-8.24 (1H, m), 8.37 (1H, d, J = 2.5 Hz), 9.53 (1H, br s)<br>ESI+: 454 |
| 69 | 9 | NMR2: 0.82-0.95 (2H, m), 0.97-1.12 (2H, m), 1.13-1.26 (2H, m), 1.30-1.42 (2H, m), 1.47-2.45 (9H, m), 2.75-2.87 (1H, m), 2.89-3.02 (1H, m), 3.61 (1H, t, J = 7.4 Hz), 6.97 (1H, d, J = 1.7 Hz), 7.17-7.40 (1H, m), 7.77 (1H, br s), 7.95 (1H, d, J = 8.3 Hz), 8.30 (1H, d, J = 1.5 Hz), 9.31 (1H, d, J = 1.5 Hz)<br>ESI+: 532, 534 |
| 20 | 20 | diastereo mixture<br>FAB+: 456 |
| 8 | 8 | diastereo mixture<br>FAB+: 458 |
| 70 | 9 | NMR1: 0.80-0.95 (2H, m), 0.98-1.10 (4H, m), 1.11-1.25 (2H, m), 1.42-1.61 (1H, m), 1.77-2.35 (8H, m), 2.68-2.86 (1H, m), 2.96-3.07 (1H, m), 3.98-4.17 (1H, m), 7.16 (1H, d, J = 1.3 Hz), 7.41 (1H, dd, J = 8.2, 1.3 Hz), 7.80 (1H, d, J = 8.2 Hz), 8.55 (1H, d, J = 1.4 Hz), 9.13 (1H, d, J = 1.4 Hz), 11.29 (1H, br s)<br>ESI+: 488, 490 |
| 71 | 9 | NMR2: 0.81-0.97 (2H, m), 1.00-1.13 (2H, m), 1.14-1.26 (2H, m), 1.28-1.41 (2H, m), 1.50-2.48 (9H, m), 2.76-2.88 (1H, m), 2.90-3.03 (1H, m), 3.70 (1H, t, J = 7.8 Hz), 6.99 (1H, d, J = 1.7 Hz), 7.16-7.40 (1H, m), 7.95 (1H, d, J = 8.2 Hz), 8.38 (1H, d, J = 1.5 Hz), 8.42 (1H, br s), 9.63 (1H, d, J = 1.5 Hz)<br>ESI+: 479 |
| 72 | 9 | NMR1: 0.77-0.94 (2H, m), 0.97-1.11 (4H, m), 1.12-1.24 (2H, m), 1.39-2.36 (9H, m), 2.68-2.90 (1H, m), 2.92-3.10 (1H, m), 3.87 (3H, s), 4.02 (1H, t, J = 6.8 Hz), 7.16 (1H, d, J = 1.3 Hz), 7.41 (1H, dd, J = 8.3, 1.3 Hz), 7.79 (1H, d, J = 8.3 Hz), 8.10 (1H, d, J = 1.5 Hz), 8.84 (1H, d, J = 1.5 Hz), 10.86 (1H, br s)<br>ESI+: 484 |
| 73 | 9 | NMR1: 0.81-0.96 (2H, m), 0.97-1.10 (4H, m), 1.11-1.23 (2H, m), 1.43-2.42 (9H, m), 2.68-2.88 (1H, m), 2.93-3.10 (1H, m), 3.88 (3H, s), 4.10 (1H, t, J = 7.5 Hz), 7.17 (1H, d, J = 1.6 Hz), 7.42 (1H, dd, J = 8.0, 1.6 Hz), 7.81 (1H, d, J = 8.0 Hz), 8.97 (1H, d, J = 1.5 Hz), 9.41 (1H, d, J = 1.5 Hz), 11.52 (1H, br s)<br>ESI+: 512 |

TABLE 57

| | | |
|---|---|---|
| 74 | 9 | NMR1: 0.77-0.96 (2H, m), 0.98-1.10 (4H, m), 1.12-1.27 (2H, m), 1.41-2.39 (9H, m), 2.58 (3H, s), 2.69-2.88 (1H, m), 2.93-3.09 (1H, m), 4.10 (1H, t, J = 7.2 Hz), 7.17 (1H, d, J = 1.7 Hz), 7.43 (1H, dd, J = 8.2, 1.7 Hz), 7.81 (1H, d, J = 8.2 Hz), 8.88 (1H, d, J = 1.5 Hz), 9.38 (1H, d, J = 1.5 Hz), 11.51 (1H, d)<br>ESI+: 496 |
| 75 | 9 | NMR1: 0.80-0.95 (2H, m), 1.00-1.10 (4H, m), 1.11-1.22 (2H, m), 1.41 (3H, s), 1.43 (3H, s), 1.46-2.36 (9H, m), 2.73-2.88 (1H, m), 2.93-3.10 (1H, m), 4.05 (1H, t, J = 8.2 Hz), 5.38 (1H, s), 7.17 (1H, d, J = 1.6 Hz), 7.42 (1H, dd, J = 8.3, 1.6 Hz), 7.80 (1H, d, J = 8.3 Hz), 8.60 (1H, d, J = 1.5 Hz), 9.18 (1H, d, J = 1.5 Hz), 11.05 (1H, br s)<br>ESI+: 512 |

TABLE 57-continued

| | | |
|---|---|---|
| 76 | 12 | NMR1: 0.80-0.96 (2H, m), 0.99-1.27 (6H, m), 1.39-1.64 (1H, m), 1.74-2.39 (8H, m), 2.71-2.87 (1H, m), 2.93-3.09 (1H, m), 4.10 (1H, t, J = 7.3 Hz), 7.17 (1H, d, J = 1.3 Hz), 7.43 (1H, dd, J = 8.3, 1.3 Hz), 7.81 (1H, d, J = 8.3 Hz), 8.94 (1H, d, J = 1.4 Hz), 9.40 (1H, d, J = 1.4 Hz), 11.47 (1H, br s), 13.46 (1H, br s) ESI+: 498 |
| 19 | 19 | NMR1: 0.82-0.94 (2H, m), 1.02-1.10 (4H, m), 1.11-1.28 (2H, m), 1.42-1.64 (1H, m), 1.79-2.34 (8H, m), 2.72-2.87 (1H, m), 2.99 (3H, s), 3.00 (3H, s), 2.95-3.07 (1H, m), 4.09 (1H, t, J = 6.9 Hz), 7.18 (1H, d, J = 1.5 Hz), 7.42 (1H, dd, J = 8.3, 1.5 Hz), 7.80 (1H, d, J = 8.3 Hz), 8.60 (1H, d, J = 1.5 Hz), 9.28 (1H, d, J = 1.5 Hz), 11.31 (1H, br s) ESI+: 525 |
| 77 | 9 | NMR1: 0.80-0.95 (2H, m), 0.99-1.11 (4H, m), 1.12-1.23 (2H, m), 1.41-2.40 (9H, m), 2.67-2.90 (1H, m), 2.94-3.10 (1H, m), 3.26 (3H, s), 4.11 (1H, t, J = 8.2 Hz), 7.17 (1H, d, J = 1.2 Hz), 7.42 (1H, dd, J = 8.1, 1.2 Hz), 7.81 (1H, d, J = 8.1 Hz), 8.95 (1H, d, J = 1.5 Hz), 9.43 (1H, d, J = 1.5 Hz), 11.69 (1H, br s) ESI+: 532 |

TABLE 58

| | | |
|---|---|---|
| 78 | 20 | diastereo mixture<br>NMR1; 0.80-0.92 (2H, m), 0.98-1.21 (6H, m), 1.22-2.36 (9H, m), 2.42 (3H, s), 2.70-2.88 (1H, m), 2.93-3.10 (1H, m), 3.89-4.18 (2H, m), 4.32 (1H, d, J = 3.7 Hz), 7.14 (1H, s), 7.38 (1H, d, J = 8.1 Hz), 7.78 (1H, d, J = 8.1 Hz), 8.27 (1H, br s), 9.17 (1H, br s), 10.92 (1H, br s)<br>NMR1; 0.80-0.92 (2H, m), 0.98-1.21 (6H, m), 1.22-2.36 (9H, m), 2.42 (3H, s), 2.70-2.88 (1H, m), 2.93-3.10 (1H, m), 3.89-4.18 (2H, m), 4.43 (1H, d, J = 4.1 Hz), 7.14 (1H, s), 7.38 (1H, d, J = 8.1 Hz), 7.78 (1H, d, J = 8.1 Hz), 8.27 (1H, br s), 9.17 (1H, br s), 10.92 (1H, br s)ESI+: 470 |
| 79 | 20 | diastereo mixture<br>NMR1; 0.78-0.92 (2H, m), 0.99-1.19 (6H, m), 1.20-2.40 (9H, m), 2.69-2.88 (1H, m), 2.93-3.11 (1H, m), 3.87 (3H, s), 3.91-4.16 (2H, m), 4.32 (1H, d, J = 3.5 Hz), 7.13 (1H, s), 7.38 (1H, d, J = 8.5 Hz), 7.77 (1H, d, J = 8.5 Hz), 8.07-8.12 (1H, m), 8.84 (1H, d, J = 1.5 Hz), 10.83 (1H, br s)<br>NMR1; 0.78-0.92 (2H, m), 0.99-1.19 (6H, m), 1.20-2.40 (9H, m), 2.69-2.88 (1H, m), 2.93-3.11 (1H, m), 3.87 (3H, s), 3.91-4.16 (2H, m), 4.43 (1H, d, J = 4.0 Hz), 7.13 (1H, s), 7.38 (1H, d, J = 8.5 Hz), 7.77 (1H, d, J = 8.5 Hz), 8.07-8.12 (1H, m), 8.84 (1H, d, J = 1.5 Hz), 10.82 (1H, br s) ESI+: 486 |
| 80 | 20 | diastereo mixture<br>NMR1: 0.75-0.95 (2H, m), 0.99-2.45 (15H, m), 2.69-2.88 (1H, m), 2.94-3.08 (1H, m), 3.93-4.16 (2H, m), 4.32 (1H, d, J = 3.8 Hz), 7.13 (1H, s), 7.38 (1H, d, J = 8.0 Hz), 7.79 (1H, d, J = 8.0 Hz), 8.53-8.57 (1H, m), 9.13 (1H, d, J = 1.4 Hz), 11.25 (1H, br s)NMR1: 0.75-0.95 (2H, m), 0.99-2.45 (15H, m), 2.69-2.88 (1H, m), 2.94-3.08 (1H, m), 3.93-4.16 (2H, m), 4.44 (1H, d, J = 4.0 Hz), 7.13 (1H, s), 7.38 (1H, d, J = 8.0 Hz), 7.79 (1H, d, J = 8.0 Hz), 8.53-8.57 (1H, m), 9.13 (1H, d, J = 1.4 Hz), 11.25 (1H, br s) ESI+: 490 |
| 81 | 20 | diastereo mixture<br>NMR1: 0.71-0.93 (2H, m), 0.98-2.69 (18H, m), 2.72-2.85 (1H, m), 2.92-3.08 (1H, m), 3.35-3.70 (2H, m), 3.91-4.14 (2H, m), 7.15 (1H, s), 7.37 (1H, d, J = 8.7 Hz), 7.59 (1H, dd, J = 8.0, 1.7 Hz), 7.77 (1H, d, J = 8.7 Hz), 7.93 (1H, dd, J = 8.0, 3.6 Hz), 8.13 (1H, br s), 10.71 (1H, br s) ESI+: 469 |

TABLE 59

| | | |
|---|---|---|
| 11 | 11 | NMR1: 0.78-0.94 (2H, m), 0.98-1.30 (6H, m), 1.43-1.64 (1H, m), 1.75-2.34 (8H, m), 2.71-2.88 (1H, m), 2.93-3.09 (1H, m), 3.70 (2H, dt, J = 5.5, 5.5 Hz), 4.02 (1H, t, J = 6.8 Hz), 4.26 (2H, t, J = 5.5 Hz), 4.85 (1H, t, J = 5.5 Hz), 7.16 (1H, d, J = 1.7 Hz), 7.41 (1H, dd, J = 8.4, 1.7 Hz), 7.79 (1H, d, J = 8.4 Hz), 8.08 (1H, d, J = 1.5 Hz), 8.82 (1H, d, J = 1.5 Hz), 10.84 (1H, br s) ESI+: 514 |
| 82 | 2 | NMR2: 0.83-0.95 (2H, m), 0.98-1.08 (2H, m), 1.11-1.20 (2H, m), 1.27-1.37 (2H, m), 1.50-1.60 (1H, m), 1.80-1.91 (1H, m), 1.92-2.20 (4H, m), 2.24-2.45 (3H, m), 2.58-2.62 (2H, m), 2.75-3.00 (4H, m), 3.49-3.59 (1H, m), 3.66 (3H, s), 6.95-7.00 (1H, m), 7.20-7.32 (1H, m), 7.42-7.59 (3H, m), 7.63-7.70 (1H, m) EI: 538 |

TABLE 59-continued

| | | |
|---|---|---|
| 83 | 9 | diastereo mixture<br>NMR1: 0.79-0.95 (2H, m), 0.99-1.26 (6H, m), 1.35 (3H, d, J = 5.0 Hz),<br>1.42-1.63 (1H, m), 1.73-2.38 (8H, m), 2.70-2.88 (1H, m), 2.92-3.14 (1H,<br>m), 4.05 (1H, t, J = 7.5 Hz), 4.68-4.84 (1H, m), 5.47-5.52 (1H, m),<br>7.17 (1H, s), 7.42 (1H, d, J = 8.2 Hz), 7.80 (1H, d, J = 8.2 Hz), 8.46 (1H, s),<br>9.20 (1H, s), 11.06 (1H, br s)<br>NMR1: 0.79-0.95 (2H, m), 0.99-1.26 (6H, m), 1.38 (3H, d, J = 5.0 Hz),<br>1.42-1.63 (1H, m), 1.73-2.38 (8H, m), 2.70-2.88 (1H, m), 2.92-3.14 (1H,<br>m), 4.05 (1H, t, J = 7.5 Hz), 4.68-4.84 (1H, m), 5.47-5.52 (1H, m),<br>7.17 (1H, s), 7.42 (1H, d, J = 8.2 Hz), 7.80 (1H, d, J = 8.2 Hz), 8.46 (1H, s),<br>9.20 (1H, s), 11.06 (1H, br s)<br>ESI+: 498 |
| 84 | 12 | ESI+: 525 |
| 12 | 12 | ESI+: 511 |
| 22-1 | 22 | NMR2: 0.78-0.94 (2H, m), 1.09-1.32 (4H, m), 1.38-1.79 (6H, m),<br>1.82-1.95 (1H, m), 1.99-2.10 (1H, m), 2.53-2.69 (1H, m), 2.82-2.91 (1H, m),<br>2.95-3.05 (1H, m), 3.75 (3H, s), 4.38-4.47 (1H, m), 6.74-6.76 (1H, m),<br>6.83-6.87 (1H, m), 7.00 (1H, d, J = 10.8 Hz), 7.18-7.22 (1H, m),<br>7.23-7.26 (1H, m), 7.42 (1H, brs), 8.01 (1H, d, J = 8.0 Hz)<br>FAB+: 456 |
| 22-2 | 22 | NMR2: 0.79-0.90 (2H, m), 1.09-1.23 (4H, m), 1.37-1.78 (7H, m),<br>1.99-2.09 (1H, m), 2.20-2.32 (1H, m), 2.83-3.03 (2H, m), 3.76 (3H, s),<br>4.27-4.35 (1H, m), 6.77 (1H, d, J = 2 Hz), 6.84 (1H, d, J = 2 Hz), 7.12 (1H, d, J = 10 Hz),<br>7.18 (1H, dd, J = 8, 2 Hz), 7.24-7.26 (1H, m), 7.47 (1H, brs),<br>8.00 (1H, d, J = 8 Hz) |
| 16 | 16 | ESI+: 440 |

TABLE 60

| | | |
|---|---|---|
| 85 | 20 | diastereo mixture<br>NMR1: 0.78-0.91 (2H, m), 0.94-2.30 (15H, m), 2.71-2.88 (1H, m),<br>2.91-3.05 (1H, m), 3.58 (3H, s), 3.67-3.74 (2H, m), 3.74-3.82 (1H, m),<br>3.94-4.04 (1H, m), 6.37-6.43 (1H, m), 7.10 (1H, s), 7.34 (1H, d, J = 8.0 Hz),<br>7.49-7.52 (1H, m), 7.77 (1H, d, J = 8.0 Hz), 10.62 (1H, br s)<br>NMR1: 0.78-0.91 (2H, m), 0.94-2.30 (15H, m), 2.71-2.88 (1H, m),<br>2.91-3.05 (1H, m), 3.58 (3H, s), 3.67-3.74 (2H, m), 3.74-3.82 (1H, m),<br>4.05-4.12 (1H, m), 6.37-6.43 (1H, m), 7.10 (1H, s), 7.34 (1H, d, J = 8.0 Hz),<br>7.49-7.52 (1H, m), 7.77 (1H, d, J = 8.0 Hz), 10.62 (1H, br s)<br>ESI+: 458 |
| 86 | 20 | diastereo mixture<br>NMR1: 0.71-0.95 (2H, m), 0.97-2.40 (21H, m), 2.72-2.90 (1H, m),<br>2.93-3.11 (1H, m), 3.94-4.15 (2H, m), 5.37 (1H, br s), 7.14 (1H, s), 7.39 (1H, d,<br>J = 8.4 Hz), 7.79 (1H, d, J = 8.4 Hz), 8.58 (1H, d, J = 1.5 Hz), 9.18 (1H, d,<br>J = 1.5 Hz), 11.01 (1H, br s)NMR1: 0.71-0.95 (2H, m), 0.97-2.40 (21H,<br>m), 2.72-2.90 (1H, m), 2.93-3.11 (1H, m), 3.94-4.15 (2H, m), 5.37 (1H, br<br>s), 7.14 (1H, s), 7.39 (1H, d, J = 8.4 Hz), 7.79 (1H, d, J = 8.4 Hz),<br>8.59 (1H, d, J = 1.5 Hz), 9.18 (1H, d, J = 1.5 Hz), 11.02 (1H, br s)<br>ESI−: 512 |
| 87 | 9 | NMR1: 0.79-0.91 (2H, m), 1.00-1.10 (4H, m), 1.12-1.76 (14H, m),<br>1.99-2.19 (1H, m), 2.71-2.86 (1H, m), 2.92-3.08 (1H, m), 3.12-3.28 (2H, m),<br>3.71-3.87 (2H, m), 4.05-4.17 (1H, m), 5.38 (1H, s), 7.15 (1H, d, J = 1.5 Hz),<br>7.40 (1H, dd, J = 8.3, 1.5 Hz), 7.79 (1H, d, J = 8.3 Hz), 8.58 (1H, d, J = 1.5 Hz),<br>9.18 (1H, d, J = 1.5 Hz), 11.03 (1H, br s)<br>ESI−: 512 |
| 88 | 9 | NMR1: 0.76-0.92 (2H, m), 0.99-1.10 (4H, m), 1.11-1.43 (5H, m),<br>1.47-1.72 (3H, m), 2.01-2.16 (1H, m), 2.42 (3H, s), 2.72-2.85 (1H, m),<br>2.94-3.08 (1H, m), 3.13-3.25 (2H, m), 3.69-3.88 (2H, m), 4.06-4.13 (1H, m),<br>7.14 (1H, d, J = 1.4 Hz), 7.39 (1H, dd, J = 8.4, 1.4 Hz), 7.77 (1H, d, J = 8.4 Hz),<br>8.27 (1H, d, J = 1.1 Hz), 9.17 (1H, d, J = 1.1 Hz), 10.94 (1H, br s)<br>ESI+: 470 |
| 89 | 9 | NMR1: 0.77-0.96 (2H, m), 0.99-1.75 (12H, m), 1.97-2.22 (1H, m),<br>2.68-2.89 (1H, m), 2.93-3.09 (1H, m), 3.10-3.28 (2H, m), 3.70-3.85 (2H, m),<br>3.88 (3H, s), 4.11-4.20 (1H, m), 7.15 (1H, d, J = 1.3 Hz), 7.40 (1H, dd, J = 8.3,<br>1.3 Hz), 7.80 (1H, d, J = 8.3 Hz), 8.96 (1H, d, J = 1.5 Hz), 9.41 (1H,<br>d, J = 1.5 Hz), 11.49 (1H, br s)<br>ESI+: 514 |

TABLE 61

| | | |
|---|---|---|
| 90 | 11 | NMR1: 0.77-0.94 (2H, m), 0.99-1.74 (12H, m), 1.97-2.19 (1H, m), 2.70-2.87 (1H, m), 2.93-3.09 (1H, m), 3.12-3.27 (2H, m), 3.70 (2H, dt, J = 6.0, 6.0 Hz), 3.74-3.86 (2H, m), 4.02-4.13 (1H, m), 4.26 (1H, t, J = 6.0 Hz), 4.85 (1H, t, J = 6.0 Hz), 7.14 (1H, d, J = 1.6 Hz), 7.39 (1H, d, J = 8.5, 1.6 Hz), 7.77 (1H, d, J = 8.5 Hz), 8.07 (1H, d, J = 1.4 Hz), 8.81 (1H, d, J = 1.4 Hz), 10.81 (1H, br s)<br>ESI+: 516 |
| 23 | 23 | diastereo mixture<br>NMR1: 0.79-0.93 (2H, m), 0.99-1.10 (4H, m), 1.11-1.29 (5H, m), 1.34 (3H, d, J = 6.4 Hz), 1.48-1.73 (3H, m), 1.97-2.15 (1H, m), 2.71-2.88 (1H, m), 2.94-3.07 (1H, m), 3.13-3.28 (2H, m), 3.71-3.83 (2H, m), 4.05-4.17 (1H, m), 4.71-4.84 (1H, m), 5.47-5.53 (1H, m), 7.15 (1H, s), 7.40 (1H, d, J = 8.3 Hz), 7.79 (1H, d, J = 8.3 Hz), 8.45 (1H, s), 9.19 (1H, s), 11.03 (1H, br s)NMR1: 0.79-0.93 (2H, m), 0.99-1.10 (4H, m), 1.11-1.29 (5H, m), 1.38 (3H, d, J = 5.8 Hz), 1.48-1.73 (3H, m), 1.97-2.15 (1H, m), 2.71-2.88 (1H, m), 2.94-3.07 (1H, m), 3.13-3.28 (2H, m), 3.71-3.83 (2H, m), 4.05-4.17 (1H, m), 4.71-4.84 (1H, m), 5.47-5.53 (1H, m), 7.15 (1H, s), 7.40 (1H, d, J = 8.3 Hz), 7.79 (1H, d, J = 8.3 Hz), 8.45 (1H, s), 9.19 (1H, s), 11.03 (1H, br s)<br>ESI−: 498 |
| 91 | 9 | diastereo mixute<br>NMR1: 0.77-0.94 (2H, m), 0.97-1.77 (18H, m), 1.99-2.17 (1H, m), 2.70-2.86 (1H, m), 2.90-3.06 (3H, m), 3.10-3.27 (2H, m), 3.28-3.44 (1H, m), 3.51-3.62 (1H, m), 3.63-3.73 (1H, m), 3.74-3.85 (2H, m), 3.86-3.98 (1H, m), 4.05-4.17 (1H, m), 4.50-4.61 (1H, m), 7.14 (1H, d, J = 1.4 Hz), 7.39 (1H, dd, J = 8.2, 1.4 Hz), 7.77 (1H, d, J = 8.2 Hz), 8.31 (1H, s), 9.21 (1H, s), 10.97 (1H, br s)<br>ESI+: 500 (—$C_5H_8O$; detetrahydropyranylation) |
| 14 | 14 | NMR1: 0.78-0.94 (2H, m), 0.96-1.11 (4H, m), 1.12-1.43 (5H, m), 1.46-1.73 (3H, m), 2.00-2.16 (1H, m), 2.71-2.90 (3H, m), 2.93-3.06 (1H, m), 3.12-3.28 (2H, m), 3.63-3.75 (2H, m), 3.76-3.87 (2H, m), 4.03-4.17 (1H, m), 4.64 (1H, t, J = 5.4 Hz), 7.15 (1H, d, J = 1.3 Hz), 7.39 (1H, dd, J = 8.1, 1.3 Hz), 7.77 (1H, d, J = 8.1 Hz), 8.27 (1H, d, J = 1.5 Hz), 9.20 (1H, d, J = 1.5 Hz), 10.96 (1H, br s)<br>ESI+: 500 |
| 17 | 17 | ESI+: 442 |

TABLE 62

| | | |
|---|---|---|
| 92 | 9 | NMR1: 0.78-0.92 (2H, m), 0.99-1.10 (4H, m), 1.11-1.37 (5H, m), 1.46-1.73 (3H, m), 2.02-2.17 (1H, m), 2.73-2.86 (1H, m), 2.93-3.06 (1H, m), 3.11-3.27 (2H, m), 3.74-3.83 (2H, m), 4.00-4.09 (1H, m), 7.11 (1H, d, J = 1.4 Hz), 7.22 (1H, d, J = 3.7 Hz), 7.37 (1H, dd, J = 8.3, 1.4 Hz), 7.46 (1H, d, J = 3.7 Hz), 7.79 (1H, d, J = 8.3 Hz), 12.38 (1H, br s)<br>ESI+: 461 |
| 93 | 9 | NMR1: 0.74-0.93 (2H, m), 0.96-1.10 (4H, m), 1.11-1.44 (5H, m), 1.46-1.72 (3H, m), 2.01-2.17 (1H, m), 2.71-2.85 (1H, m), 2.92-3.08 (1H, m), 3.15-3.27 (2H, m), 3.72-3.86 (2H, m), 4.07-4.18 (1H, m), 7.15 (1H, d, J = 1.4 Hz), 7.40 (1H, d, J = 8.4, 1.4 Hz), 7.79 (1H, d, J = 8.4 Hz), 8.36 (1H, d, J = 2.6 Hz), 8.39 (1H, dd, J = 2.6, 1.6 Hz), 9.31 (1H, d, J = 1.6 Hz), 11.06 (1H, br s)<br>ESI+: 456 |
| 94 | 9 | NMR1: 0.77-0.93 (2H, m), 0.99-1.10 (4H, m), 1.12-1.46 (5H, m), 1.47-1.73 (3H, m), 2.00-2.20 (4H, m), 2.69-2.88 (1H, m), 2.92-3.08 (1H, m), 3.10-3.27 (2H, m), 3.72-3.88 (2H, m), 4.03-4.18 (1H, m), 5.13 (2H, s), 7.14 (1H, d, J = 1.5 Hz), 7.39 (1H, dd, J = 8.4, 1.5 Hz), 7.79 (1H, d, J = 8.4 Hz), 8.45 (1H, d, J = 1.4 Hz), 9.28 (1H, d, J = 1.4 Hz), 11.15 (1H, br s)<br>ESI+: 528 |
| 95 | 9 | diastereo mixture<br>NMR1: 0.77-0.94 (2H, m), 0.98-1.31 (9H, m), 1.35-1.74 (9H, m), 1.99-2.20 (1H, m), 2.69-2.88 (1H, m), 2.94-3.07 (1H, m), 3.12-3.28 (2H, m), 3.72-3.85 (2H, m), 3.86-3.99 (1H, m), 4.07-4.18 (1H, m), 4.27-4.41 (1H, m), 5.11-5.21 (1H, m), 7.15 (1H, s), 7.40 (1H, d, J = 8.4 Hz), 7.79 (1H, d, J = 8.4 Hz), 8.44 (1H, s), 9.26 (1H, s), 11.12 (1H, br s)<br>ESI+: 556 |
| 13 | 13 | NMR1: 0.75-0.95 (2H, m), 0.98-1.09 (4H, m), 1.11-1.46 (5H, m), 1.48-1.71 (3H, m), 1.99-2.17 (1H, m), 2.70-2.86 (1H, m), 2.93-3.08 (1H, m), 3.11-3.27 (2H, m), 3.73-3.88 (2H, m), 4.04-4.18 (1H, m), 4.57 (2H, d, J = 5.5 Hz), 5.50 (1H, t, J = 5.5 Hz), 7.15 (1H, d, J = 1.4 Hz), 7.40 (1H, dd, J = 8.2, 1.4 Hz), 7.79 (1H, d, J = 8.2 Hz), 8.41 (1H, d, J = 1.3 Hz), 9.21 (1H, d, J = 1.3 Hz), 11.03 (1H, br s)<br>ESI−: 484 |

TABLE 63

| | | |
|---|---|---|
| 18 | 18 | diastereo mixture<br>NMR1: 0.77-0.93 (2H, m), 0.98-1.45 (9H, m), 1.47-1.73 (3H, m),<br>1.99-2.21 (1H, m), 2.67-2.90 (1H, m), 2.93-3.09 (1H, m), 3.11-3.28 (2H, m),<br>3.46-3.59 (1H, m), 3.60-3.72 (1H, m), 3.74-3.86 (2H, m), 4.05-4.18 (1H,<br>m), 4.56-4.65 (1H, m), 4.66-4.74 (1H, m), 5.53 (1H, dd, J = 5.0, 2.8 Hz),<br>7.15 (1H, s), 7.40 (1H, d, J = 8.3 Hz), 7.79 (1H, d, J = 8.3 Hz), 8.41 (1H,<br>d, J = 1.5 Hz), 9.21 (1H, d, J = 1.5 Hz), 11.03 (1H, br s)<br>ESI-: 514 |
| 96 | 9 | NMR1: 0.77-0.95 (2H, m), 1.00-1.44 (9H, m), 1.47-1.71 (3H, m),<br>1.99-2.17 (1H, m), 2.71-2.87 (1H, m), 2.94-3.10 (1H, m), 3.13-3.27 (2H, m),<br>3.74-3.85 (2H, m), 3.87 (3H, s), 4.02-4.13 (1H, m), 7.14 (1H, s), 7.39 (1H,<br>d, J = 8.2 Hz), 7.79 (1H, d, J = 8.2 Hz), 8.09 (1H, d, J = 1.4 Hz), 8.84 (1H,<br>d, J = 1.4 Hz), 10.82 (1H, br s)<br>ESI+: 486 |
| 97 | 9 | NMR1: 0.77-0.95 (2H, m), 1.00-1.10 (4H, m), 1.12-1.45 (5H, m),<br>1.48-1.74 (3H, m), 2.02-2.19 (1H, m), 2.58 (3H, s), 2.73-2.87 (1H, m),<br>2.96-3.07 (1H, m), 3.13-3.27 (2H, m), 3.73-3.89 (2H, m), 4.12-4.19 (1H, m),<br>7.15 (1H, d, J = 1.5 Hz), 7.40 (1H, dd, J = 8.2, 1.5 Hz), 7.80 (1H, d, J = 8.2 Hz),<br>8.88 (1H, d, J = 1.5 Hz), 9.38 (1H, d, J = 1.5 Hz), 11.48 (1H, br s)<br>ESI+: 498 |
| 98 | 9 | ESI+: 582 |
| 15 | 15 | NMR1: 0.83-0.89 (2H, m), 1.00-1.09 (4H, m), 1.12-1.18 (2H, m),<br>1.46-1.57 (1H, m), 1.82-1.92 (2H, m), 1.94-2.17 (4H, m), 2.18-2.26 (2H, m),<br>2.75-2.82 (1H, m), 2.96-3.04 (1H, m), 4.02-4.07 (1H, m), 4.56 (2H, brs),<br>5.52 (1H, brs), 7.16 (1H, d, J = 1.6 Hz), 7.42 (1H, dd, J = 1.6, 8.3 Hz),<br>7.79 (1H, d, J = 8.3), 8.41 (1H, d, J = 1.2 Hz), 9.21 (1H, d, J = 1.2 Hz),<br>11.1 (1H, s)<br>ESI-: 482 |
| 99 | 14 | NMR1: 0.81-0.94 (2H, m), 1.00-1.10 (4H, m), 1.11-1.27 (2H, m),<br>1.45-1.62 (1H, m), 1.77-2.32 (8H, m), 2.71-2.90 (3H, m), 2.94-3.08 (1H, m),<br>3.62-3.77 (2H, m), 4.05 (1H, t, J = 8.1 Hz), 4.59-4.74 (1H, m), 7.17 (1H,<br>d, J = 1.5 Hz), 7.42 (1H, dd, J = 8.2, 1.5 Hz), 7.80 (1H, d, J = 8.2 Hz),<br>8.27 (1H, d, J = 1.4 Hz), 9.21 (1H, d, J = 1.4 Hz), 10.99 (1H, br s)<br>ESI+: 498 |
| 100 | 15 | ESI-: 496 |
| 10 | 10 | NMR2: 0.89-0.91 (2H, m), 1.03-1.07 (2H, m), 1.14-1.23 (2H, m),<br>1.33-1.36 (8H, m), 1.56-1.59 (1H, m), 1.86-1.91 (1H, m), 2.01-2.40 (7H, m),<br>2.80-2.84 (1H, m), 2.92-2.98 (1H, m), 3.58-3.62 (1H, m), 4.20 (2H, s),<br>6.98-6.99 (1H, m), 7.29-7.32 (1H, m), 7.68-7.69 (1H, m), 7.92-7.95 (2H,<br>m), 8.97-8.98 (1H, m)<br>ESI+: 542 |
| 101 | 15 | ESI-: 532 |
| 102 | 15 | ESI+: 478 |
| 103 | 15 | ESI-: 518 |

TABLE 64

| No | Structure |
|---|---|
| 1 | 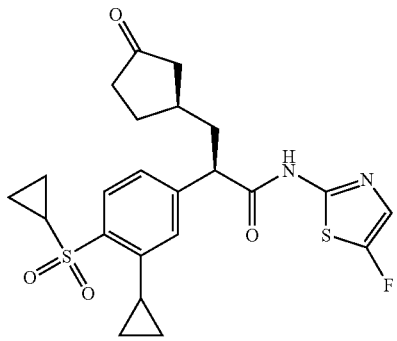 |
| 2 | 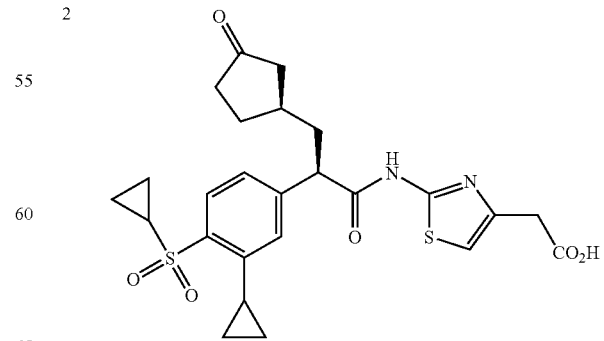 |

TABLE 64-continued

| No | Structure |
|----|-----------|
| 3 | 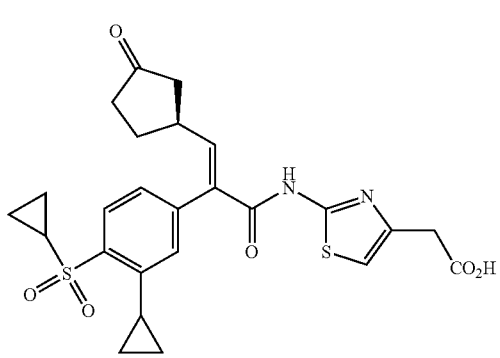 |
| 4 | 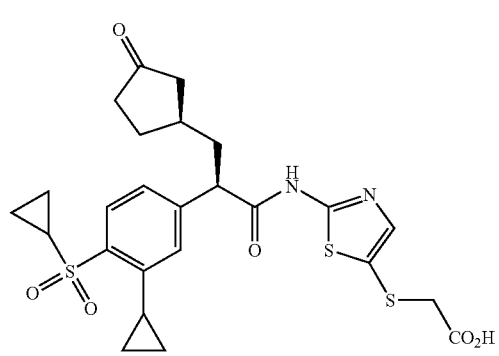 |

TABLE 65

| 5 | 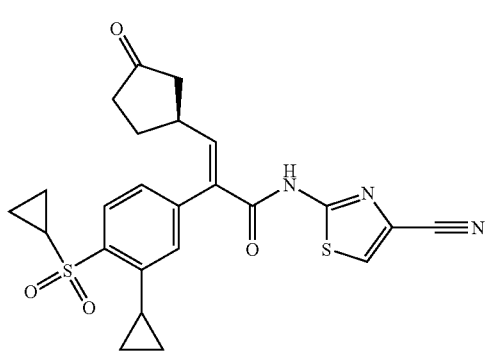 |
|---|---|
| 6 | 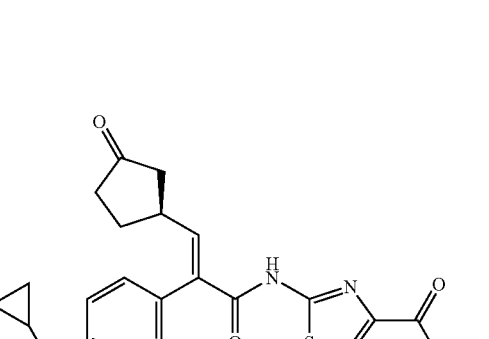 |

TABLE 65-continued

| 7 | 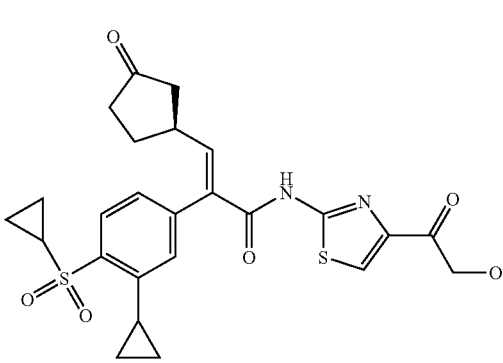 |
|---|---|
| 8 | 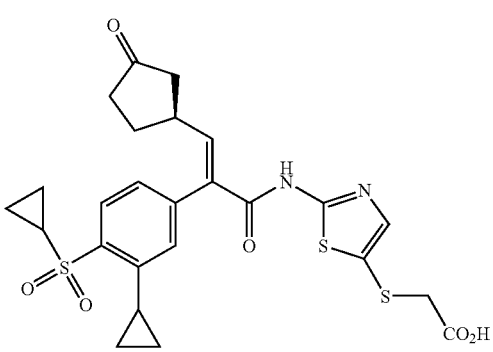 |
| 9 | 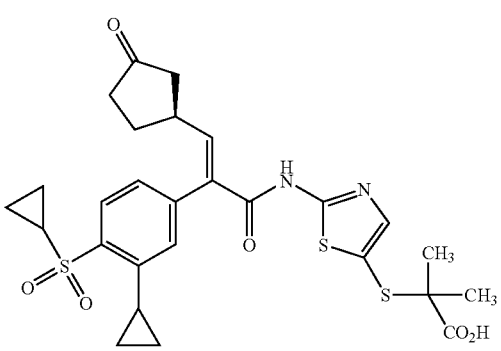 |

Since the compound of the present invention has a GK activation action, it is useful as a therapeutic and preventive agent for diabetes, in particular, type II diabetes. It is also useful as a therapeutic and preventive agent for complications of diabetes including nephropathy, retinopathy, neuropathy, disturbance of peripheral circulation, cerebrovascular accidents, ischemic heart disease and arteriosclerosis. In addition, it is also useful as a therapeutic and preventive agent for obesity and metabolic syndrome by suppressing overeating.

Explanation of "Artificial Sequence" is described in the numerical index <223> of the following SEQUENCE LISTING. Illustratively, the nucleotide sequences represented by SEQ ID NOs:1 and 2 of the SEQUENCE LISTING are artificially synthesized primer sequences.

The invention claimed is:

1. A compound of formula (I) or a pharmaceutically acceptable salt thereof:

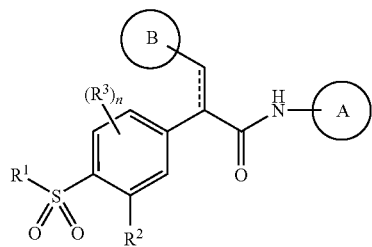

(I)

wherein $R^1$ is lower alkyl, halogeno-lower alkyl, or cycloalkyl,
$R^2$ is cycloalkyl,
$R^3$ is halogen, lower alkyl, halogeno-lower alkyl, $-OR^0$, or $-O$-halogeno-lower alkyl,
$R^0$ independently represents $-H$ or lower alkyl,
Ring A is pyrazinyl which may be substituted with up to five moieties independently selected from the group consisting of halogen, cyano, lower alkyl which may be substituted with $-OR^0$, halogen-lower alkyl, lower alkylene-$OC(O)R^0$, lower alkylene-$O$-hetero ring group, $-OR^0$, $-O$-halogeno-lower alkyl, $-O$-lower alkylene-$OR^0$, $-S(O)_p$-lower alkyl, $-S(O)_p$-lower alkylene-$OR^0$, $-C(O)R^0$, $-C(O)$-lower alkylene-$OR^0$, $-CO_2R^0$, lower alkylene-$CO_2R^0$, $-O$-lower alkylene-$CO_2R^0$, $-S(O)_p$-lower alkylene-$CO_2R^0$, $-C(O)N(R^0)_2$ and a hetero ring group, wherein the hetero ring group may be substituted with up to five moieties independently selected from the group consisting of halogen, lower alkyl, halogeno-lower alkyl, $-OR^0$, $-O$-halogeno-lower alkyl and oxo,
Ring B is aryl or heteroaryl which may each be substituted with up to five moieties independently selected from the group consisting of halogen, lower alkyl, halogeno-lower alkyl, $-OR^0$, and $-O$-halogeno-lower alkyl, or

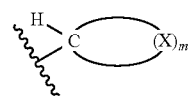

wherein

~~~ represents formula (I),

X independently represents $-C(R^4)(R^5)-$, $-C(O)-$, $-O-$, $-S(O)_p-$, or $-N(R^0)-$, m is 2, 3, 4, 5, 6 or 7, $R^4$ and $R^5$ independently represent $-H$, halogen, lower alkyl, halogeno-lower alkyl, $-OR^0$, or $-O$-halogeno-lower alkyl, and n and p independently represent 0, 1 or 2, provided that

----- means a single bond or a double bond.

2. The compound as described in claim 1, wherein n is 0.

3. The compound as described in claim 2, wherein $R^1$ is methyl, trifluoromethyl, or cyclopropyl.

4. The compound as described in claim 3, wherein $R^2$ is cyclopropyl.

5. The compound as described in claim 4, wherein formula (I) is

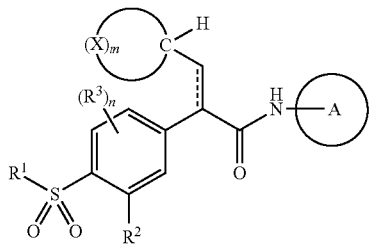

m is 4 or 5, and
none or one X is —CH(F)—, —CH(OH)—, —C(O)—, or —O—, and the remaining X is —CH$_2$—.

6. The compound as described in claim 5, wherein Ring A is pyrazinyl, which may be substituted with up to five moieties independently selected from the group consisting of halogen, cyano, lower alkyl which may be substituted with —OR$^O$, —OR$^O$, —O-lower alkylene —OR$^O$, and —C(O)R$^O$.

7. The compound as described in claim 6, wherein

----- is a single bond.

8. The compound as described in claim 6, wherein

----- is a double bond.

9. The compound as described in claim 8, wherein Ring B and the benzene ring of formula (I) are in a Z configuration with respect to the double bond.

10. The compound of claim 1, which is selected from the group consisting of:
(2E)-2-[3-cyclopropyl-4-(cyclopropylsulfonyl)phenyl]-N-(5-methylpyrazin-2-yl)-3-[(1S)-3-oxocyclopentyl]acrylamide,
(2R)-2-[3-cyclopropyl-4-(cyclopropylsulfonyl)phenyl]-N-(5-methylpyrazin-2-yl)-3-[(1R)-3-oxocyclopentyl]propanamide,
(2R)-2-[3-cyclopropyl-4-(cyclopropylsulfonyl)phenyl]-N-[5-(hydroxymethyl)pyrazin-2-yl]-3-[(1R)-3-oxocyclopentyl]propanamide,
(2R)—N-(5-chloropyrazin-2-yl)-2-[3-cyclopropyl-4-(cyclopropylsulfonyl)phenyl]-3-[(1R)-3-oxocyclopentyl]propanamide,
(2R)-2-[3-cyclopropyl-4-(cyclopropylsulfonyl)phenyl]-N-(5-methoxypyrazin-2-yl)-3-[(1R)-3-oxocyclopentyl]propanamide,
(2R)-2-[3-cyclopropyl-4-(cyclopropylsulfonyl)phenyl]-3-[(1R)-3-hydroxycyclopentyl]-N-(5-methylpyrazin-2-yl)propanamide,
(2R)-2-[3-cyclopropyl-4-(cyclopropylsulfonyl)phenyl]-3-[(1R)-3-hydroxycyclopentyl]-N-(5-methoxypyrazin-2-yl)propanamide,
(2R)-2-[3-cyclopropyl-4-(cyclopropylsulfonyl)phenyl]-N-[5-(2-hydroxy ethoxy)pyrazin-2-yl]-3-[(1R)-3-oxocyclopentyl]propanamide, and
(2R)-2-[3-cyclopropyl-4-(cyclopropylsulfonyl)phenyl]-N-[5-(2-hydroxy-2-methylpropoxy)pyrazin-2-yl]-3-[(1R)-3-oxocyclopentyl]propanamide,
or a pharmaceutically acceptable salt thereof.

11. The compound as described in claim 1, which is (2R)-2-[3-cyclopropyl-4-(cyclopropylsulfonyl)phenyl]-N-[5-(hydroxymethyl)pyrazin-2-yl]-3-[(1R)-3-oxocyclopentyl]propanamide or a pharmaceutically acceptable salt thereof.

12. The compound as described in claim 1, which is (2R)-2-[3-cyclopropyl-4-(cyclopropylsulfonyl)phenyl]-N-(5-methylpyrazin-2-yl)-3-[(1R)-3-oxocyclopentyl]propanamide or a pharmaceutically acceptable salt thereof.

13. The compound as described in claim 1, which is (2R)-2-[3-cyclopropyl-4-(cyclopropylsulfonyl)phenyl]-N-(5-methoxypyrazin-2-yl)-3-[(1R)-3-oxo cyclopentyl]propanamide or a pharmaceutically acceptable salt thereof.

14. The compound as described in claim 1, which is (2E)-2-[3-cyclopropyl-4-(cyclopropylsulfonyl)phenyl]-N-(5-methylpyrazin-2-yl)-3-[(1S)-3-oxocyclopentyl]acrylamide or a pharmaceutically acceptable salt thereof.

15. The compound as described in claim 1, which is (2R)—N-(5-acetylpyrazin-2-yl)-2-[3-cyclopropyl-4-(cyclopropylsulfonyl)phenyl]-3-[(1R)-3-oxocyclopentyl]propanamide or a pharmaceutically acceptable salt thereof.

16. A pharmaceutical composition comprising the compound or a pharmaceutically acceptable salt thereof as described in claim 1, and a pharmaceutically acceptable carrier.

* * * * *

SEQUENCE LISTING

<160> NUMBER OF SEQ ID NOS: 2

<210> SEQ ID NO 1
<211> LENGTH: 28
<212> TYPE: DNA
<213> ORGANISM: Artificial
<220> FEATURE:
<223> OTHER INFORMATION: Description of artificial sequence:primer
<220> FEATURE:
<223> OTHER INFORMATION: Inventor: Hayakawa, Masahiko; Kido, Yoshiyuki;
    Nigawara, Takahiro;
    Inventor: Okumura, Mitsuaki; Kanai, Akira; Maki, Keisuke;
    Inventor: Amino, Nobuaki

<400> SEQUENCE: 1

TAGAATTCAT GGCGATGGAT GTCACAAG                                          28

<210> SEQ ID NO 2
<211> LENGTH: 27
<212> TYPE: DNA
<213> ORGANISM: Artificial
<220> FEATURE:
<223> OTHER INFORMATION: Description of artificial sequence:primer

<400> SEQUENCE: 2

ATCTCGAGTC ACTGGCCCAG CATACAG                                           27